(12) United States Patent
Shefer et al.

(10) Patent No.: US 6,291,371 B1
(45) Date of Patent: *Sep. 18, 2001

(54) APPLICATION OF FILM FORMING TECHNOLOGY TO FRAGRANCE CONTROL RELEASE SYSTEMS; AND RESULTANT FRAGRANCE CONTROL RELEASE SYSTEM

(75) Inventors: Adi Shefer; Shmuel David Shefer, both of East Brunswick, NJ (US); Michael John Robert White, Amsterdam (NL)

(73) Assignee: International Flavors & Fragrances Inc.

( * ) Notice: Subject to any disclaimer, the term of this patent is extended or adjusted under 35 U.S.C. 154(b) by 0 days.

This patent is subject to a terminal disclaimer.

(21) Appl. No.: 09/358,471

(22) Filed: Jul. 21, 1999

Related U.S. Application Data

(63) Continuation-in-part of application No. 09/150,240, filed on Sep. 10, 1998, now Pat. No. 6,063,365.

(51) Int. Cl.[7] .............................. B32B 27/04; B32B 27/12
(52) U.S. Cl. .............................. 442/96; 442/76; 442/286; 442/394; 428/905
(58) Field of Search .............................. 442/76, 96, 286, 442/394; 428/905

(56) References Cited

U.S. PATENT DOCUMENTS

| | | | |
|---|---|---|---|
| 4,668,430 | 5/1987 | Schmolka | 252/522 R |
| 4,803,195 | 2/1989 | Holzner | 512/4 |
| 5,733,560 | 3/1998 | Davister et al. | 424/407 |

FOREIGN PATENT DOCUMENTS

| | | |
|---|---|---|
| 2008556 | 8/1990 | (CA) . |
| 0 075 540 | 3/1983 | (EP) . |
| 0 113 085 | 7/1984 | (EP) . |
| 0 281 034 | 9/1988 | (EP) . |
| 1478000 | 6/1977 | (GB) . |
| WO92/10923 | 7/1992 | (WO) . |
| 9725018 | 7/1997 | (WO) . |

Primary Examiner—Elizabeth M. Cole
Assistant Examiner—Ula C. Ruddock
(74) Attorney, Agent, or Firm—Joseph F. Leightner

(57) ABSTRACT

Described is a fragrance control release system which is an emulsifier-free, single phase, nonporous, continuous, permeable polymeric film having a substantially uniform thickness of from about 1 up to about 150 microns, having entrapped and dissolved therein molecules of at least one fragrance substance capable of evolving from said film into the environment proximate said film by means of molecular diffusion at a permeation rate of from about $1 \times 10^{-7}$ up to about 0.1 mg-mm/cm$^2$-min in a sustained and controlled release manner. Also described is a process for using the aforementioned system for imparting a fragrance into the environment above the unobstructed outer surface of the aforementioned polymer film which is coated on the surface of a solid or semi-solid support, e.g., a woven or non-woven fabric substrate; or a solid surface or human epidermis.

4 Claims, 48 Drawing Sheets

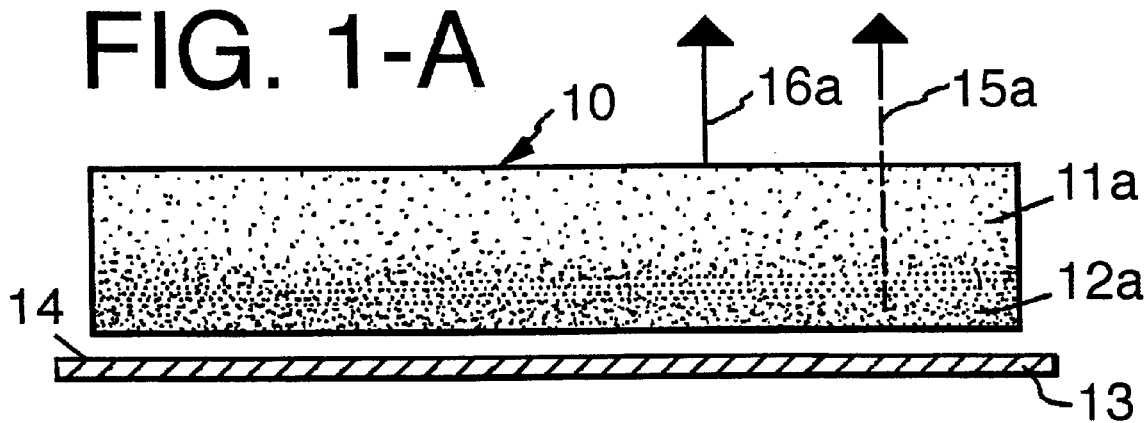
FIG. 1-A
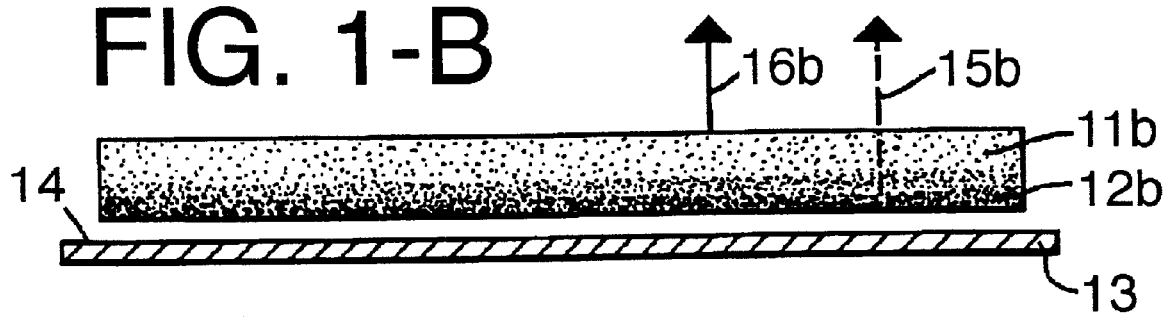
FIG. 1-B
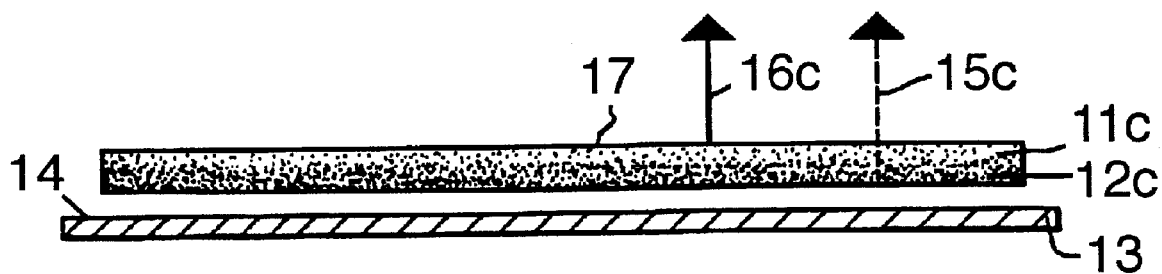
FIG. 1-C

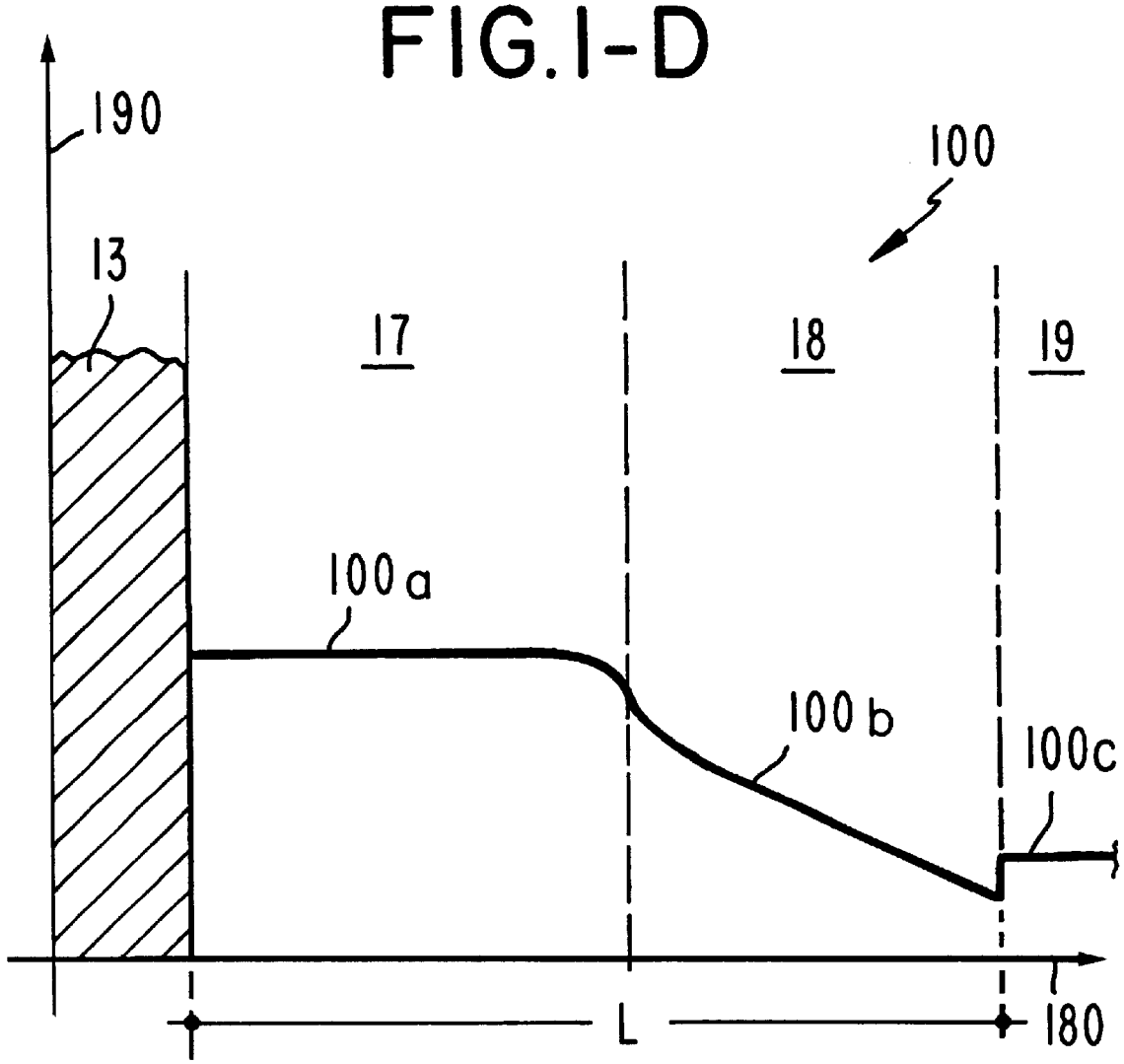

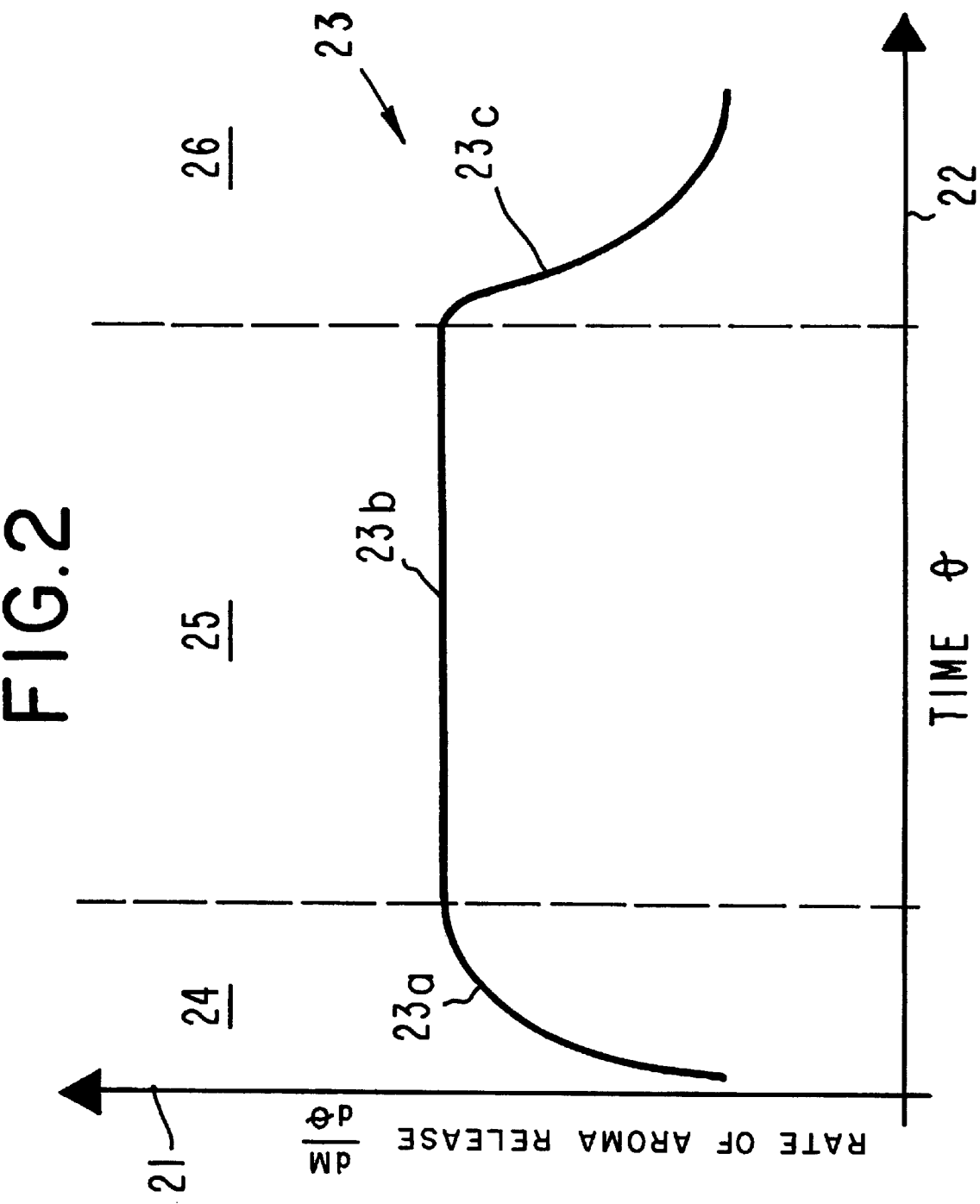

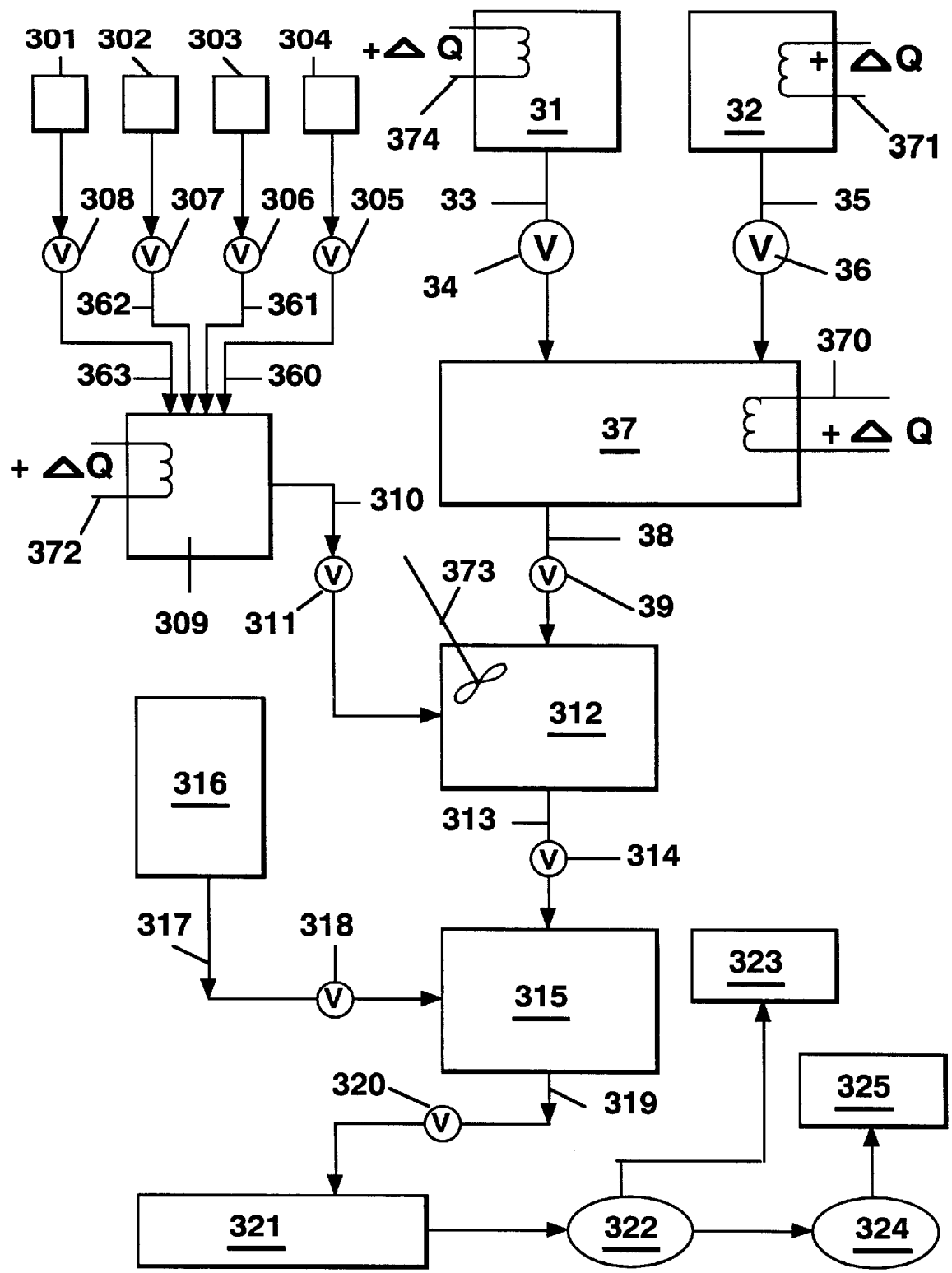
FIG. 3-A

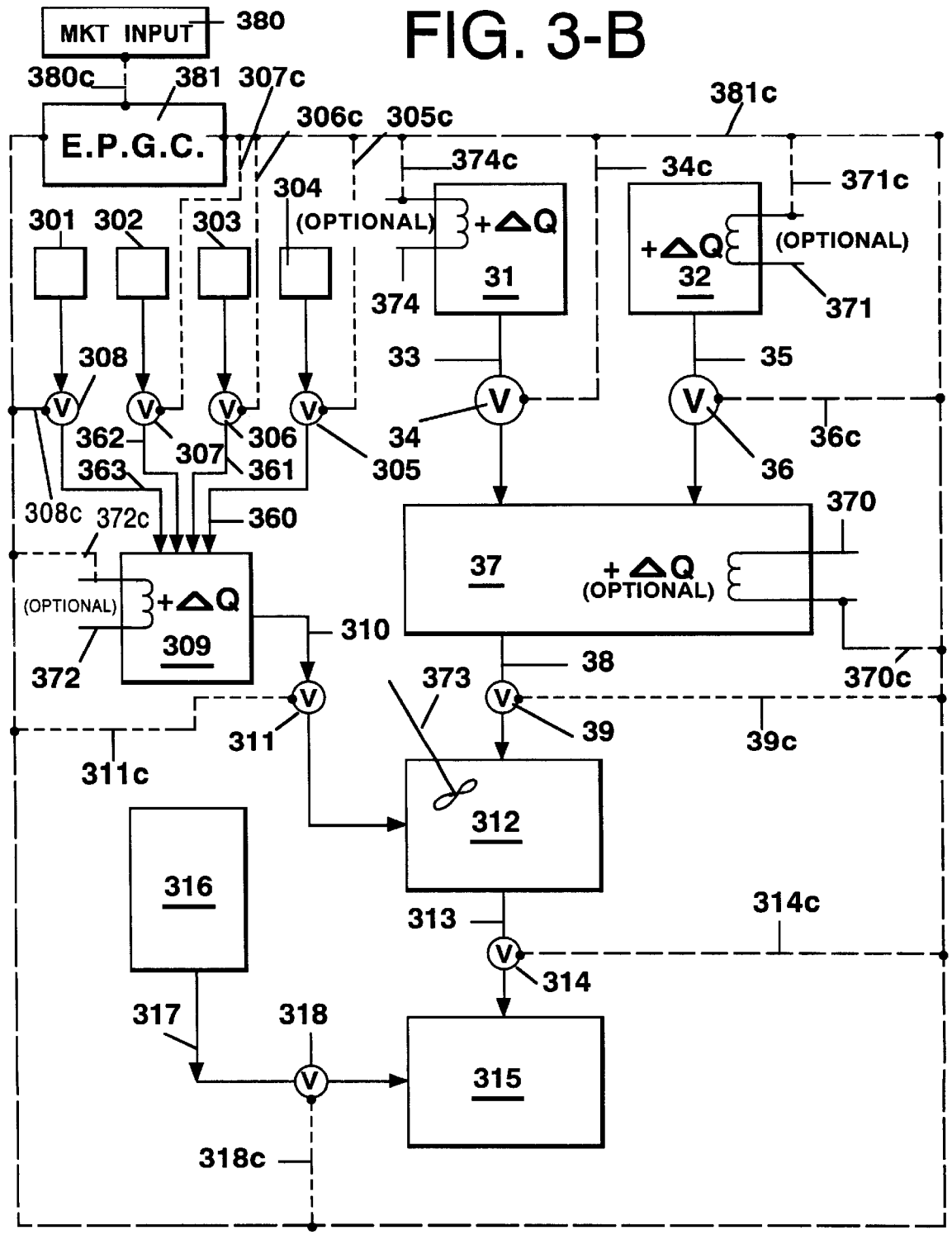
FIG. 3-B

FIG. 3-C
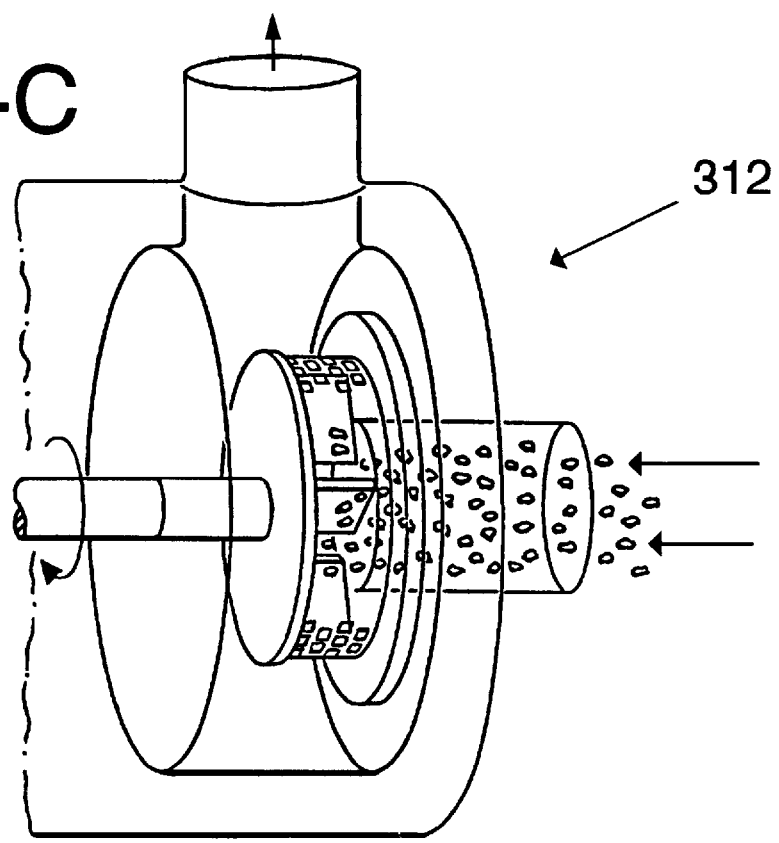
FIG. 3-D
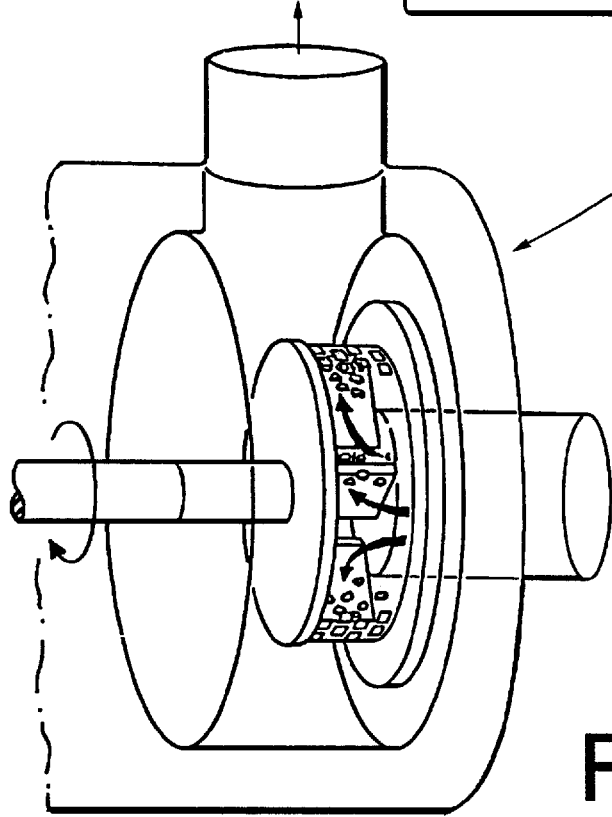

FIG.3-E
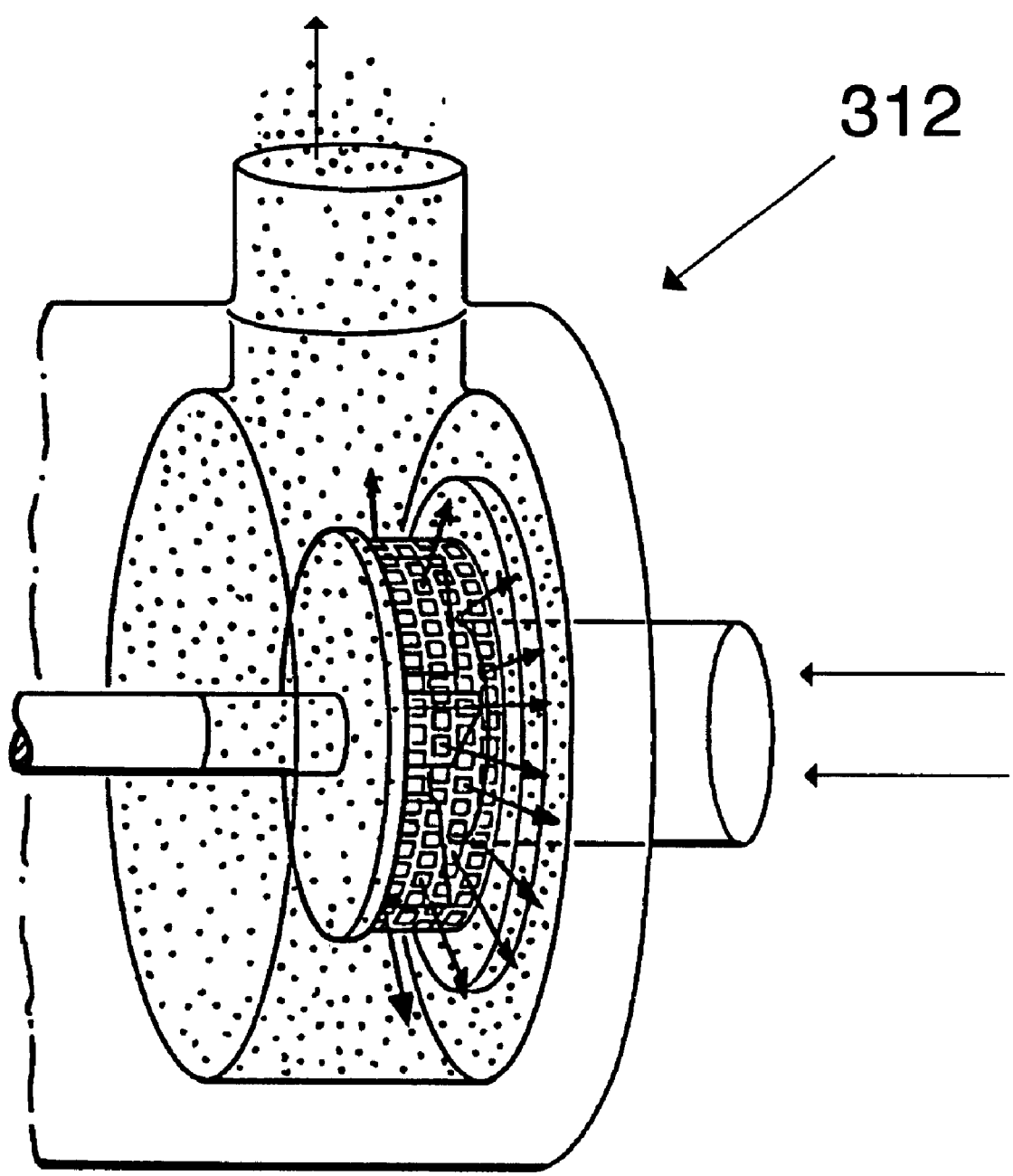

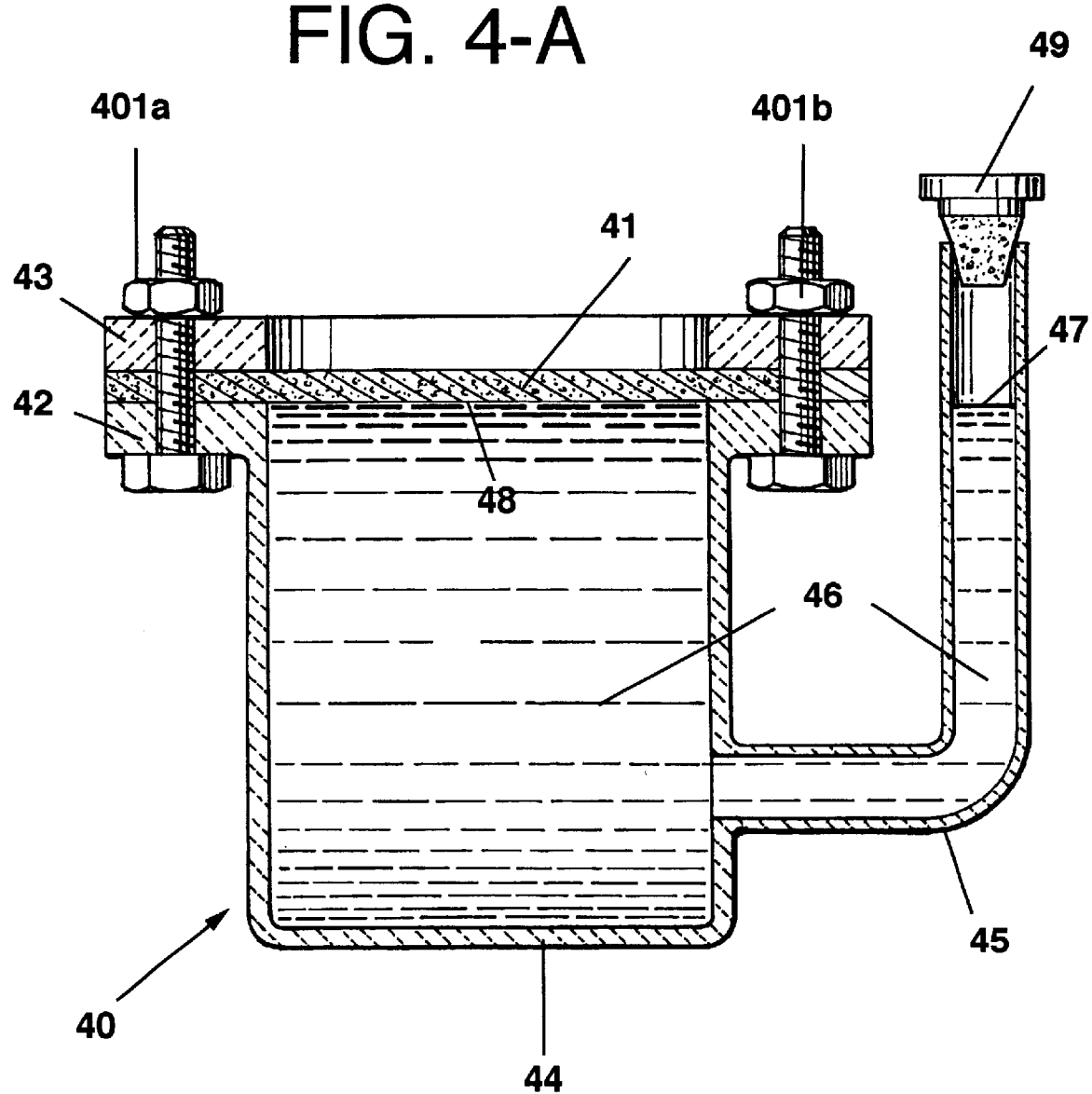

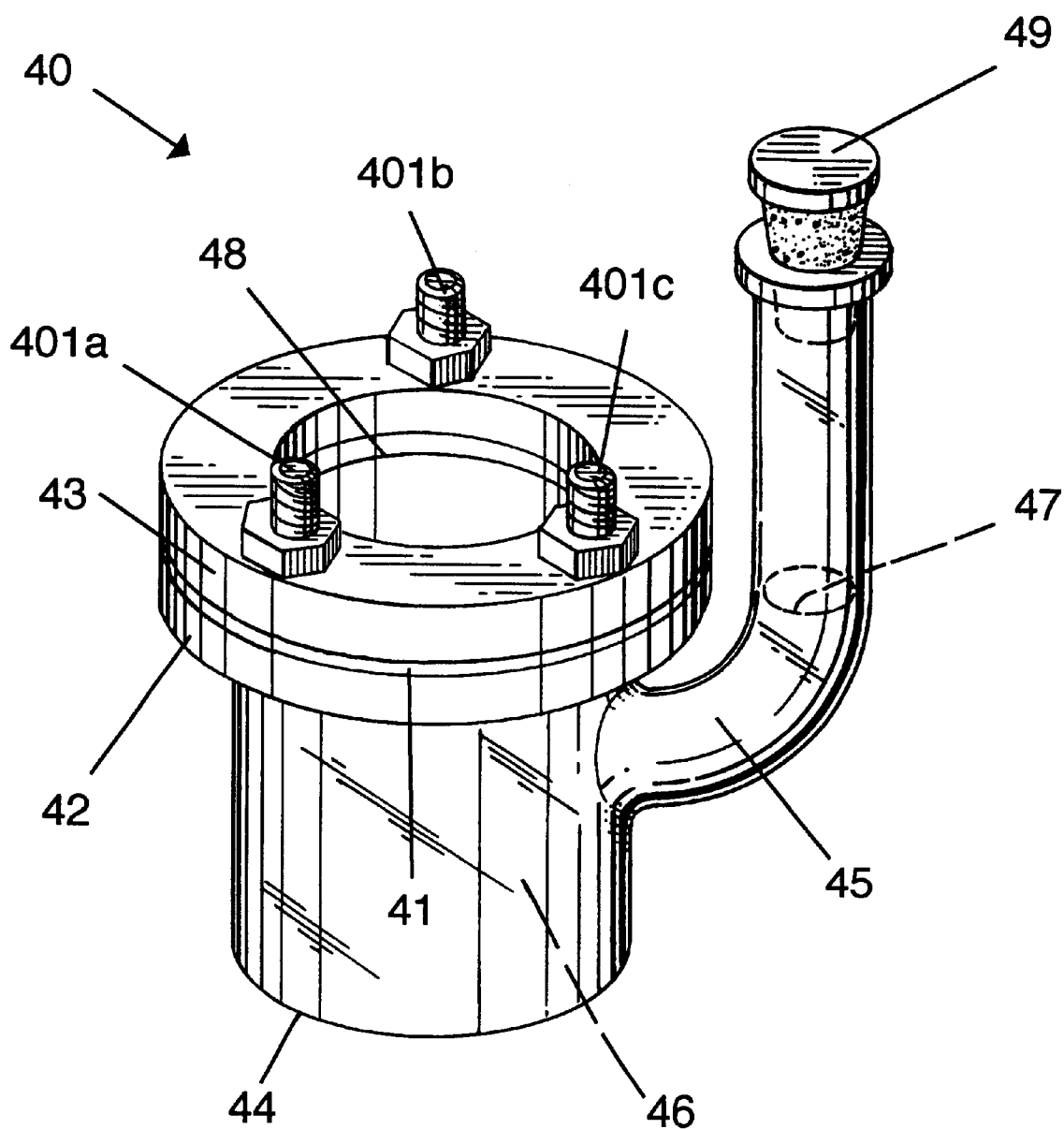
FIG.4-B

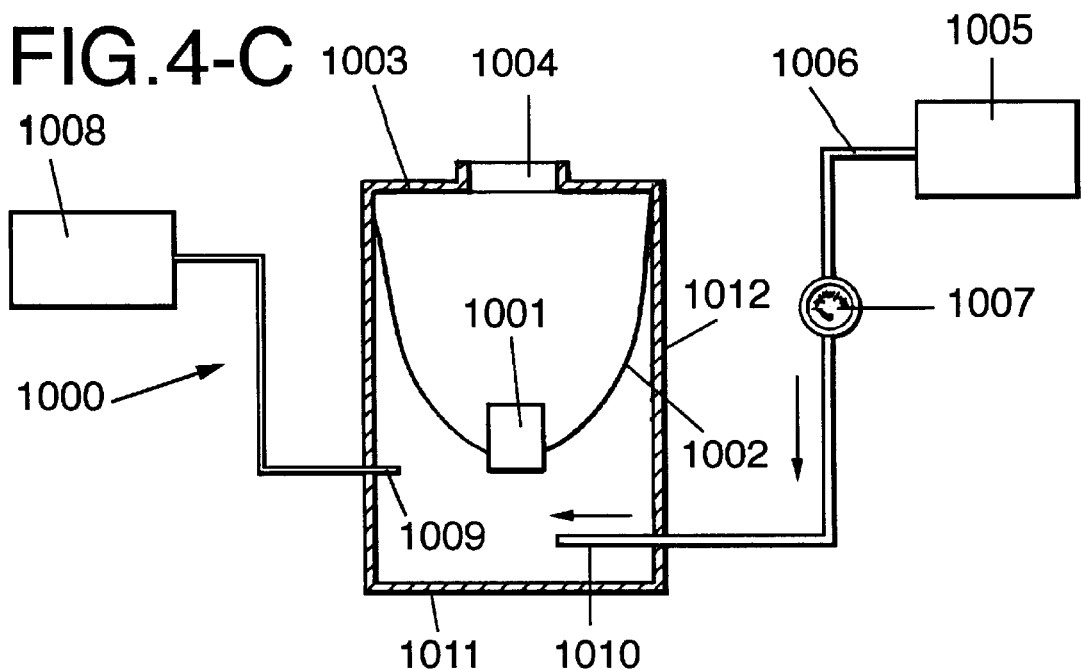
FIG.4-C
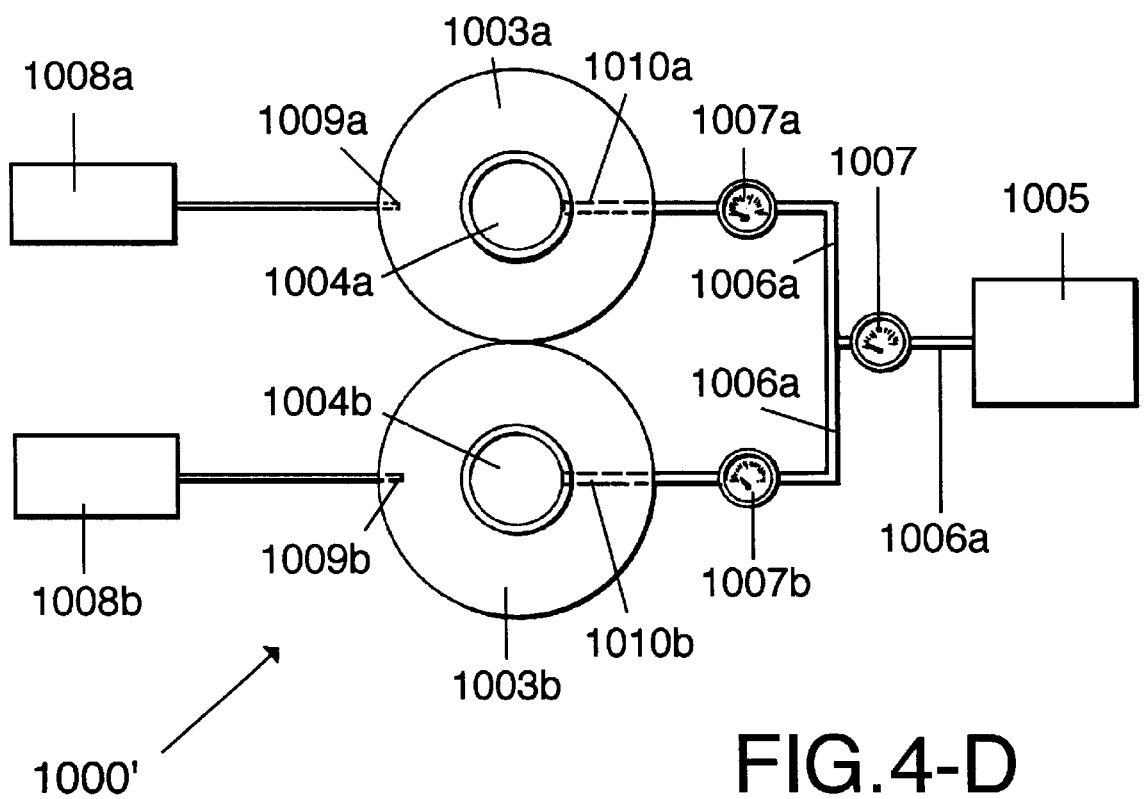
FIG.4-D

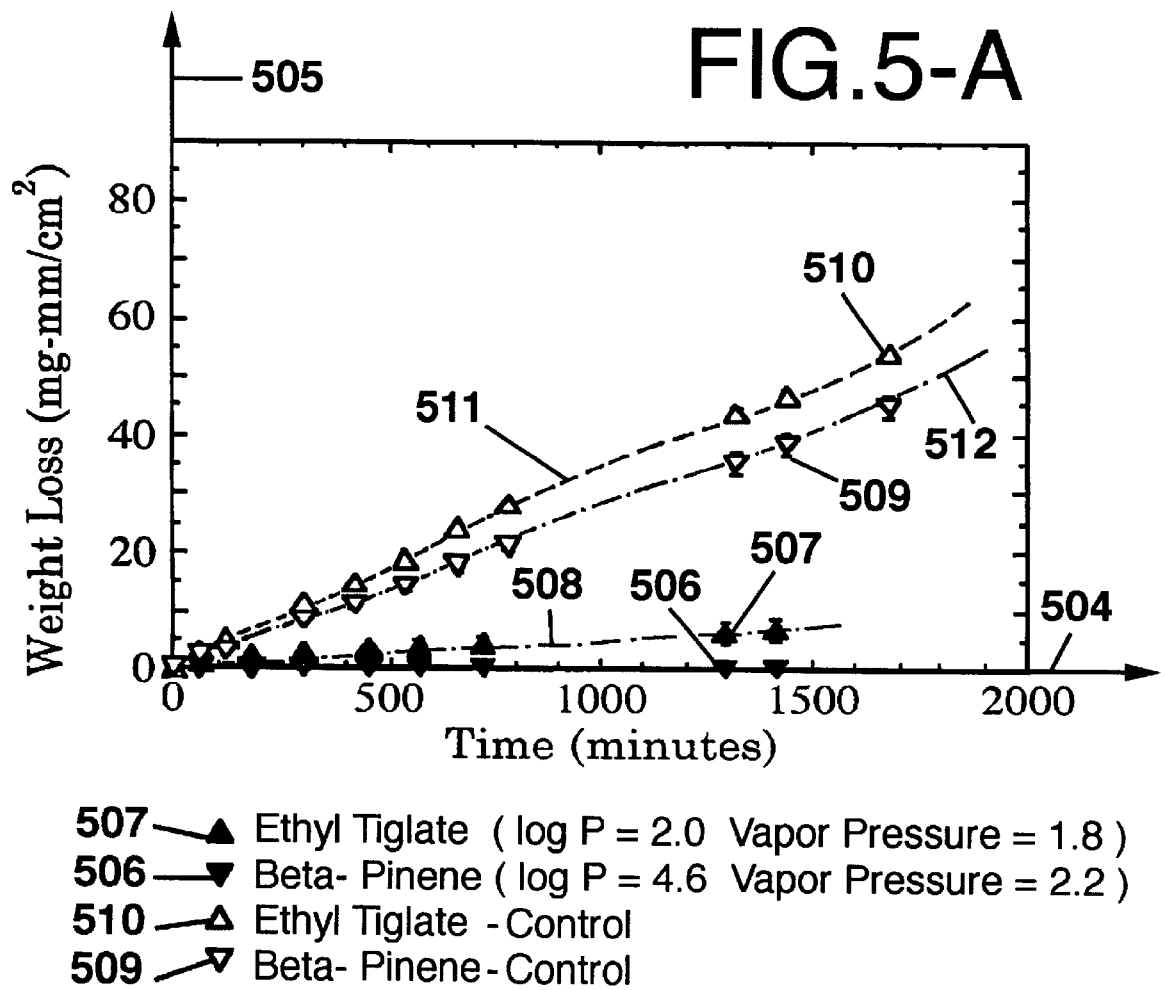

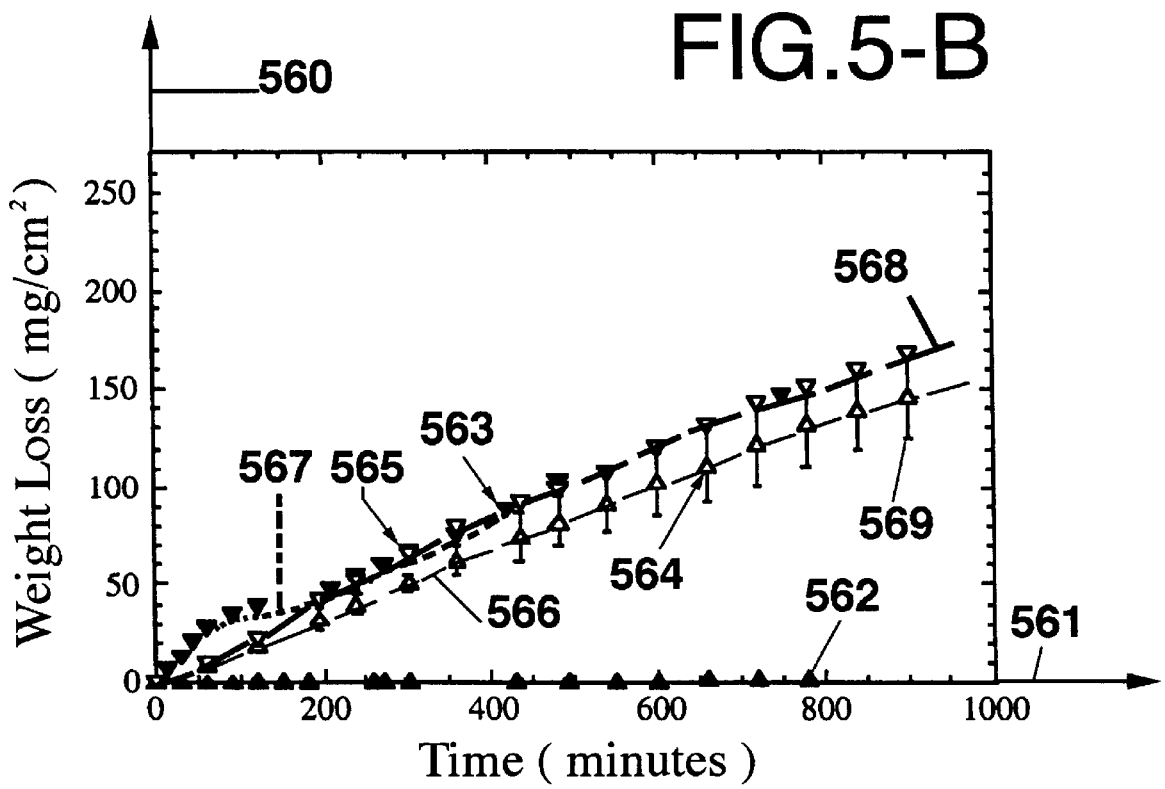
562 — ▲ Beta-Pinene ( log P = 4.6  Vapor Pressure = 2.2 )
564 — △ Beta-Pinene ( log P = 4.6  Vapor Pressure = 2.2 )-Evaporation, No Polymer.
563 — ▼ Ethyl Tiglate ( log P = 2.0  Vapor Pressure = 1.8 )
565 — ▽ Ethyl Tiglate ( log P = 2.0  Vapor Pressure = 1.8 )-Evaporation, No Polymer.

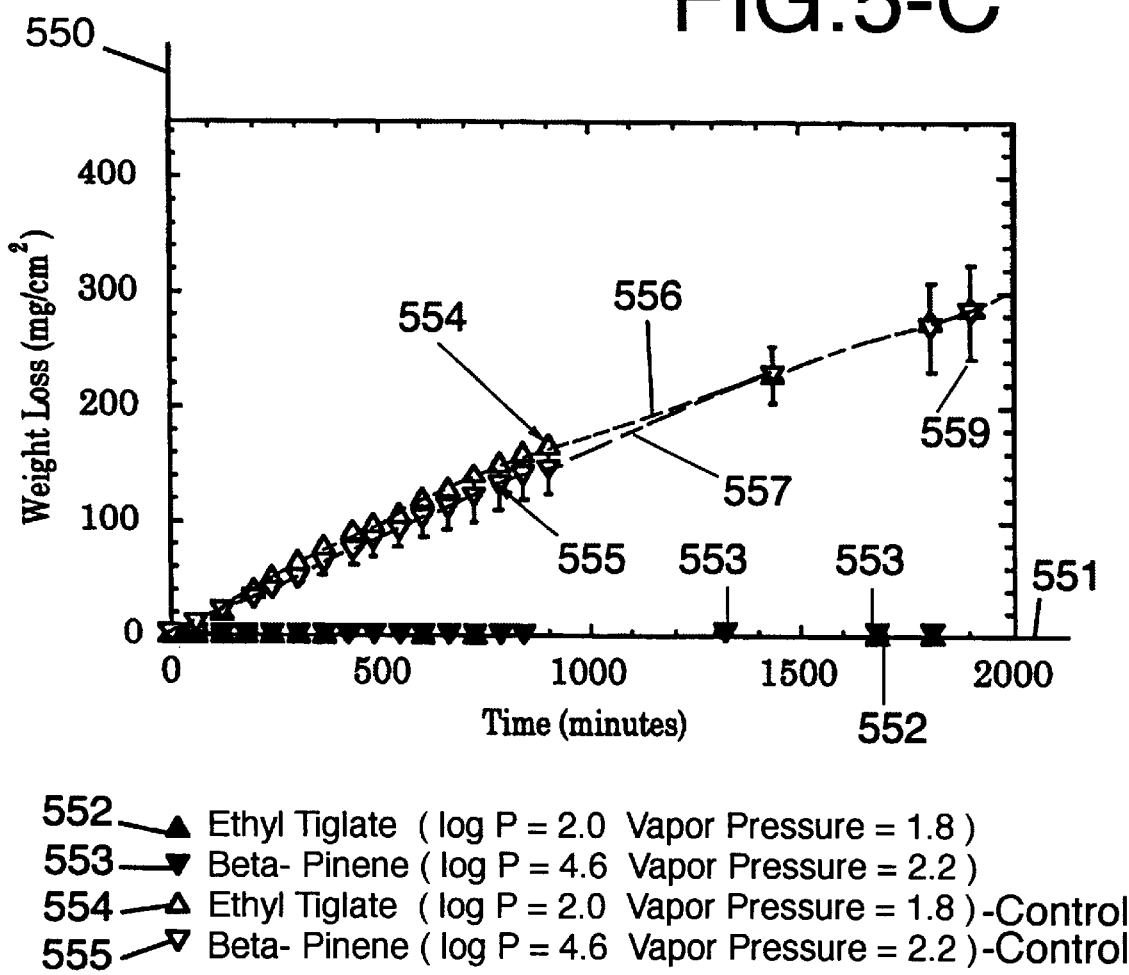

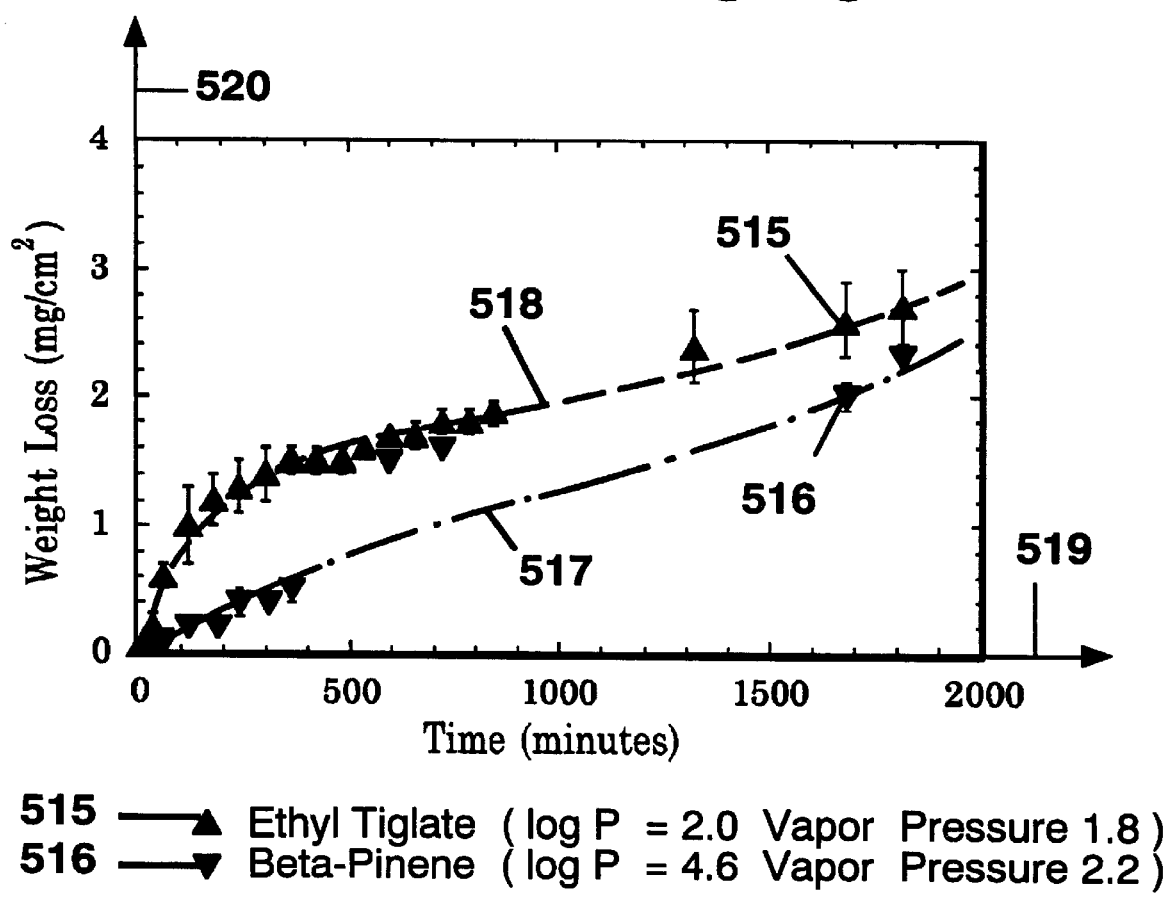

FIG. 5-E
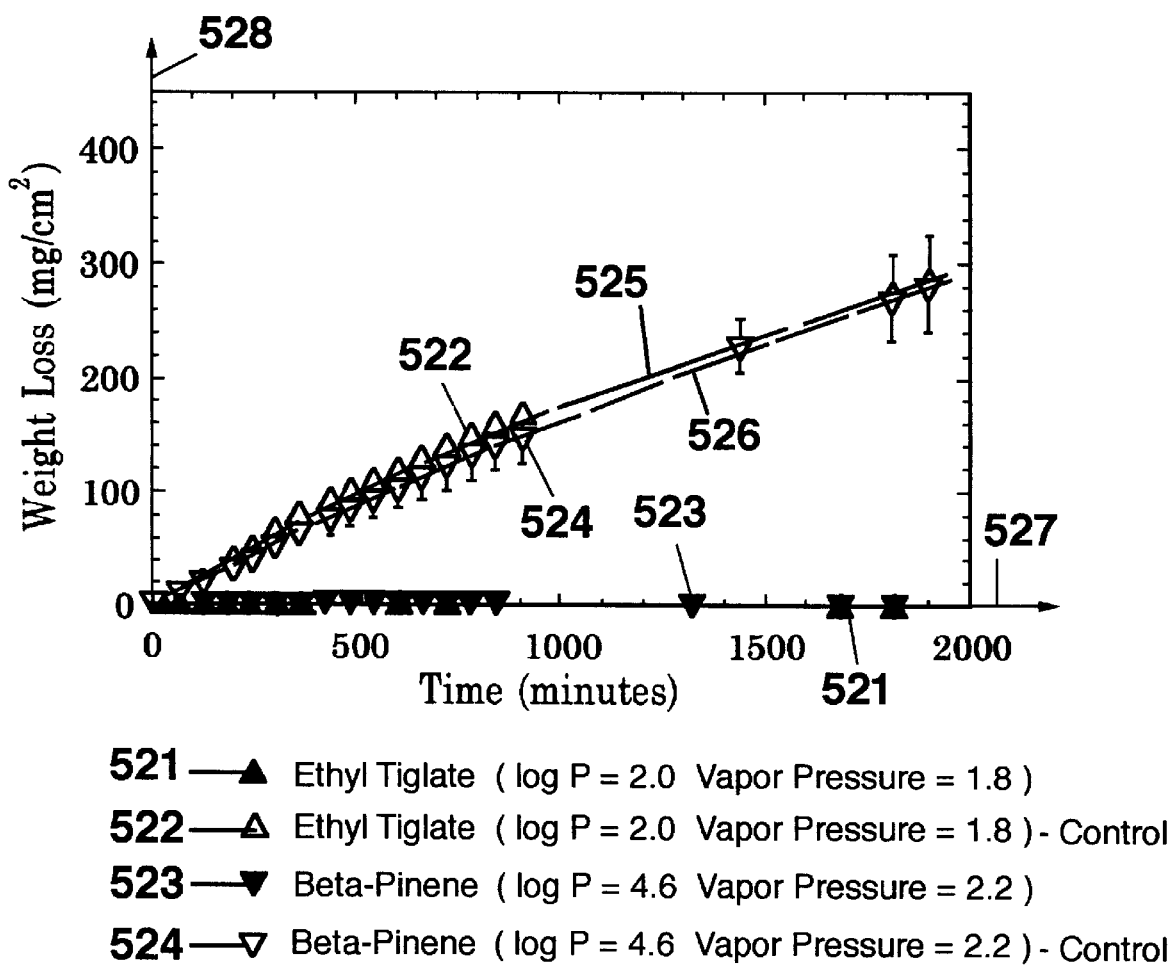
521 —▲ Ethyl Tiglate ( log P = 2.0  Vapor Pressure = 1.8 )
522 —△ Ethyl Tiglate ( log P = 2.0  Vapor Pressure = 1.8 ) - Control
523 —▼ Beta-Pinene ( log P = 4.6  Vapor Pressure = 2.2 )
524 —▽ Beta-Pinene ( log P = 4.6  Vapor Pressure = 2.2 ) - Control

FIG. 5-F
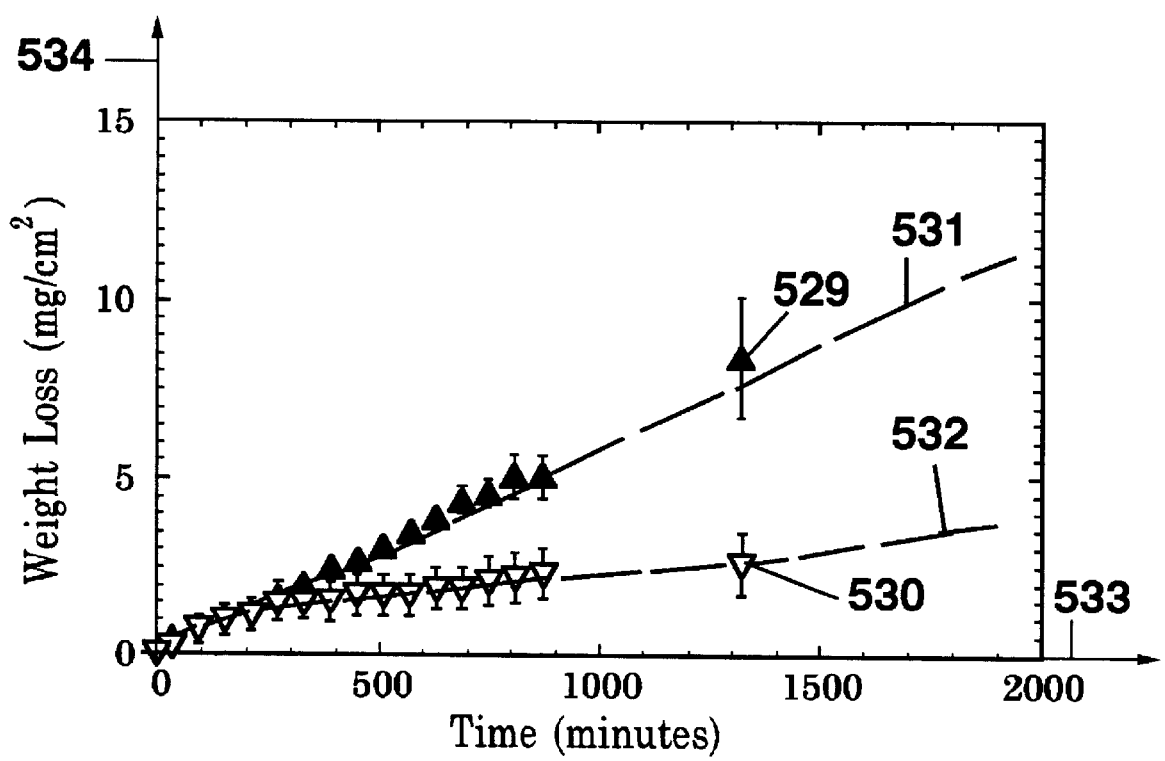
529 —▲— Ethyl Tiglate ( log P = 2.0   Vapor Pressure = 1.8 )
530 —▽— Beta-Pinene ( log P = 4.6   Vapor Pressure = 2.2 )

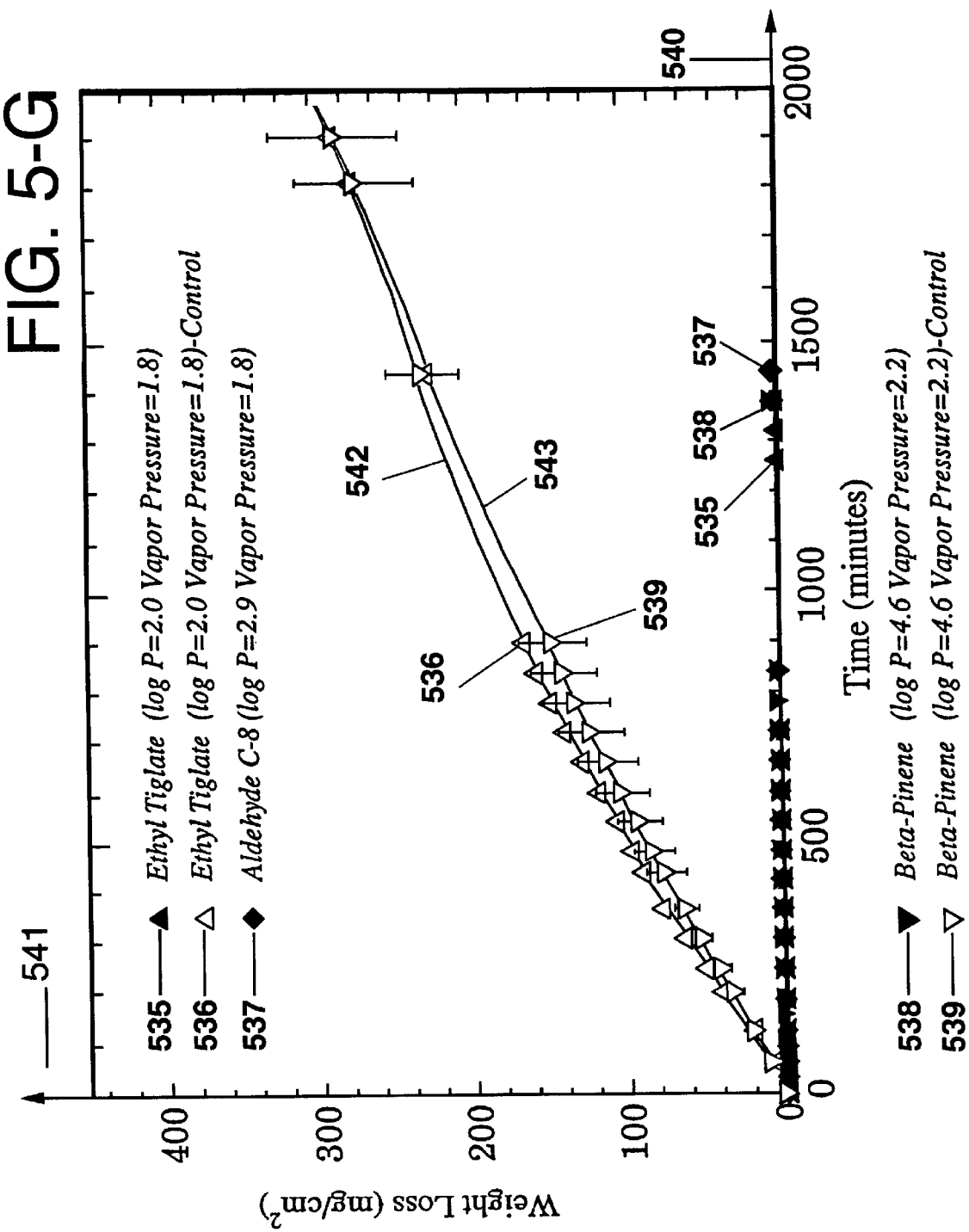

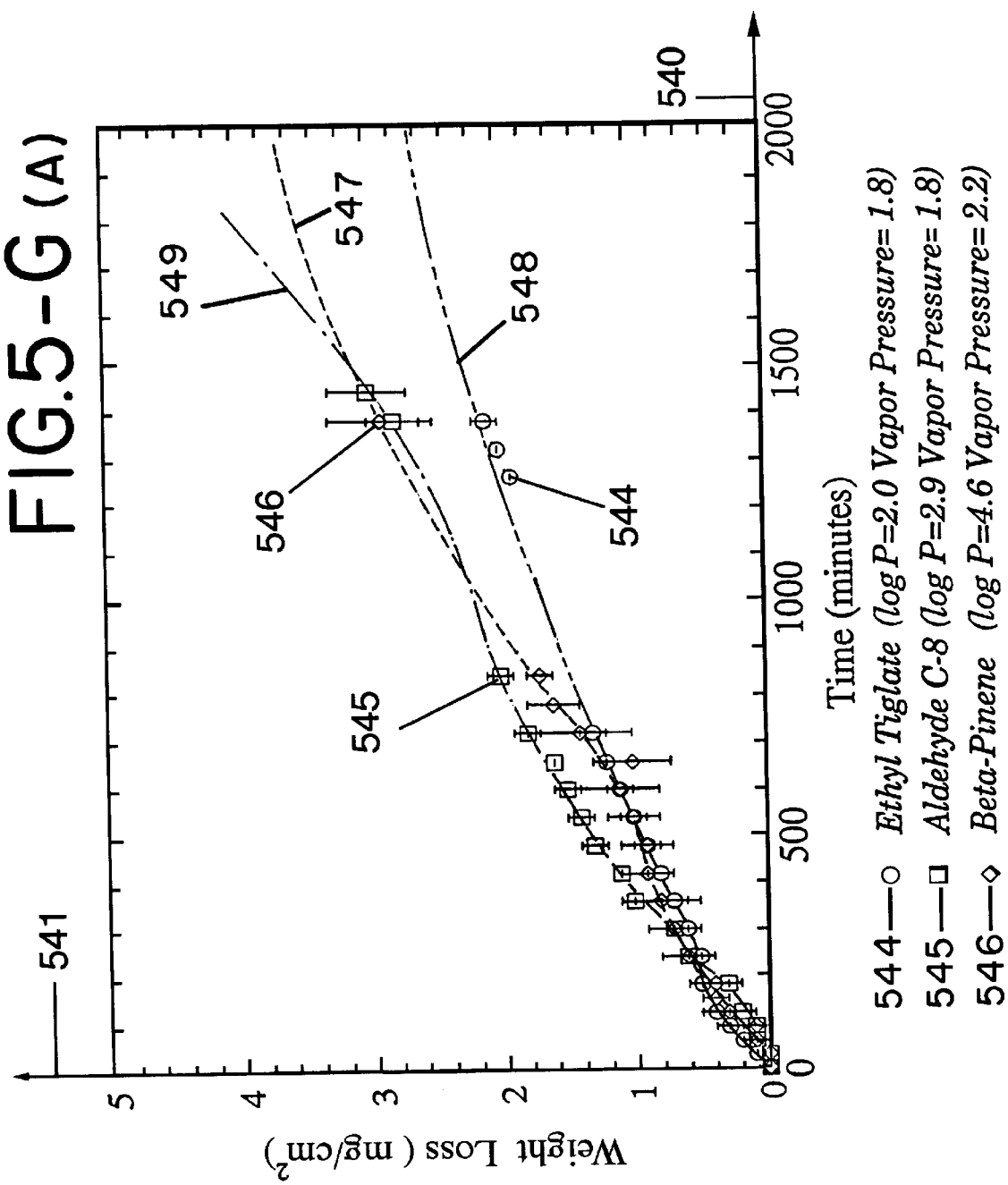

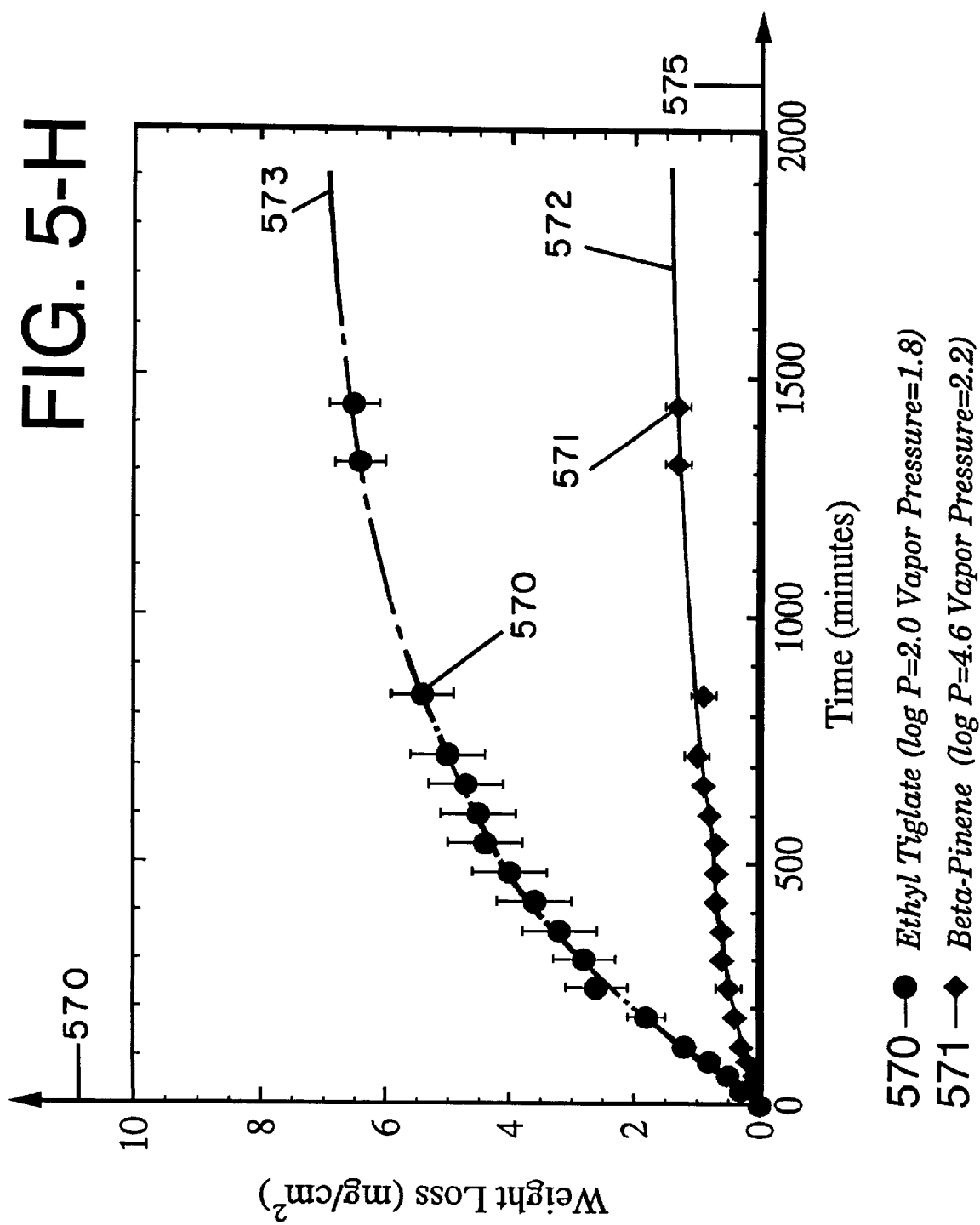

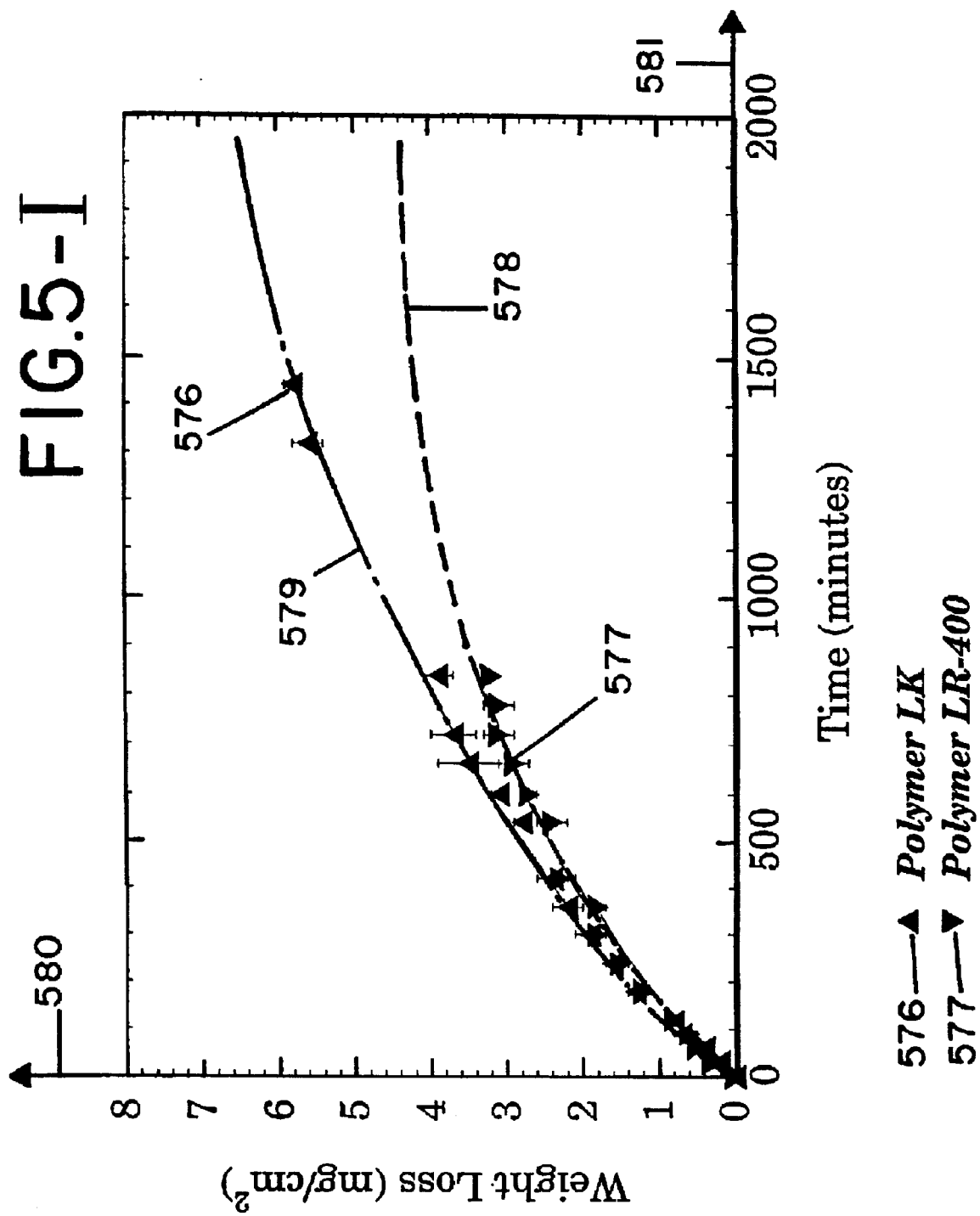

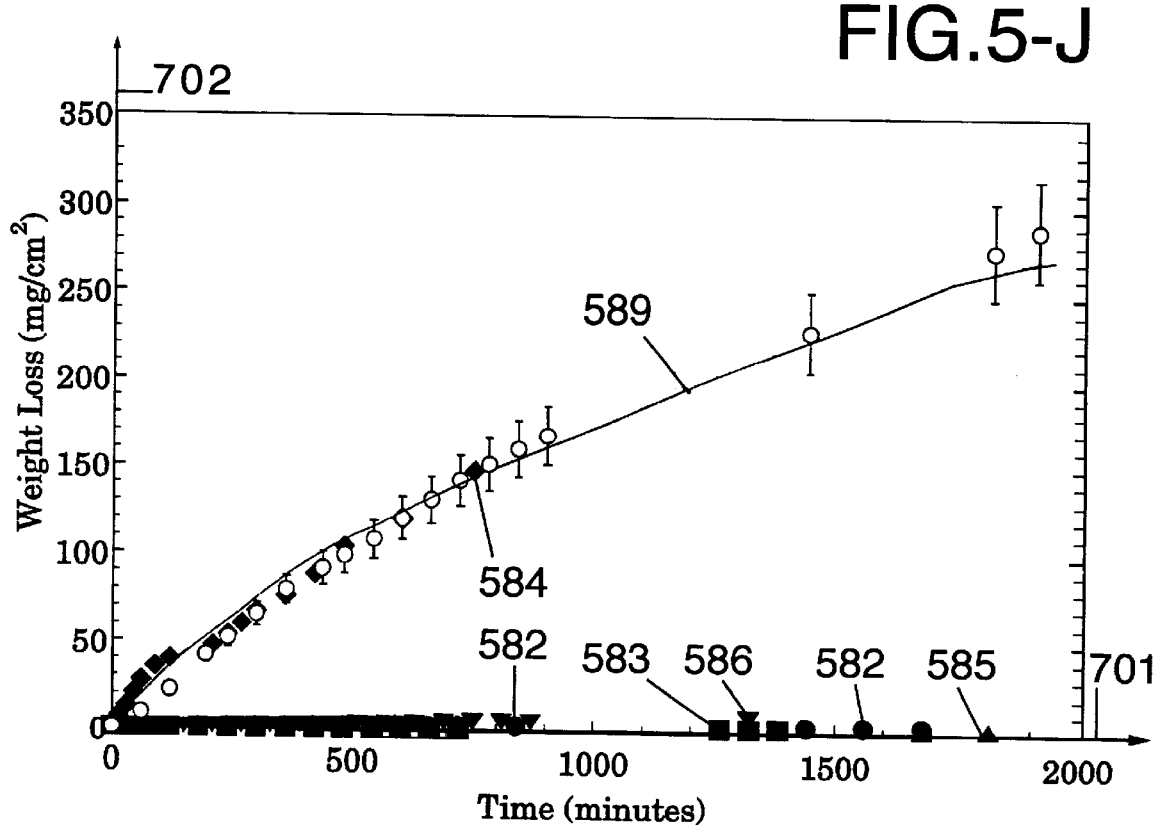
FIG.5-J
582 ● Gelatin
583 ■ Carboxymethyl Cellulose
584 ♦ Hydroxypropyl Cellulose
585 ▲ Poly(vinyl alcohol), 98% Hydrolyzed
586 ▼ Poly(vinyl alcohol), 74% Hydrolyzed
587 ○ Evaporation Rate-Control

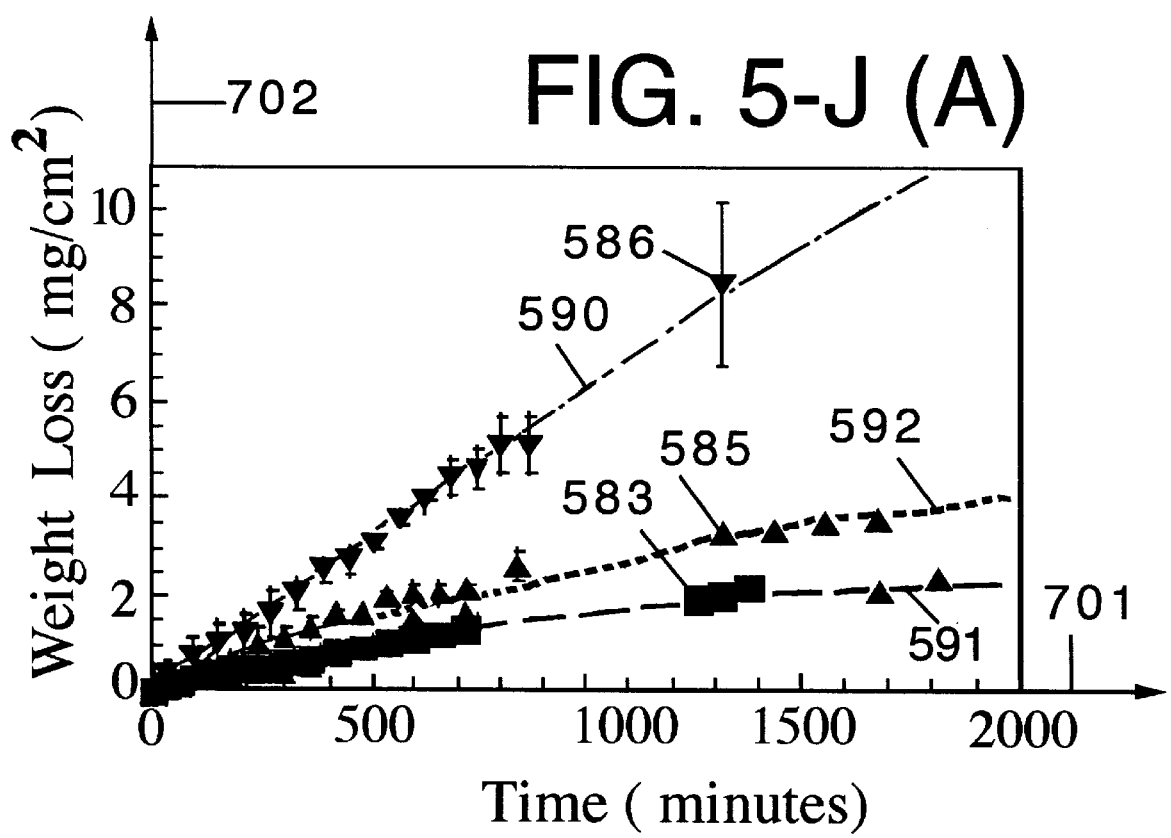

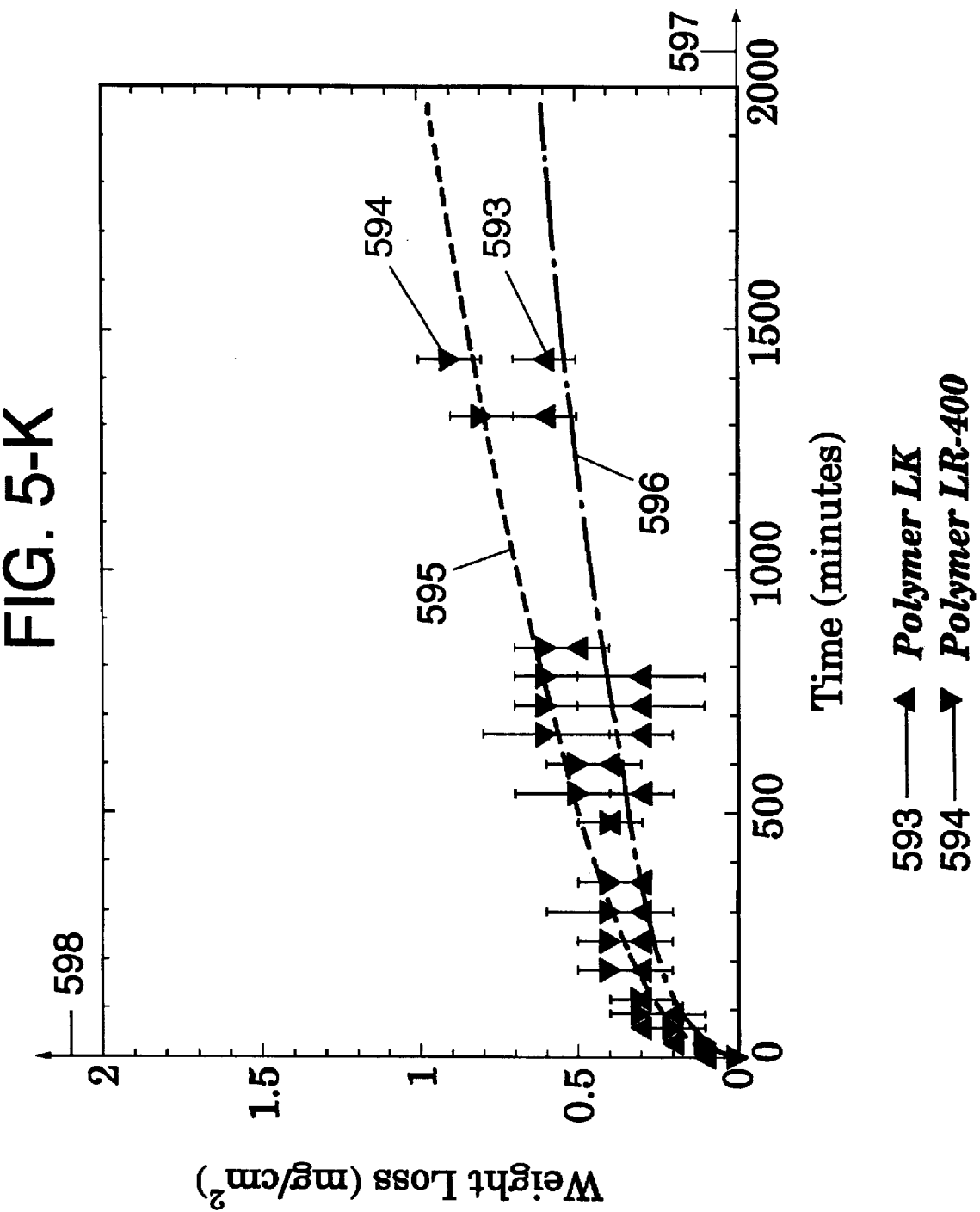

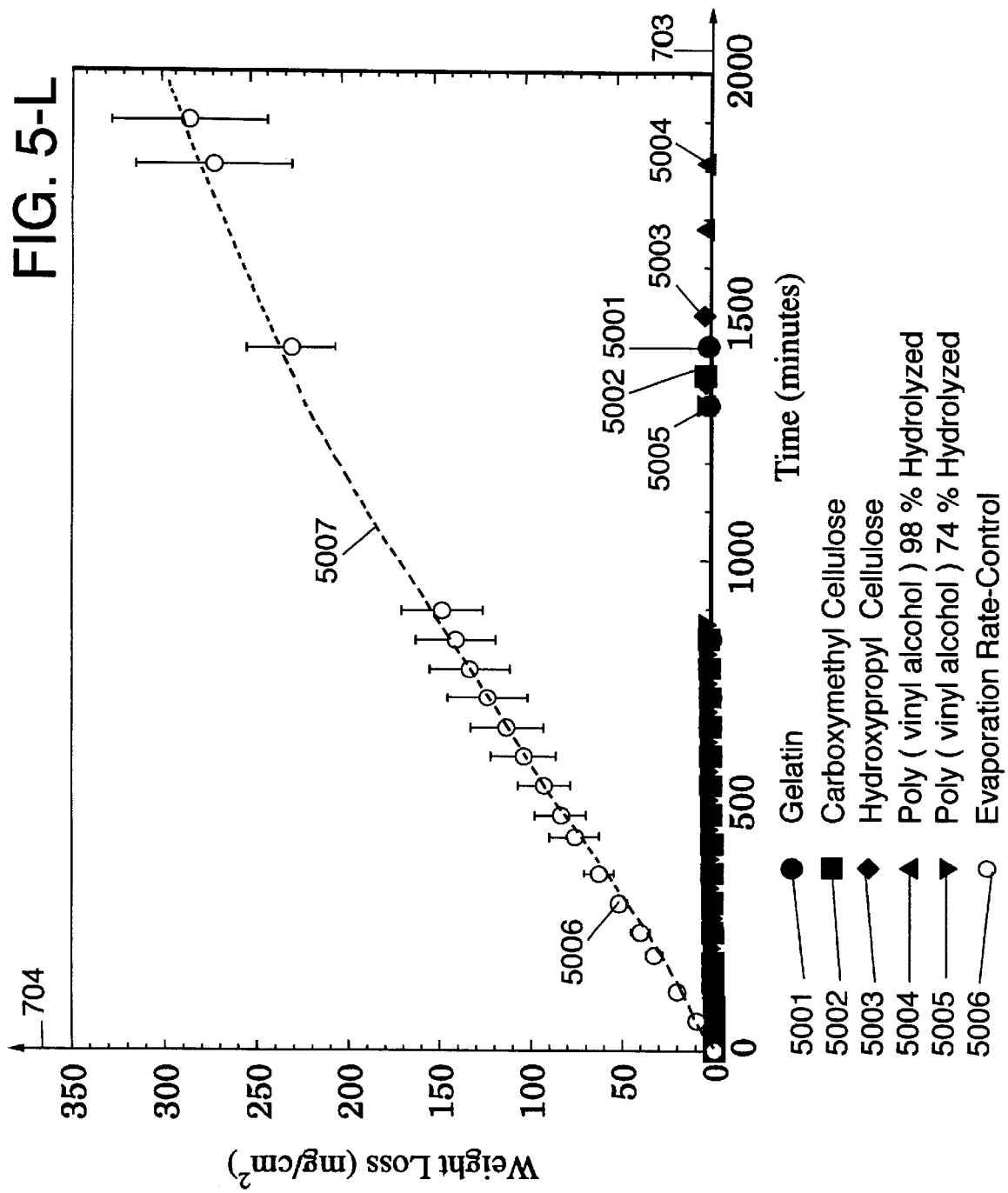

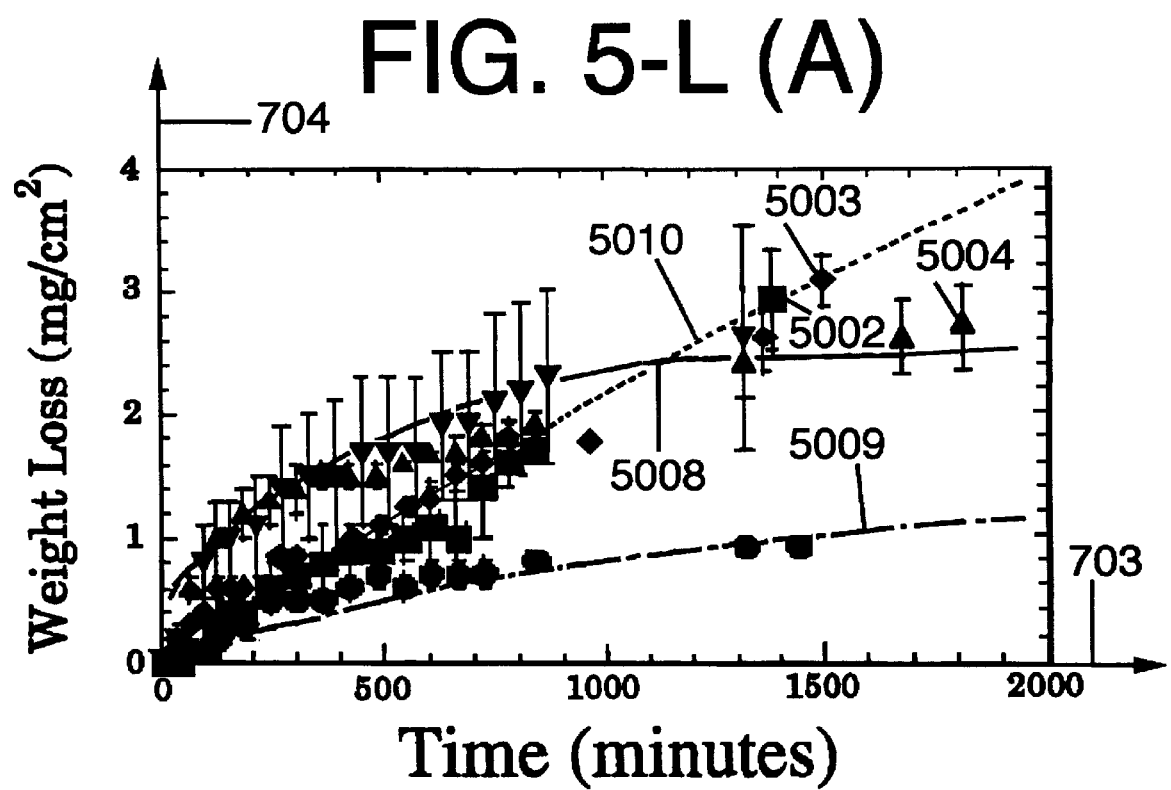

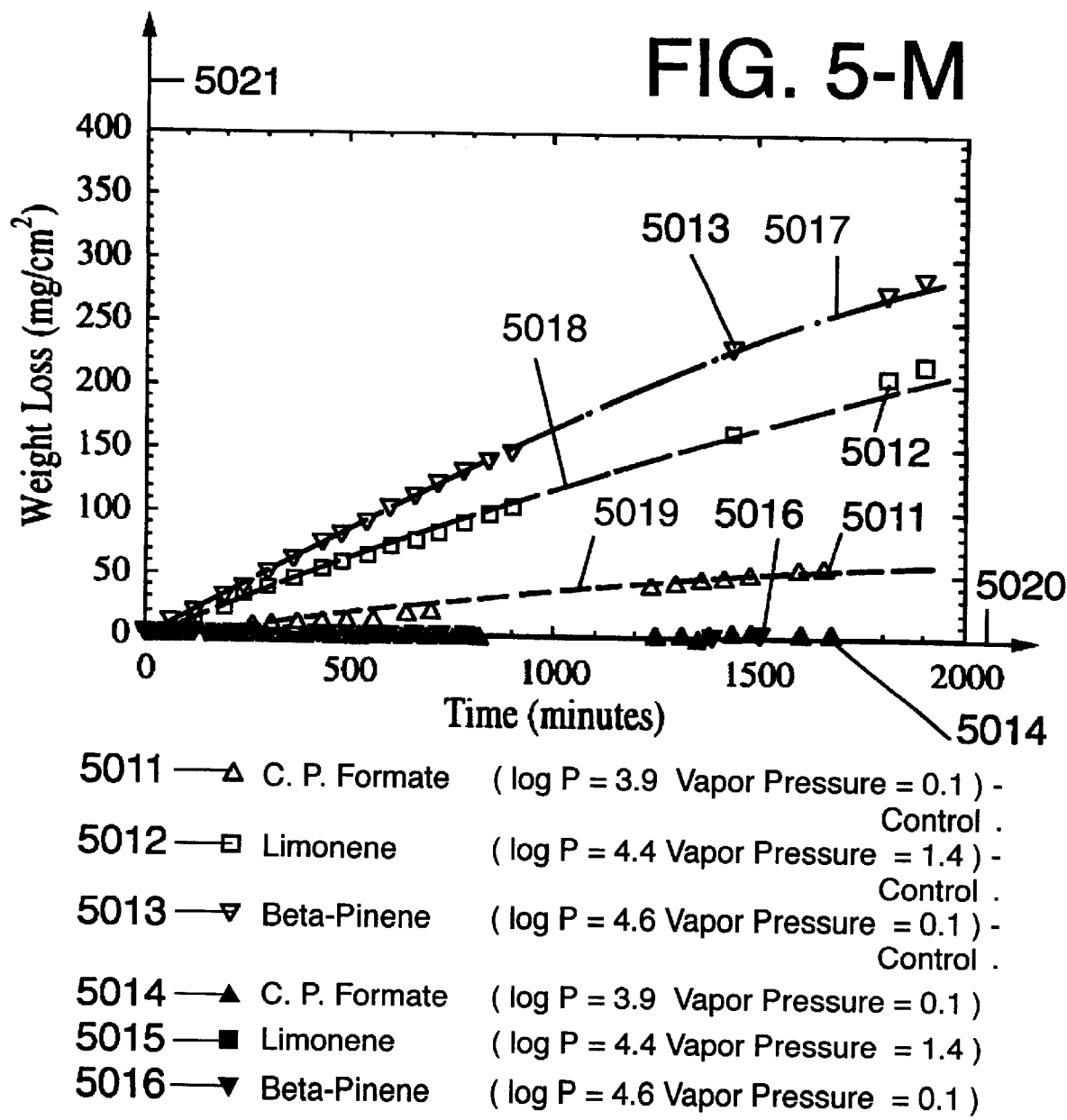
FIG. 5-M

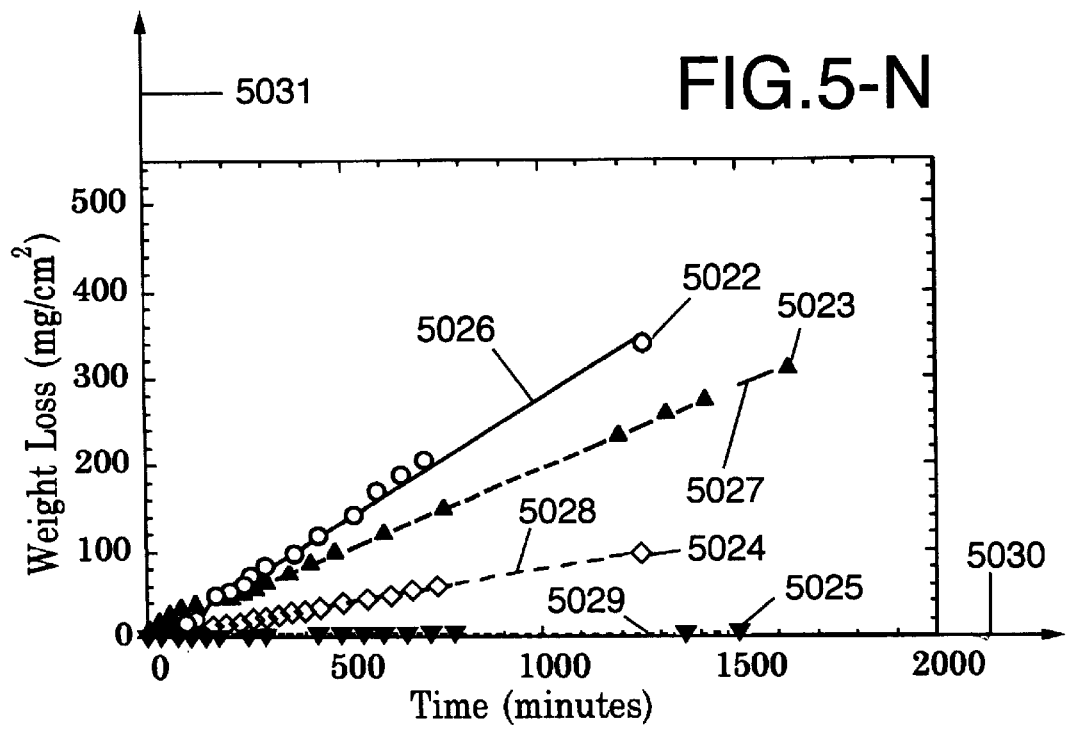
5022 —o— Prenyl Acetate ( log P = 1.7 Vapor Pressure = 1.9 )
5023 —▲— Ethyl Tiglate ( log P = 2.0 Vapor Pressure = 1.8 )
5024 —◇— Aldehyde C-8 ( log P = 2.9 Vapor Pressure = 1.8 )
5025 —▼— Beta- Pinene ( log P = 4.6 Vapor Pressure = 2.2 )

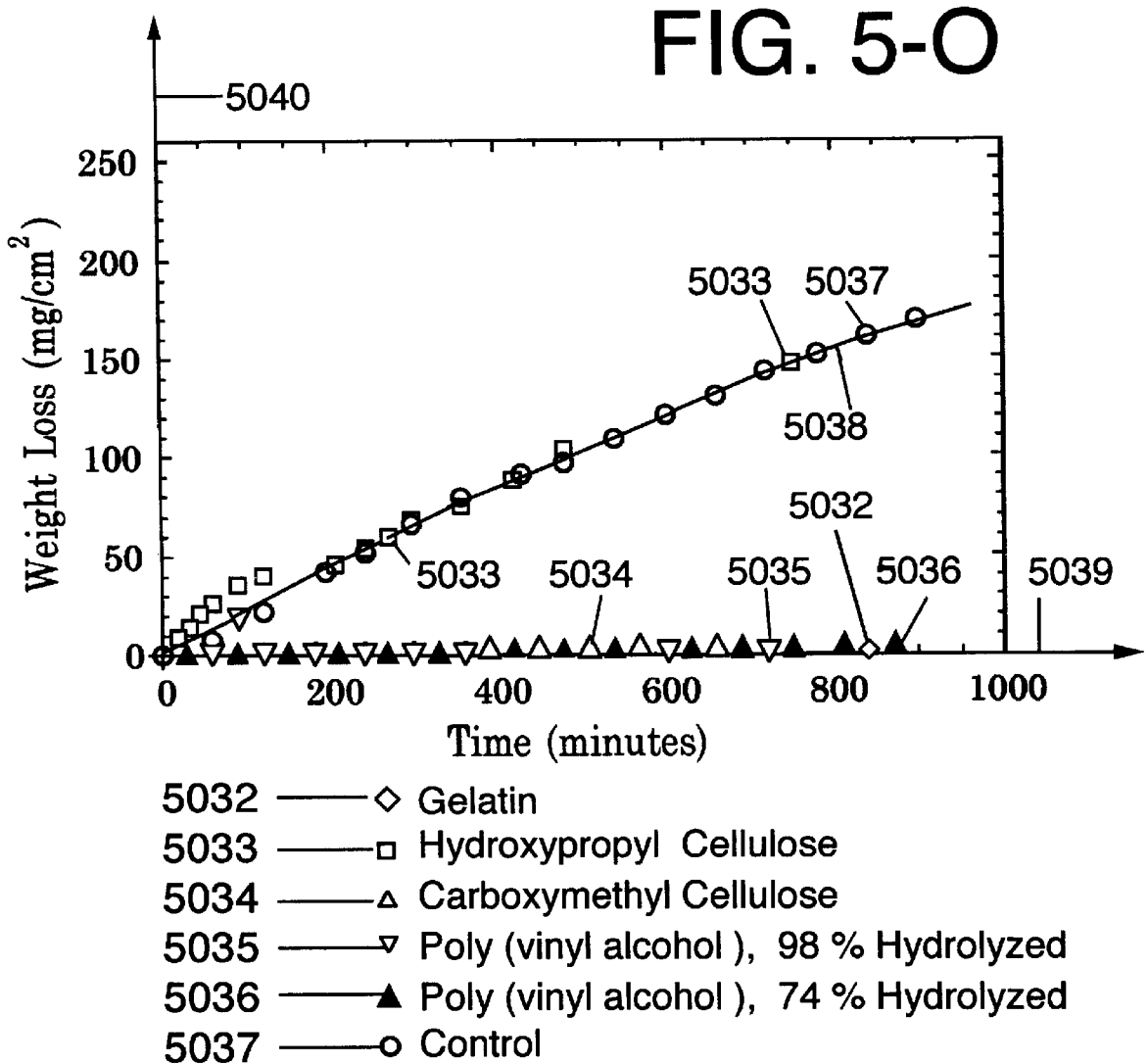

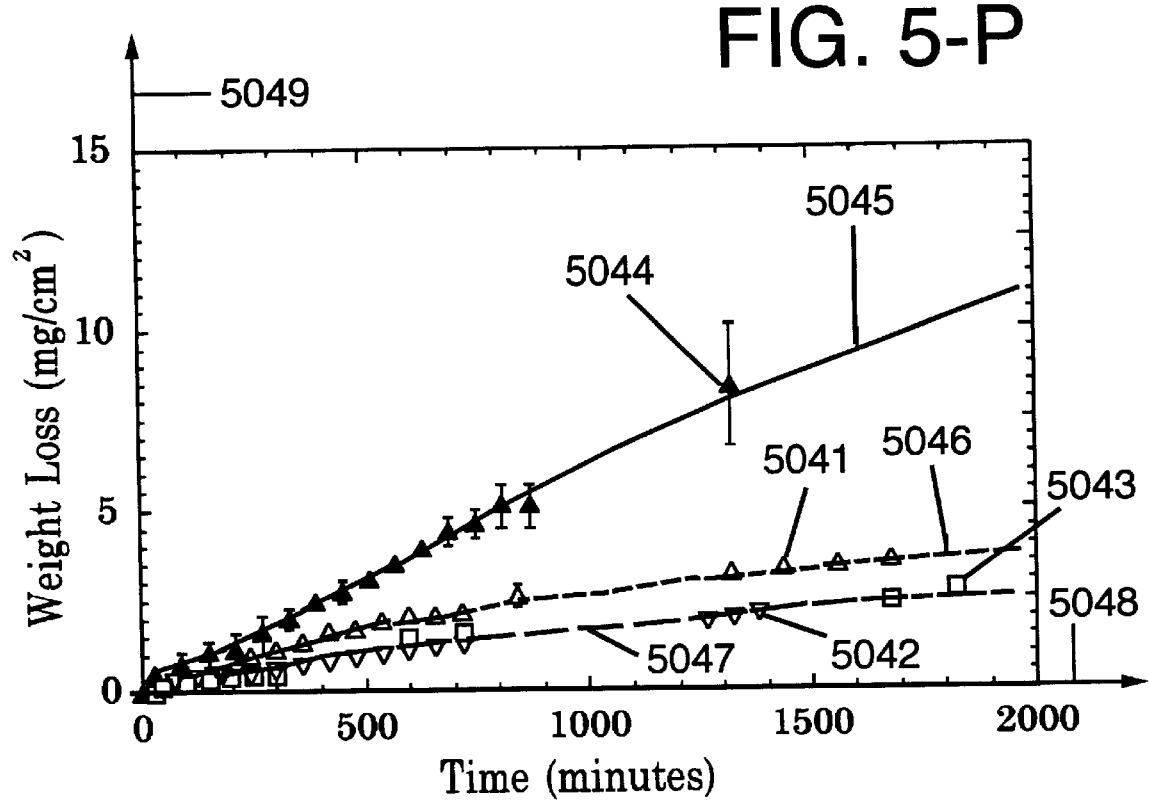
FIG. 5-P
5041 —△— Gelatin
5042 —▽— Carboxymethyl Cellulosse
5043 —□— Poly(vinyl alcohol), 98 % Hydrolyzed
5044 —▲— Poly(vinyl alcohol), 74 % Hydrolyzed

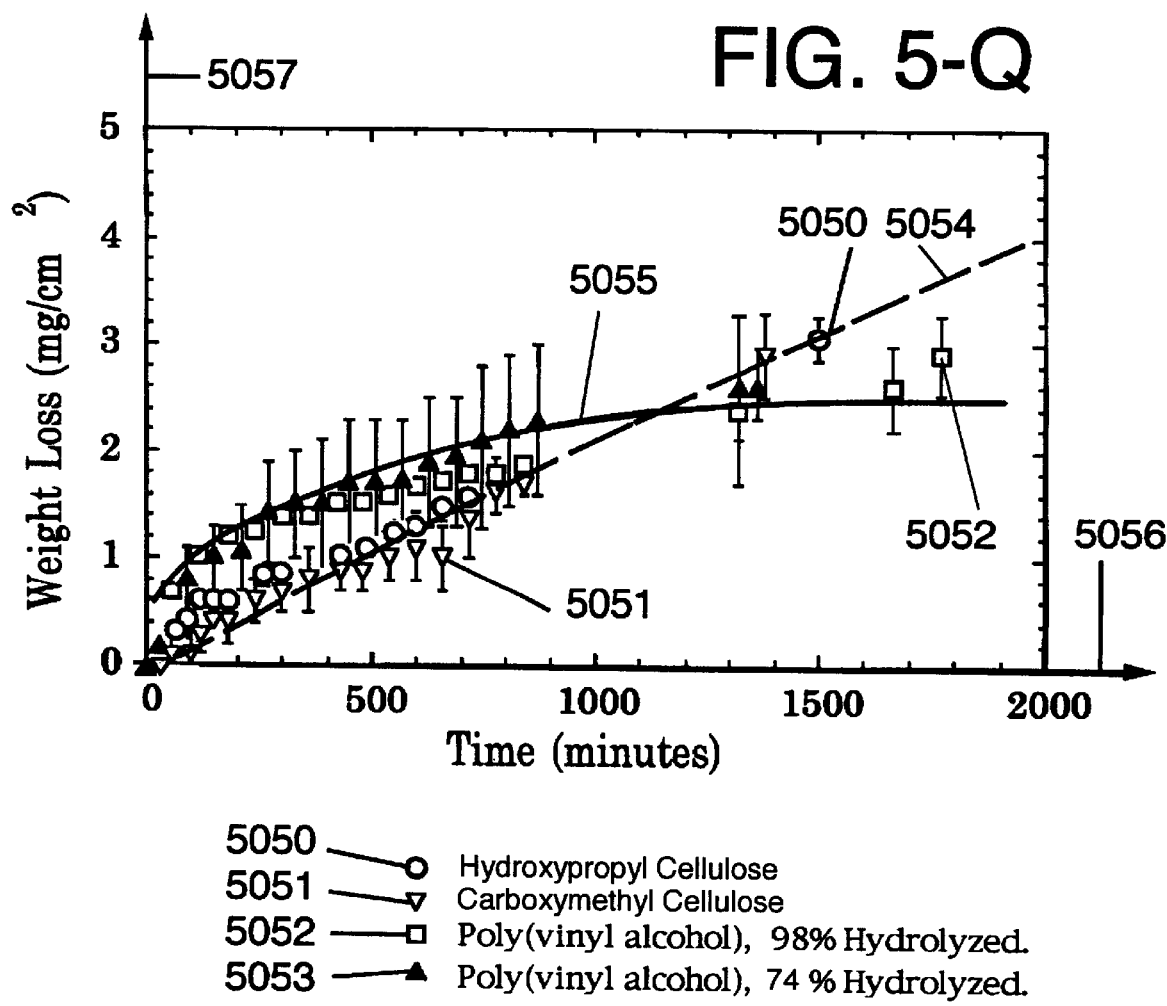

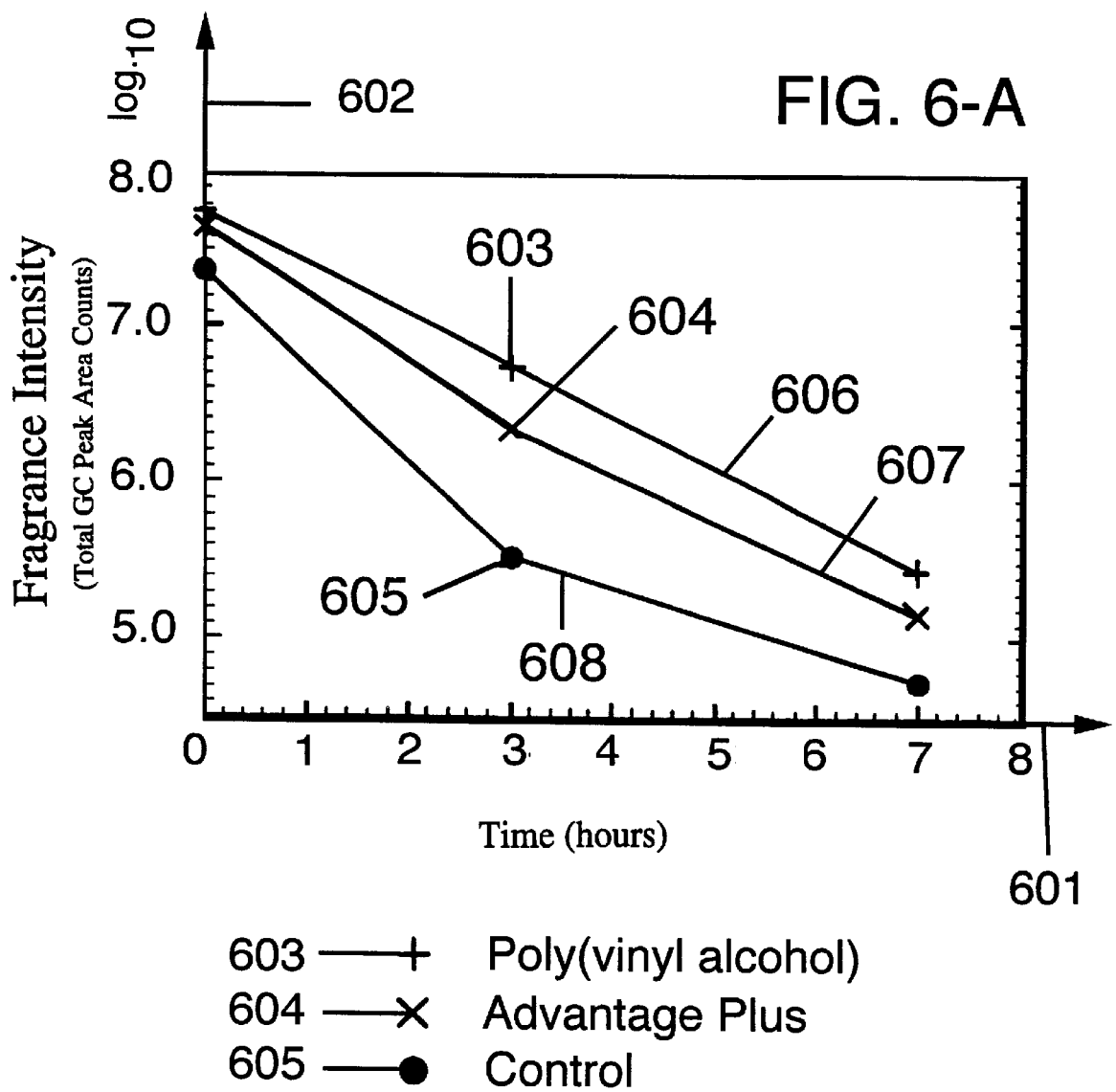

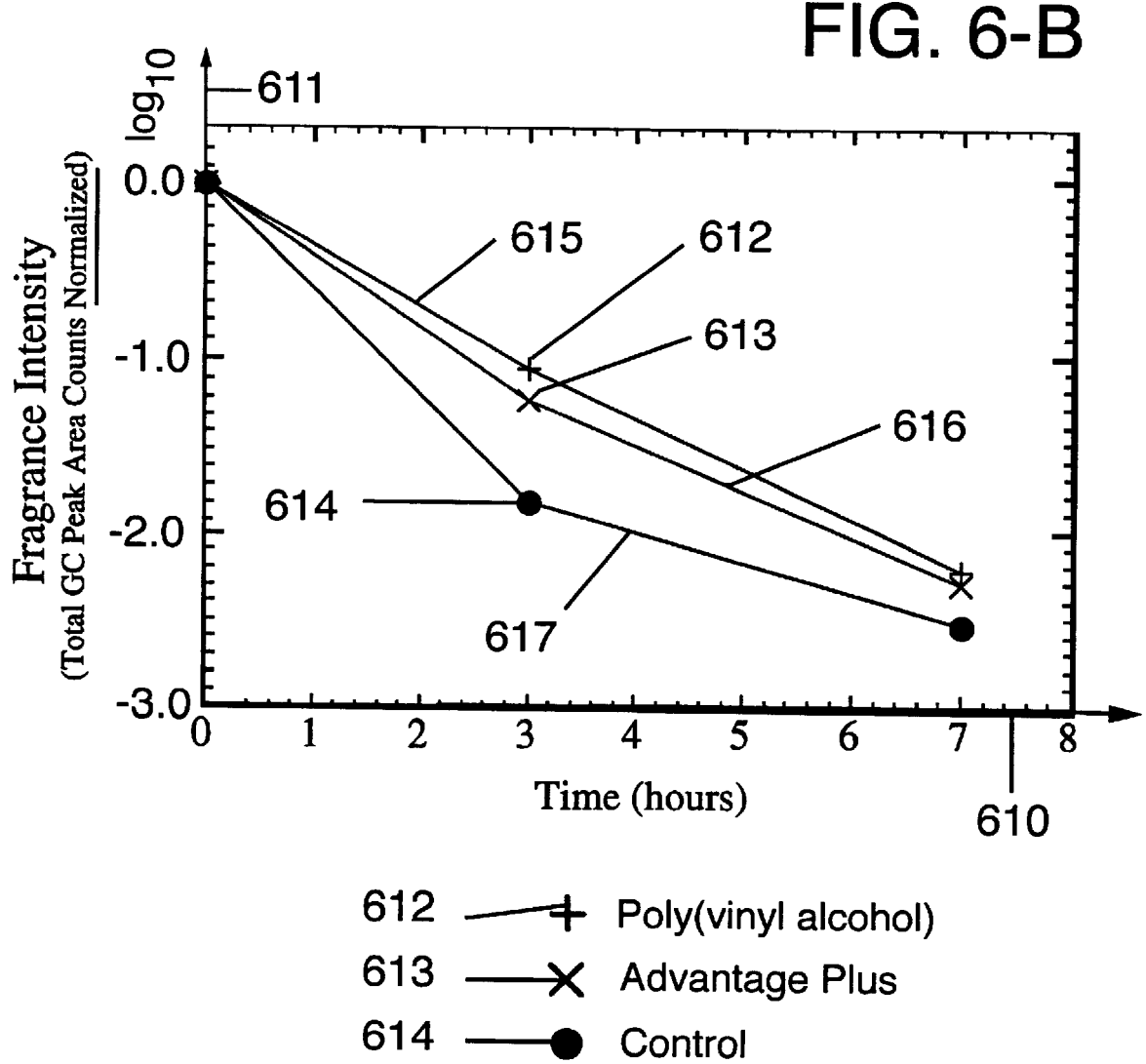

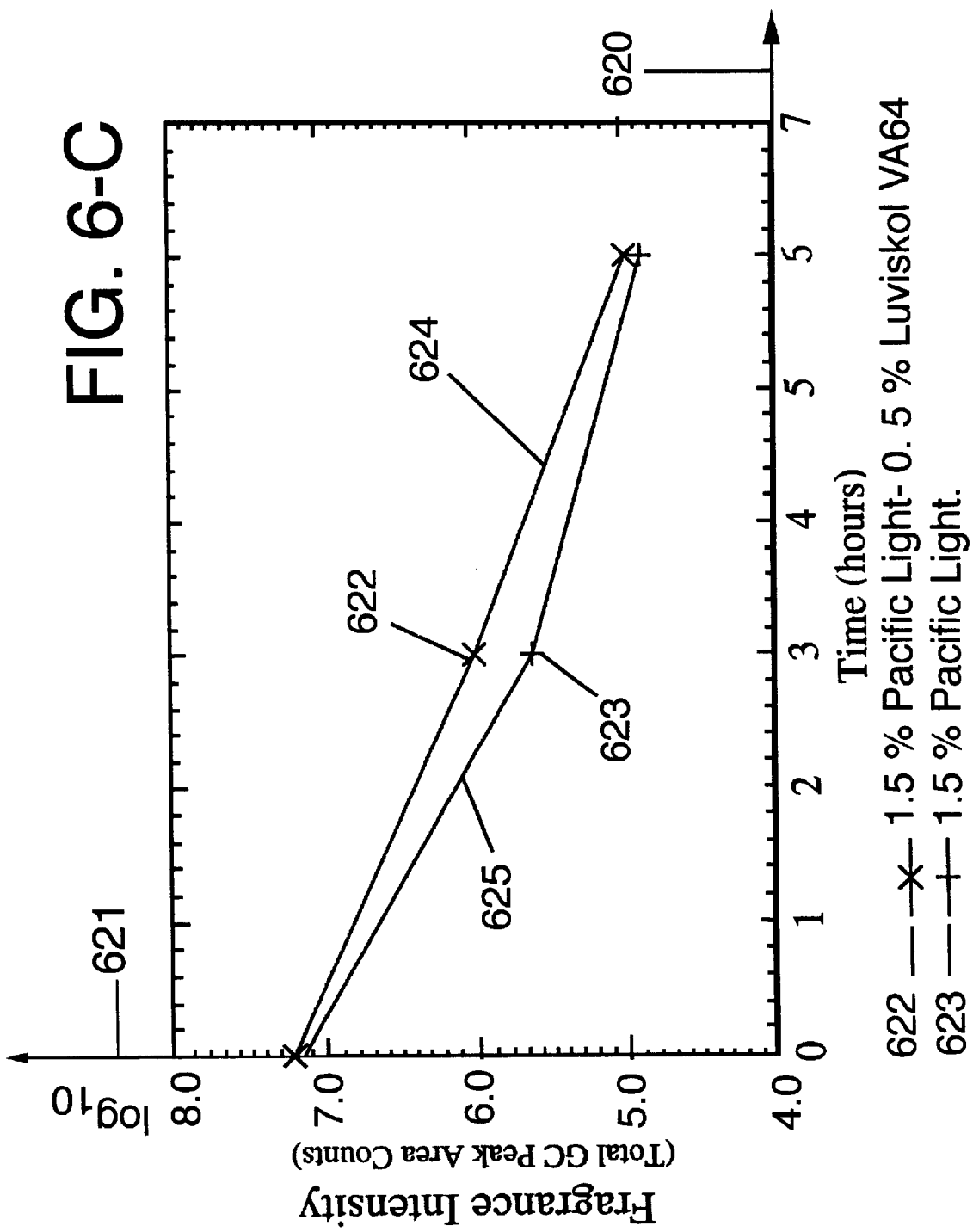

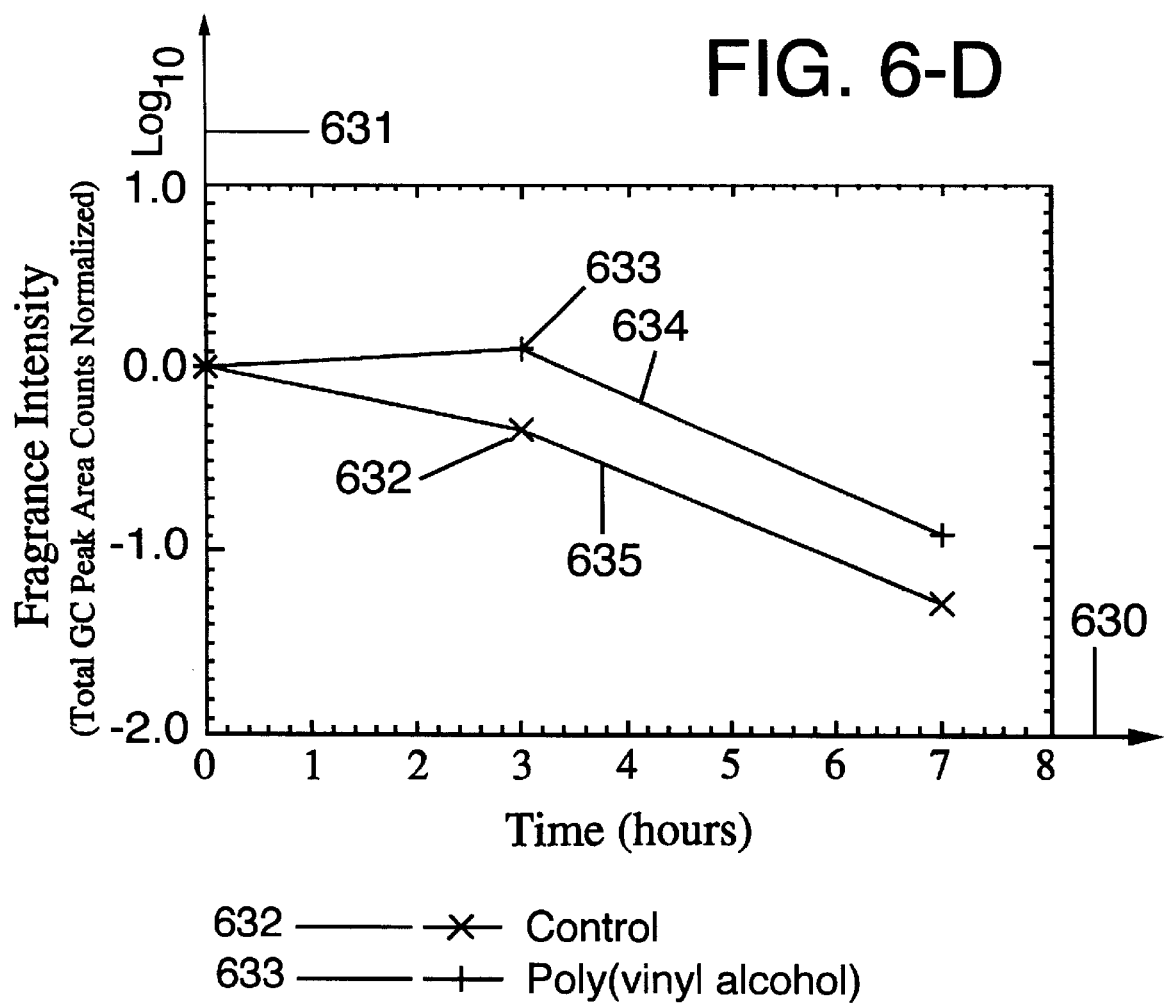

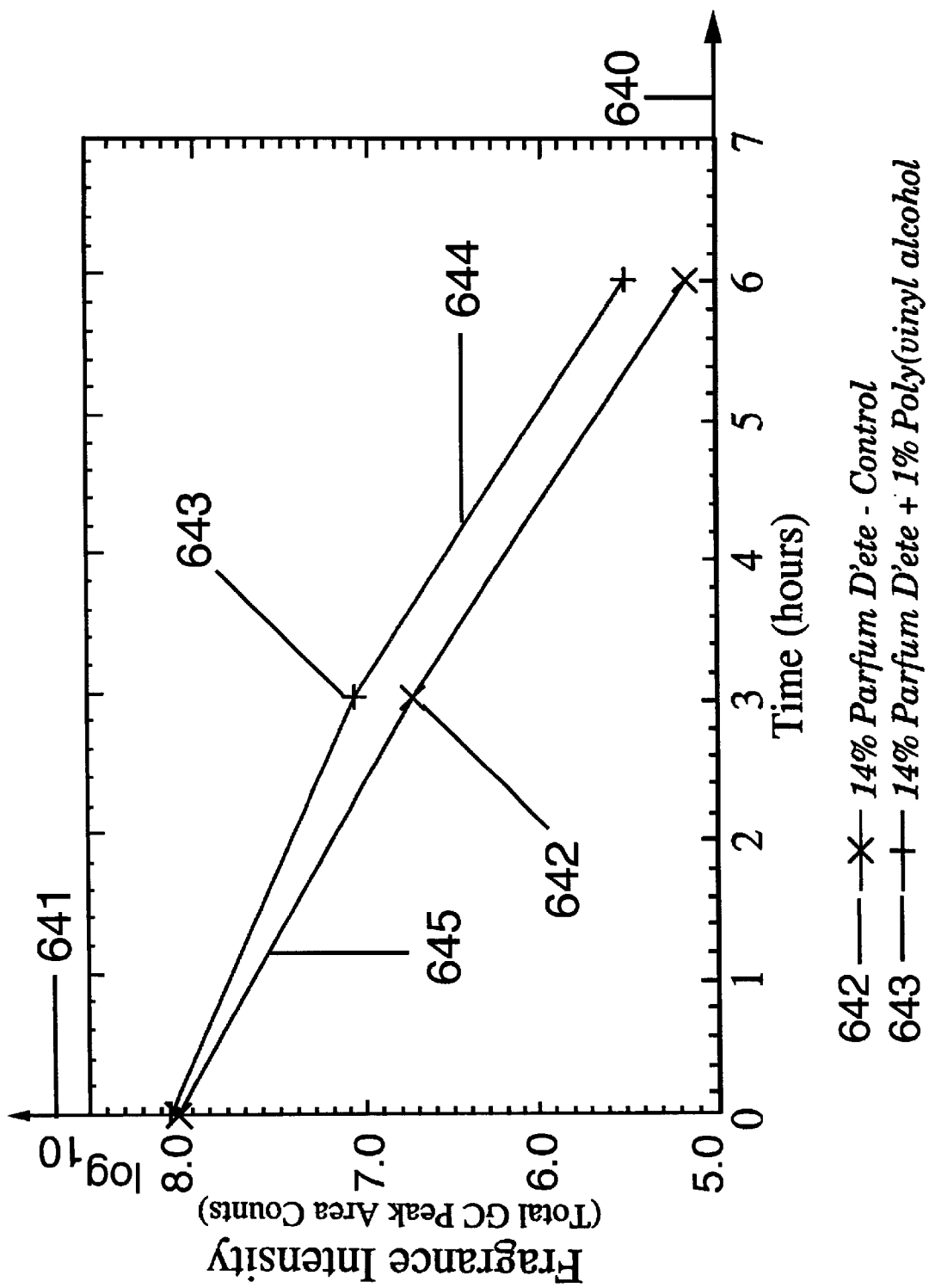

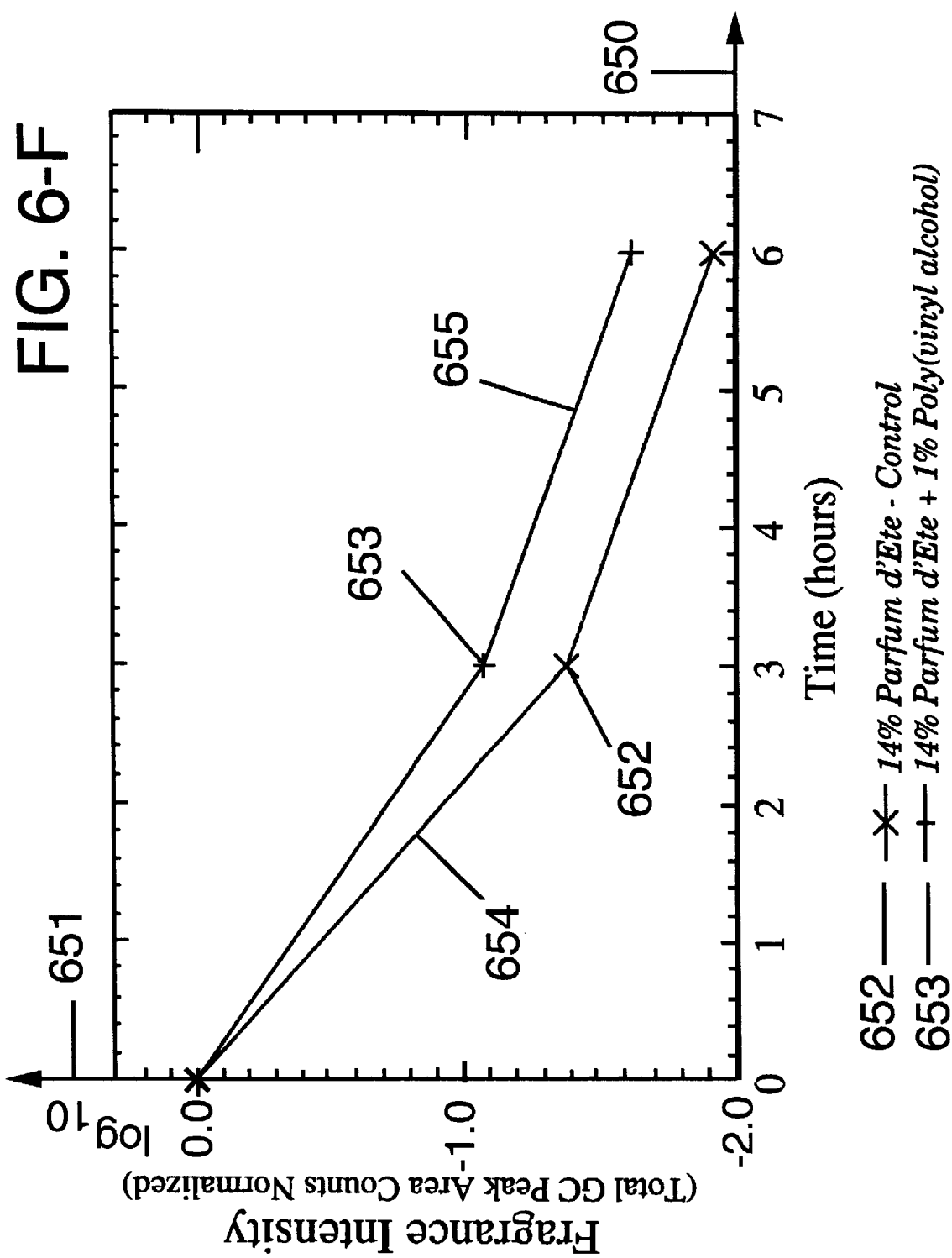

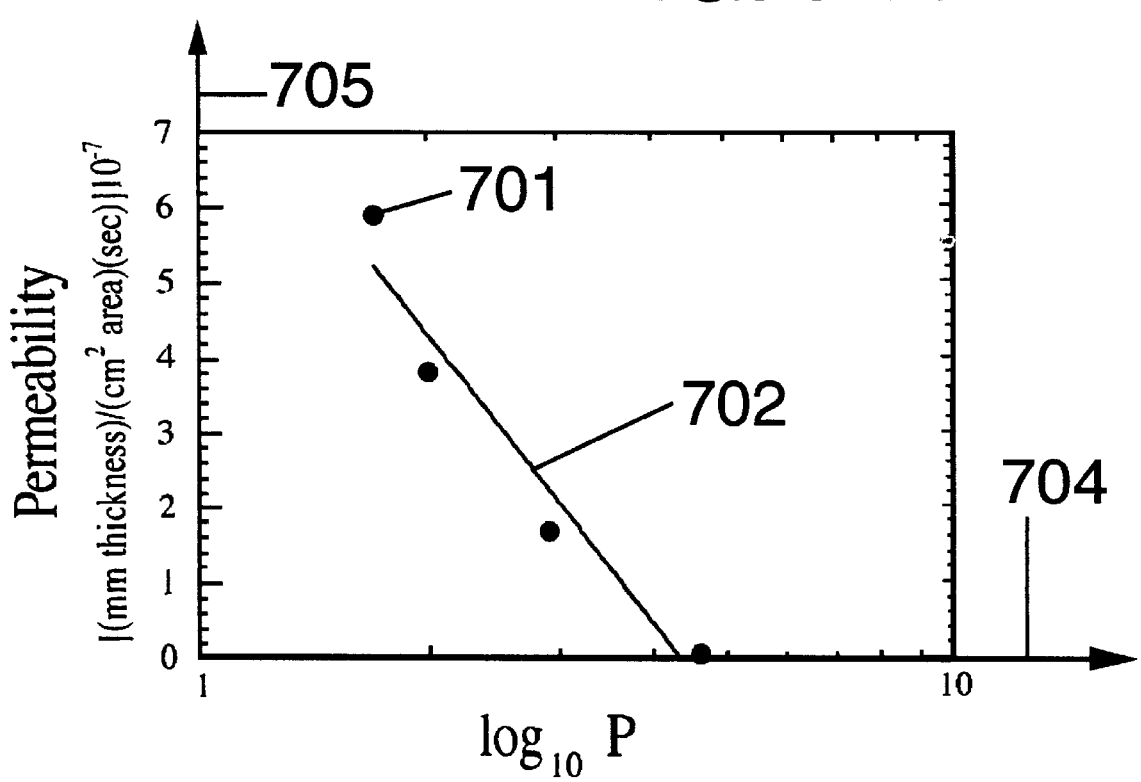

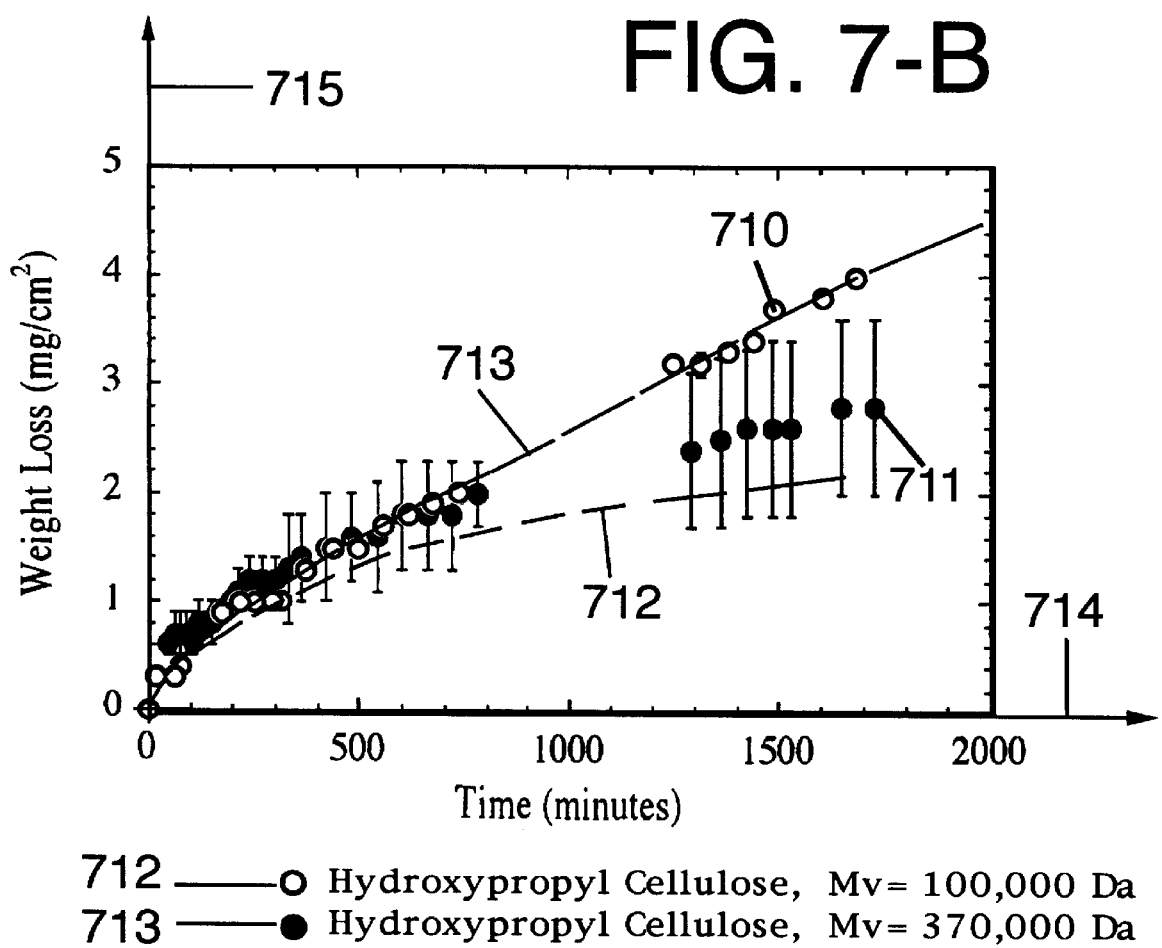

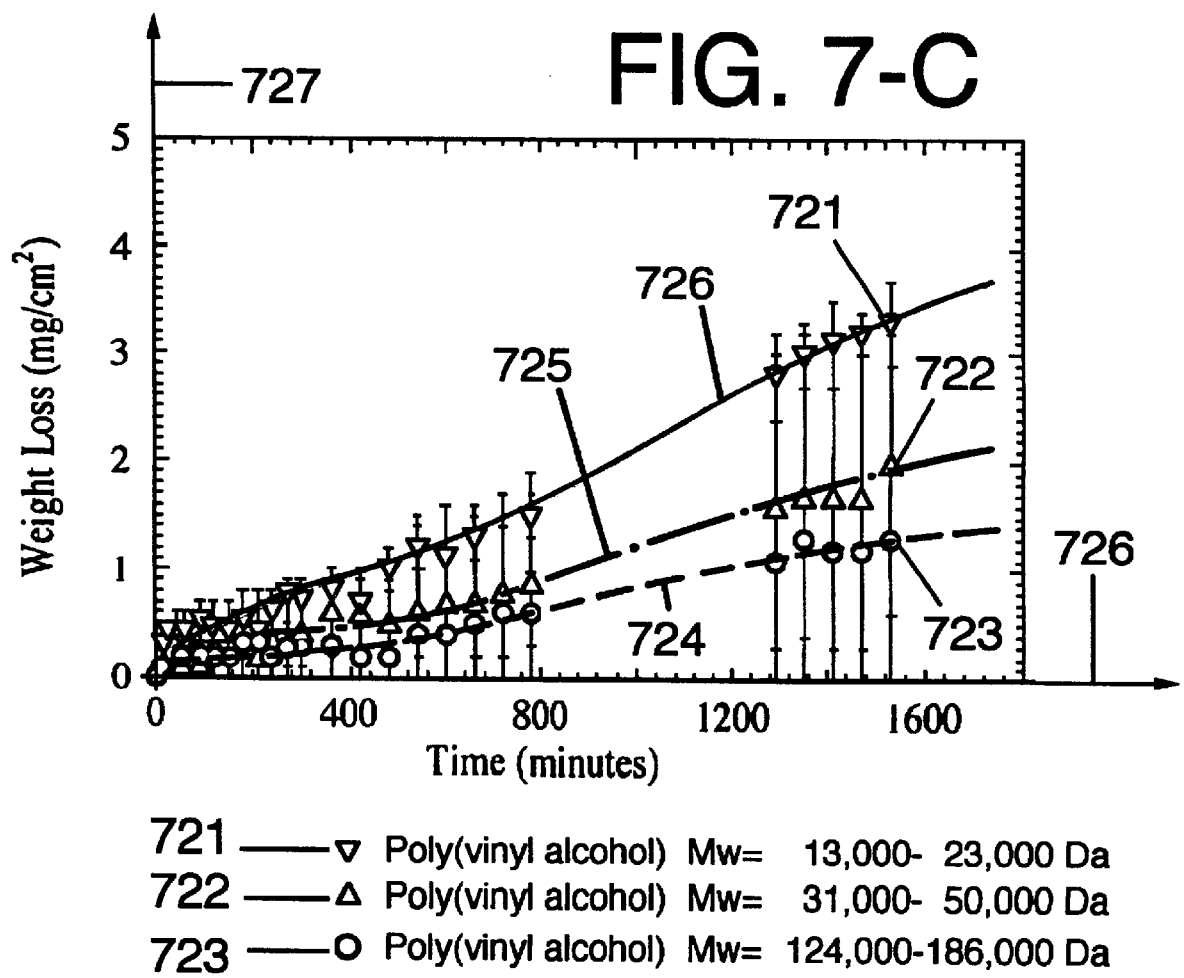

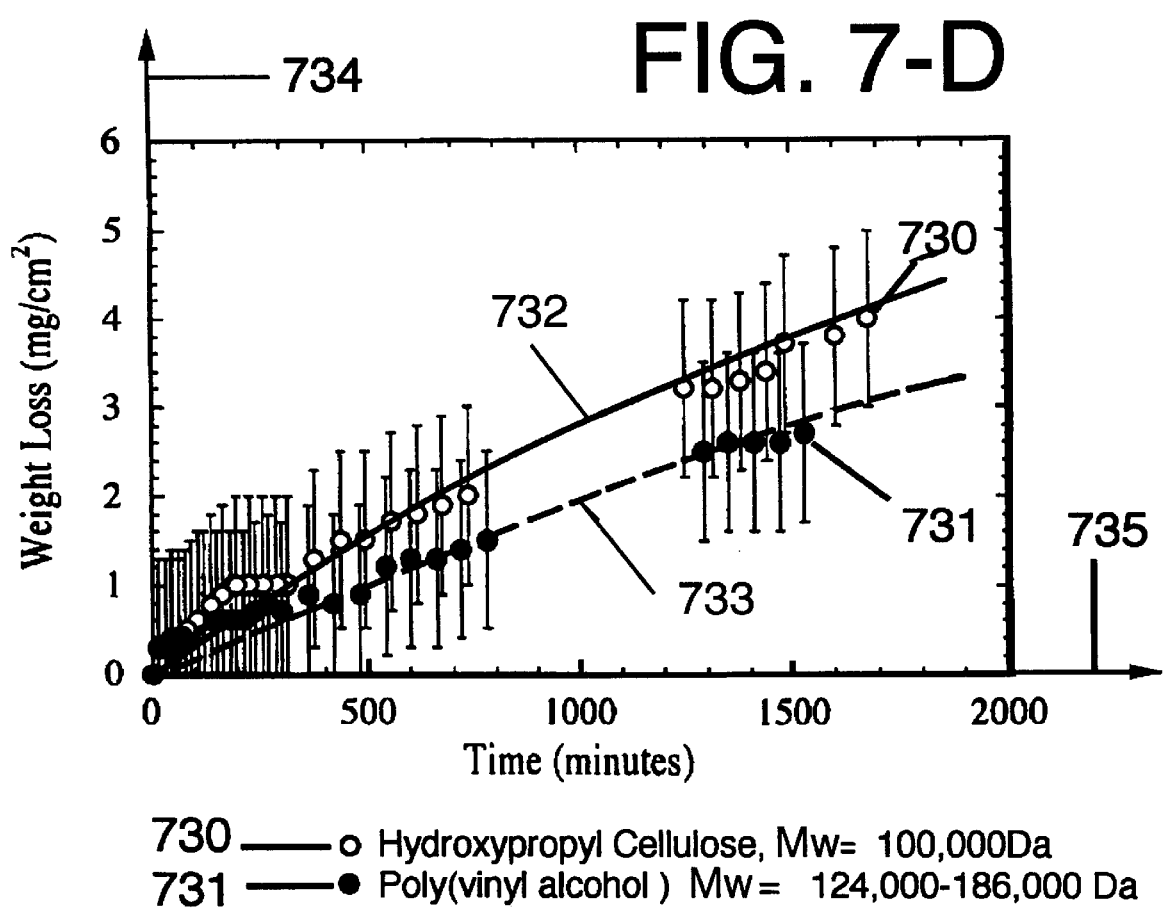

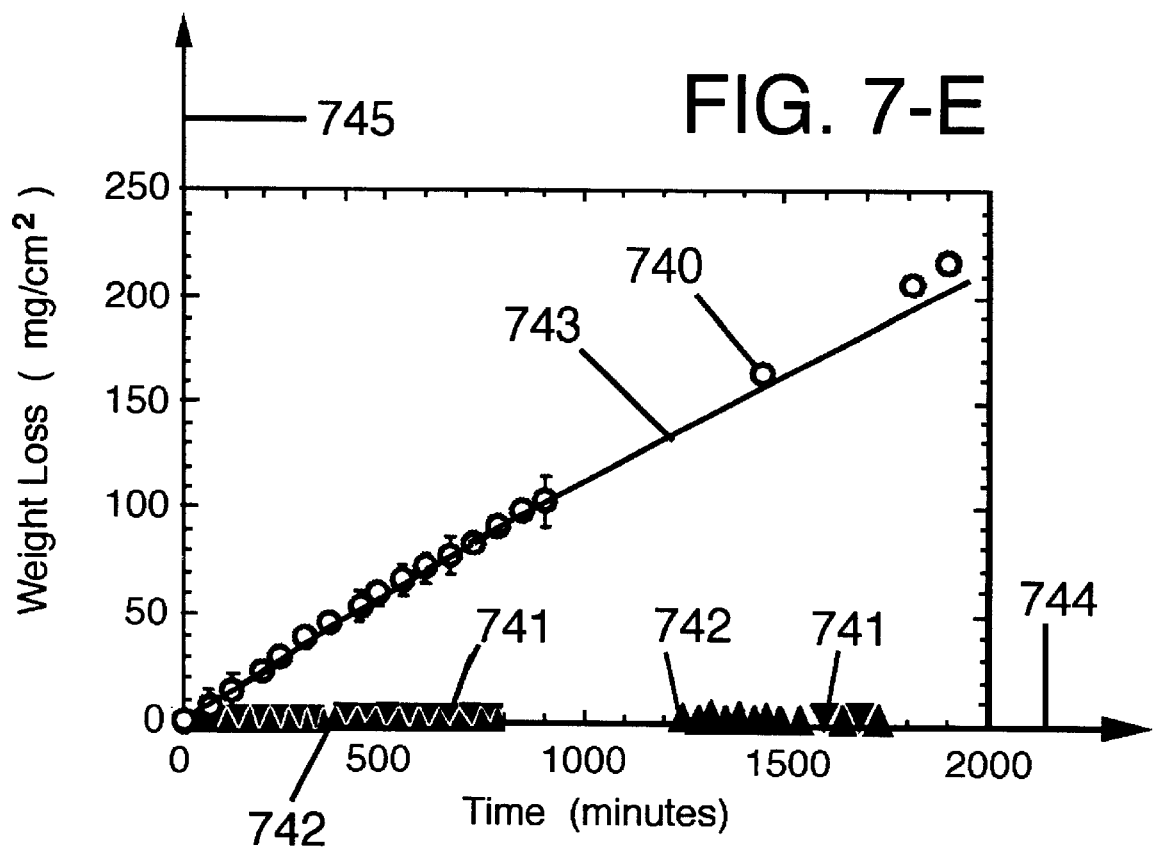

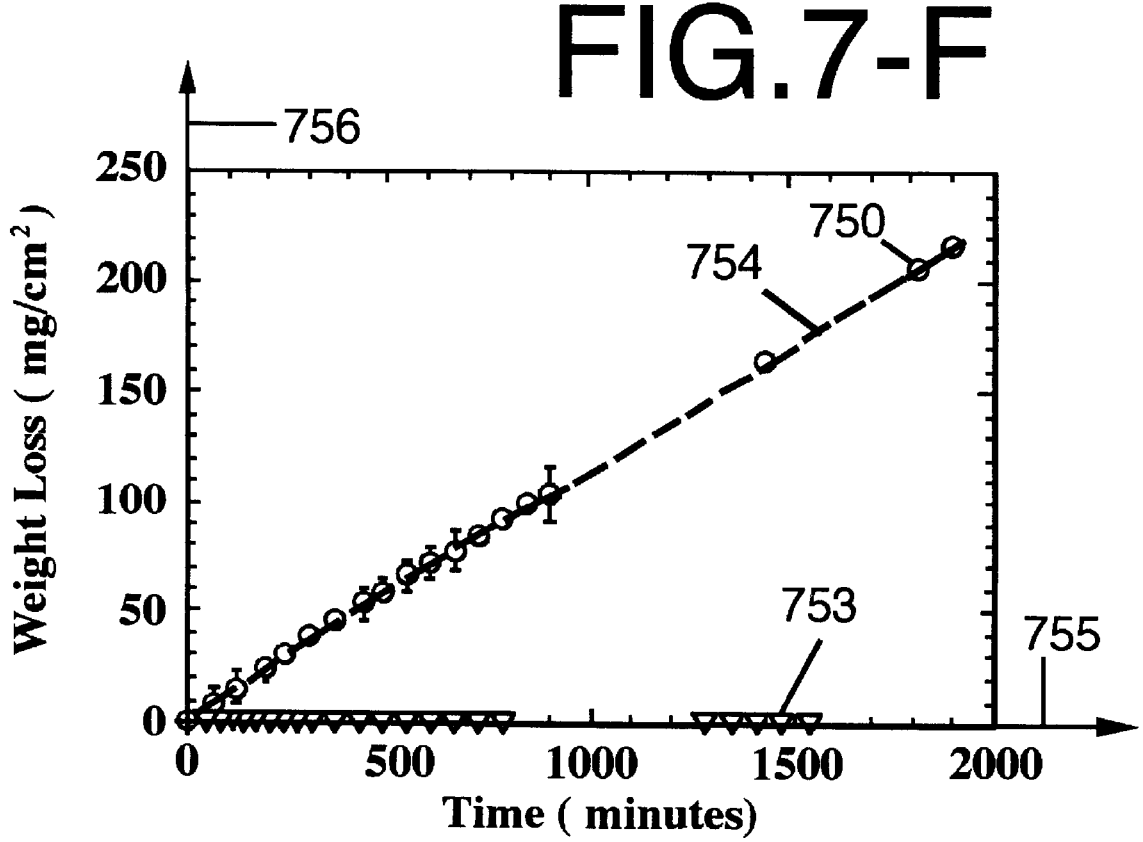
FIG.7-F

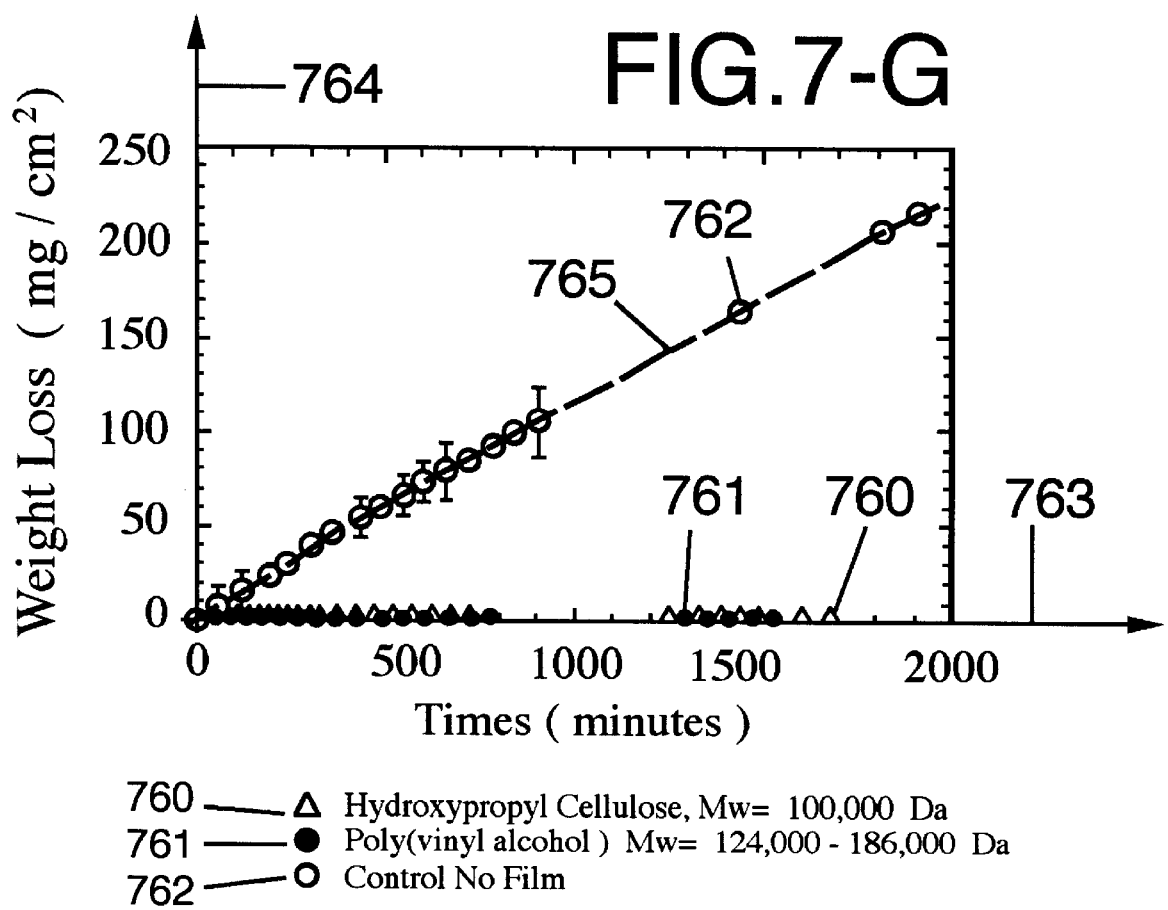

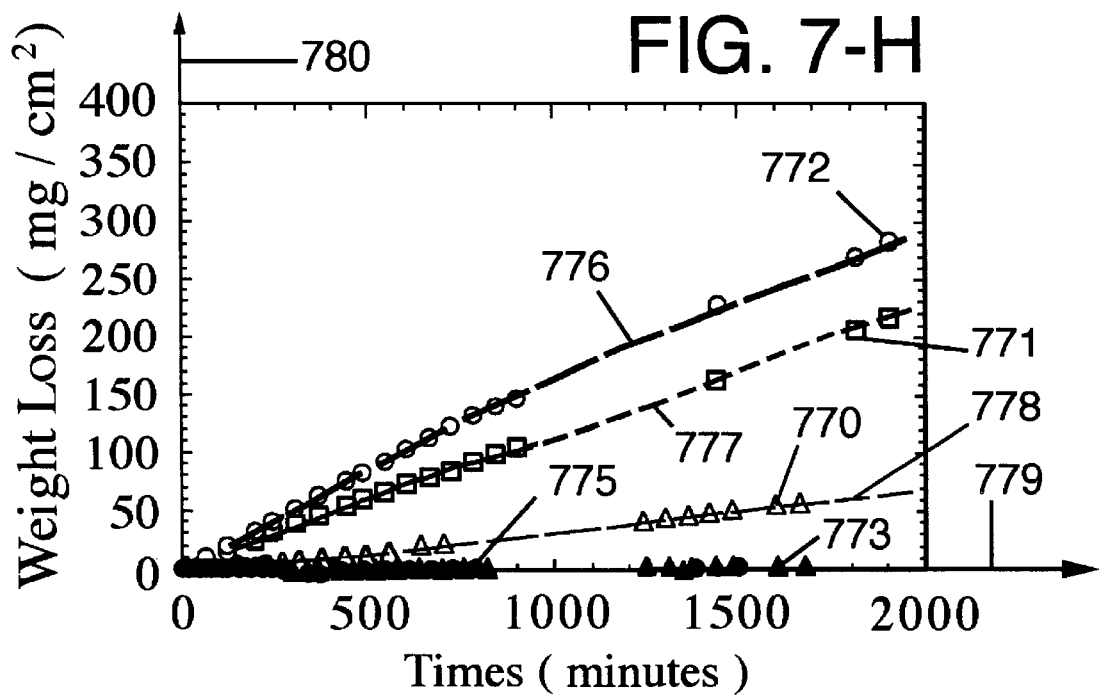
FIG. 7-H
| | | | |
|---|---|---|---|
| 770 — △ | C.P. Formate | ( log P = 3.9 Vapor Pressure = 0.1 ) | Control |
| 771 — □ | Limonene | ( log P = 4.4 Vapor Pressure = 1.4 ) | Control |
| 772 — ○ | Beta-Pinene | ( log P = 4.6 Vapor Pressure = 2.2 ) | Control |
| 773 — ▲ | C.P. Formate | ( log P = 3.9 Vapor Pressure = 0.1 ) | |
| 774 — ■ | Limonene | ( log P = 4.4 Vapor Pressure = 1.4 ) | |
| 775 — ● | Beta-Pinene | ( log P = 4.6 Vapor Pressure = 2.2 ) | |

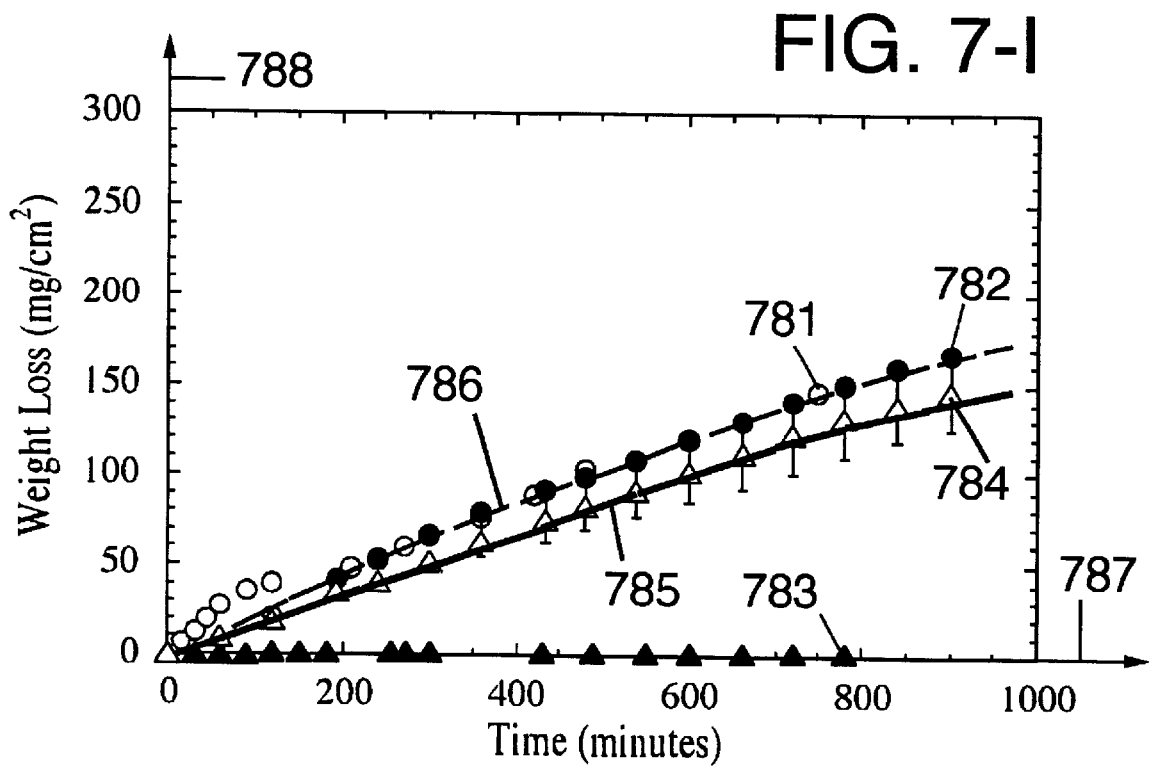
FIG. 7-I
781 —○— Ethyl Tiglate ( log P= 2.0 Vapor Pressure = 1.8 )
782 —●— Ethyl Tiglate ( log P= 2.0 Vapor Pressure = 1.8 ) - Control.
783 —▲— Beta- Pinene ( log P= 4.6 Vapor Pressure = 2.2 )
784 —△— Beta- Pinene ( log P= 4.6 Vapor Pressure = 2.2 ) - Control.

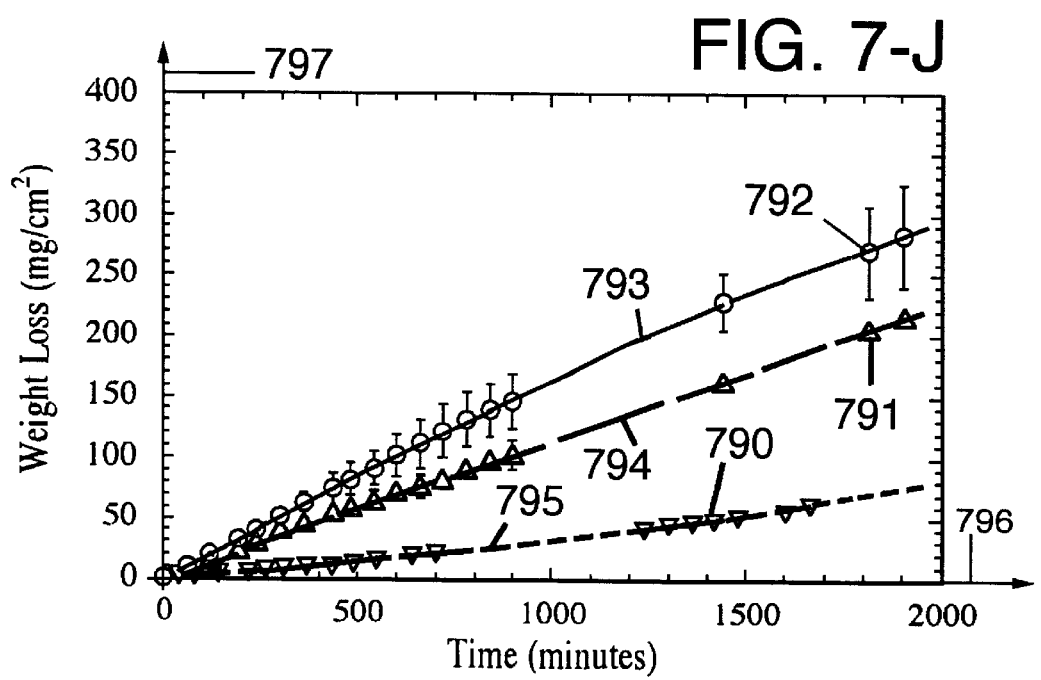

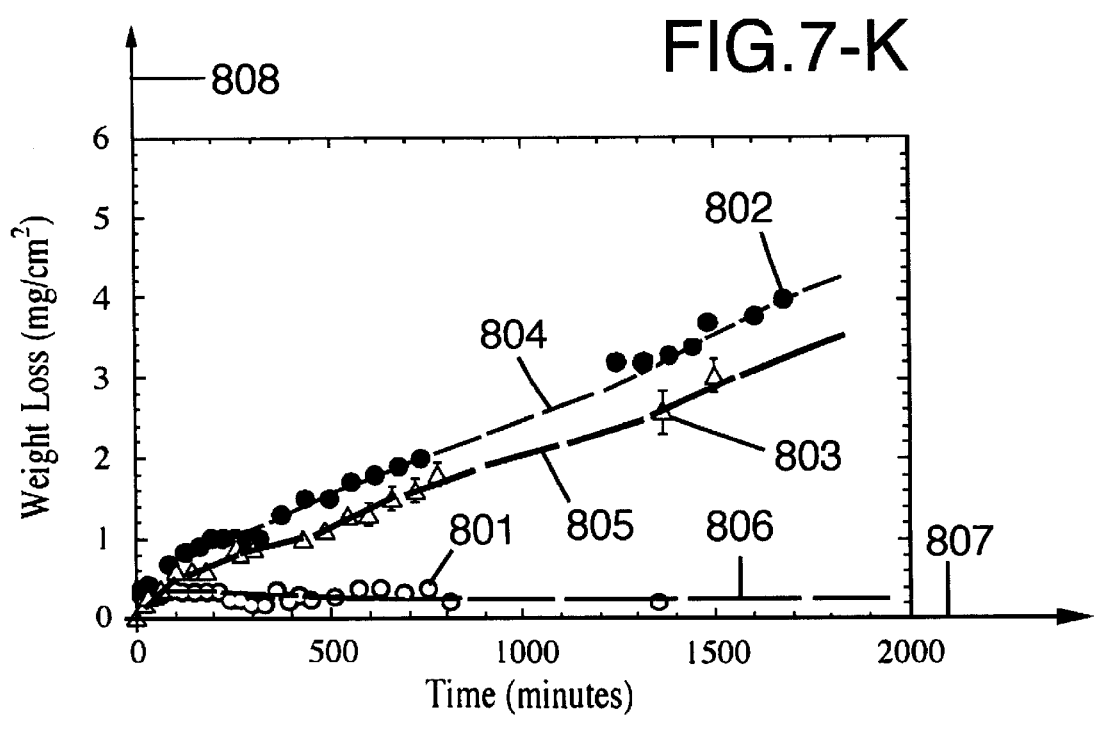

APPLICATION OF FILM FORMING TECHNOLOGY TO FRAGRANCE CONTROL RELEASE SYSTEMS; AND RESULTANT FRAGRANCE CONTROL RELEASE SYSTEM

PENDING RELATED APPLICATIONS

This application is a Continuation-in-Part of Application for U.S. Ser. No. 09/150,240 filed on Sep. 10, 1998, now U.S. Pat. No. 6,063,365.

BACKGROUND OF THE INVENTION

Our invention is directed to (i) an emulsifier-free, single phase, nonporous, continuous, permeable polymeric film having a substantially uniform thickness, having entrapped and dissolved therein a fragrance material which is capable of evolving from the film into the environment proximate the film by means of molecular diffusion in a sustained and controlled release manner, as well as (ii) a process for using such polymeric film in order to impart a fragrance into the environment above the unobstructed outer surface of the film when the film is coated on the surface of a solid or semi-solid support, e.g., a woven or non-woven fabric substrate, a solid surface or the human epidermis.

Controlled release fragrance compositions traditionally required prepackaging of encapsulated fragrances into the final product, for example, a coacervation, encapsulation system composed of fragrance encapsulated in a gelatin-gum arabic shell.

Control release systems using film forming polymers have been previously attempted. Thus, Japanese Published Patent Application J9 0057-428 abstracted as follows:

NIEK-D23 87-183168/26=J90057-428-B
Prepn. of long-lasting fragrance—contg. hydroxypropyl:cellulose, ethanol and/or methanol soln. and vinyl pyrrolidone
NIPPON EKISHO KK 13.11.85-JP-262894
A97+P34 (04.12.90)*J62114909-A A61k-07/46+A611-09/01 13.11.85 as 252894 (RP)
1–30 wt % of hydroxypropylcellose is added to the ethanol or methanol soln. of 1–60 wt % polyvinyl pyrrolidone. Then 1–60 wt % of fragrance material is added and mixed.
AVANTAGE—Long lasting fragrance is obtd. when applied to the film or paper. Polyvinyl pyrrolidone covers the fragrance material contained and prevents its loss. (J62114909-A) (3pp)

indicates that a long lasting fragrance is obtained when hydroxypropyl cellulose in an amount of from about 1 up to about 30% is added to ethanol or methanol previously containing polyvinylpyrrolidone in an amount of from about 1 up to about 60%. Then a fragrance material in an amount of from about 1 up to about 60% by weight is added to the resulting material and admixed. The resulting product is applied to a film or paper. The Japanese Published Application J9 0057-428 does not disclose a control release technology provided by our invention. The Published Japanese Application, furthermore, does not teach that an effective control release system requires that the fragrance element and the film forming polymer be chosen such that the film forming polymer permits the fragrance to molecularly diffuse into the environment surrounding the film at a permeation rate of from about $1 \times 10^{-7}$ up to about 0.1 mg-mm/cm$^2$-minute in a sustained and control release manner.

Holzner, U.S. Pat. No. 4,803,195 issued on Feb. 7, 1989 discloses personal care compositions having deodorant or antiperspirant activity and containing in addition to an active deodorant or antiperspirant base, a perfuming base either in the form of an aqueous emulsion or in microecapsulated form. The perfume base of Holzner is combined with a film forming substrate and an emulsifying agent. The Holzner, U.S. Pat. No. 4,803,195 claims:

"1. A perfuming composition with deodorant or antiperspirant action for use in personal care, characterised in that it contains, in addition to an active deodorant or antiperspirant base, a perfuming base, either in the form of an aqueous emulsion, or in microencapsulated form, the said perfuming base being combined with
   a. a solid film-forming substrate chosen from polyvinyl acetate, polyvinyl alcohol, dextrins, natural or modified starch, vegetable gums, pectins, xanthans, carboxymethyl cellulose, methyl cellulose, hydroxymethyl cellulose and lipoheteropolysaccharides, and
   b. an emulsifying agent chosen from mono- or diglycerides of fatty acids, esters derived from the combination of fatty acids with sorbitol or a saccharide, or their alkoxylated derivatives, or an ester of tartaric, citric, ascorbic or lactic acid."

Holzner and Moulin, Canadian Patent No. 2,008,556, disclose a perfuming composition with deodorant or antiperspirant action for use in personal care compositions. The Holzner composition contains, in addition to an active deodorant or antiperspirant base, a perfuming base either in the form of an aqueous emulsion or in microencapsulated form, with the perfuming base being combined with a film-forming substrate and an emulsifying agent, and the composition being characterized in that the film-forming substrate contains polyvinylpyrrolidone. The film-forming substrate in the Holzner and Moulin patent can contain, other than polyvinylpyrrolidone, at least one compound chosen from polyvinyl acetate, polyvinyl alcohol, dextrins, natural or modified starch, vegetable gums, pectins, xanthanes, carboxymethyl cellulose, methyl cellulose, hydroxyethyl cellulose and lipoheteropolysaccharides.

The prior art teaches away from our invention. Holzner, U.S. Pat. No. 4,803,195 requires the presence of an emulsifying agent and the formation of a fragrance polymer emulsion that is subsequently spray dried or used in emulsion form. Our invention does not require an emulsion, is applicable to all products containing volatile solvents that are applied to surfaces and requires that the film forming polymer is an effective "barrier" to the fragrance or fragrance ingredient as determined by the "FRAGRANCE PERMEATION TEST" hereinafter defined and hereinafter described.

Thus, whereas the prior art discloses the usefulness of films formed from modified starches such as hydroxypropyl cellulose in conjunction with fragrance, films formed from modified starches such as hydroxy cellulose do not fall within the scope of our invention. Ethyl tiglate is a common fragrance ingredient and permeates through a film formed from hydroxypropyl cellulose at a rate equal to its evaporation rate as determined by the "FRAGRANCE PERMEATION TEST" described, infra. Thus, hydroxypropyl cellulose would not evolve from such film into the environment proximate to the film by means of molecular diffusion at a permeation rate of <0.1 mg-mm/cm$^2$-min.

Israel Patent No. 91422 issued on Oct. 31, 1995 (assigned to Dento-Med Industries Inc.) discloses a stable oil-in-water emulsion characterized in that it contains 2-hydroxyethyl methacrylate homopolymer from which a non-gummy, hygroscopic, flexible and pliable thin layer which can be deposited on an epidermal surface can be made and which optionally contains a plurality of plasticizers each having a different solvency power for 2-hydroxyethyl methacrylate homopolymer thereby controlling the pliability of the layer of 2-hydroxyethyl methacrylate homopolymer. On page 14 of Israel Patent No. 91422, it is indicated that the thin layer is formed when a cosmetic formulation is deposited on an epidermal surface. Although at pages 21–23 of the Israel patent, a cosmetic formulation of Dento-Med discloses a number of possible ingredients, there is no mention and no implication of the use of fragrances therein such as those fragrances which can diffuse out of the membrane as is claimed in our invention.

Blakeway and Sauvage, U.S. Pat. No. 5,369,092 issued on Nov. 29, 1994, discloses novel odorant compositions comprising panthenol with a perfume concentrate and ethanol, whereby the addition of panthenol prolongs the diffusion of perfume materials from the skin. The panthenol, however, is different in kind rather than degree from the polymers used in film forming the fragrance-containing films of our invention and does not give rise to the unexpected, unobvious and advantageous results of the fragrance carrier system of our invention; and further, does not give rise to the fragrance substance evolving from the film into the environment proximate the film by means of molecular diffusion at a permeation rate of from about $1\times10^{-7}$ up to about 0.1 mg-mm/cm$^2$-minute.

PCT Patent Application No. 97,/25018 published on Jul. 17, 1997 and assigned to Launceston, Ltd. of St. Peter Port, Guernsey, Channel Islands, discloses a scented nail polish which comprises:

(a) at least one solvent;

(b) at least one resin;

(c) at least one colorant; and (D) at least one liquid perfume where the weight ratio of resin:liquid perfume is from 2.5:1 down to 1:2.5. Examples of the resin component of the scented nail polish of PCT Patent Application No. 97/25018 are nitrocellulose, cellulose acetate, cellulose acetate-butyrate, ethyl cellulose, vinyl polymers, methacrylate polymers and acrylate polymers. PCT Patent Application No. 97/25018 does not expressly or implicitly disclose the fragrance control release system of our invention, whereby a fragrance substance is evolved from a polymeric film into the environment proximate said film by means of molecular diffusion at a permeation rate of from about $1\times10^{-7}$ up to about 0.1 mg-mm/cm$^2$-minute in a sustained and controlled release manner as measured by the "FRAGRANCE PERMEATION TEST" described, infra.

THE INVENTION

Our invention is directed to an emulsifier-free, single phase, nonporous, continuous, permeable polymeric film having a substantially uniform thickness of from about 1 up to about 150 microns, having entrapped and dissolved therein molecules of at least one fragrance substance capable of evolving from said film into the environment proximate said film by means of molecular diffusion at a permeation rate of from about $1\times10$ up to about 0.1 mg-mm/cm$^2$ -min in a sustained and controlled release manner.

More particularly, our invention is directed to a film which is an emulsifier-free, single phase, nonporous, continuous, permeable polymeric film which comprises a polymer and a fragrance substance located on the surface of a substantially planar solid or semi-solid support, e.g., a woven or non-woven fabric, a solid surface or the human epidermis, said polymeric film having two substantially parallel laminar surfaces, a first laminar polymer surface and a second laminar polymer surface, said second laminar polymer surface being juxtaposed with at least a portion of said surface of said planar solid or semi-solid support, e.g., a woven or non-woven fabric, a solid surface or the human epidermis, said polymeric film having a substantially uniform thickness of from about 1 micron up to about 150 microns, said polymeric film having entrapped and dissolved therein molecules of at least one fragrance substance in an initial weight ratio $R_i$ of fragrance:polymer of from about 0.01:20 up to about 50:0.01, said fragrance substance being:

(i) capable of evolving from within the polymeric film through said first laminar polymer surface into the environment proximate to and above said first laminar polymer surface by means of substantially steady state molecular diffusion at a substantially constant permeation rate of from about $1\times10^{-7}$ up to about 0.1 mg-mm/cm$^2$-min in a sustained and controlled release manner; and (ii) substantially incapable of permeating that portion of said second laminar polymer surface which is juxtaposed with the surface of said planar solid or semi-solid support (e.g., the epidermis)

said polymeric film having two regions located across the cross-section of said polymeric film, taken along the directional vector from said first laminar polymer surface to said second laminar polymer surface:

(a) a first permeation region proximate and immediately adjacent to said first laminar polymer surface; and (b) a second reservoir region proximate and immediately adjacent to said second laminar polymer surface, said first permeation region being juxtaposed with said second reservoir region, said second reservoir region containing a high proportion of said fragrance substance relative to the proportion of said fragrance substance contained in said first permeation region.

Another embodiment of the article of our invention is a film which is an emulsifier-free single phase, nonporous, continuous, permeable polymeric-gel film comprising:

(i) a water-soluble or water-swellable polymer;

(ii) a fragrance material;

(iii) water; and (iv) a gelling agent composition comprising at least one gelling agent, said film being located on the surface of a substantially solid or semi-solid support, said polymeric-gel film having two substantially parallel laminar surfaces:

(i) a first laminar polymeric-gel surface; and (ii) a second laminar polymeric-gel surface, said second polymeric-gel surface being juxtaposed with at least a portion of said surface of said substantially planar solid or semi-solid support (e.g., the epidermis), said polymeric-gel film having a substantially uniform thickness of from about 1.0 microns up to about 150 microns, said polymeric-gel film having entrapped and dissolved therein:

(i) molecules of at least one fragrance substance in an initial weight ratio of fragrance:polymeric gel of from about 0.01:20 up to about 50:0.01; and (ii) water molecules in an initial weight ratio of water:polymeric gel of from about 1:500 up to about 500:1, said molecules of fragrance substance and said molecules of water being uniformly dispersed in a single phase throughout said polymeric-gel film, said fragrance substance being:

(a) capable of evolving from within the polymeric gel film through said first laminar polymeric-gel surface into the environment proximate said first laminar polymeric-gel surface by means of molecular diffusion at a permeation rate of from about $1\times10^{-7}$ up to about 0.1 mg-mm/cm$^2$-min in a substantially controlled release manner in accordance with Fick's second law; and (b) substantially incapable of permeating that portion of said second laminar polymeric-gel surface which is juxtaposed with said surface of said planar solid or semi-solid support (e.g., a woven or non-woven fabric, a solid surface or the human epidermis)

Our invention is also directed to a process for imparting a fragrance into the environment above the unobstructed outer surface of a polymer film coated on the surface of a solid or semi-solid support (e.g., a woven or non-woven fabric such as woven cotton, woven polyester, WOVEN NYLON® or a non-woven polyurethene or a solid surface or the human epidermis) comprising the sequential steps of:

(i) combining a composition comprising a solvent consisting of water, ethanol or mixtures of water and ethanol with a solvent-soluble polymer solute to form a polymer solution; then (ii) dissolving a soluble fragrance substance in said polymer solution in order to form an aromatized polymer solution; and then (iii) uniformly applying said aromatized polymer solution to said substantially planar surface of said solid or semi-solid support (e.g., a woven or non-woven fabric, a solid surface or the human epidermis), whereby molecules of the fragrance are capable of evolving from the resulting polymeric film into the environment surrounding the polymeric film by means of molecular diffusion at a permeation rate of from about $1\times10^{-7}$ up to about 0.1 mg-mm/cm$^2$-min in a sustained and controlled release manner.

More specifically, the process of our invention for imparting a fragrance into the environment above the unobstructed outer surface of a polymer film coated on the surface of a solid or semi-solid support (e.g., a woven or non-woven fabric) comprises the sequential steps of:

(i) dissolving a quantity of Q moles of solute polymer in V liters of solvent to form a polymer solution of concentration molar Q/V;

(ii) dissolving F moles of fragrance substance in said solution of polymer to form a fragrance solution of concentration of F/V molar;

(iii) uniformly applying said solution to said surface of said solid support (for example, by means of spraying through a pressure nozzle the solution onto a woven fabric such as woven cotton or onto a non-woven fabric composed of polypropylene), whereby a single-phase, nonporous, continuous, permeable polymeric film having a thickness of from about 1 micron up to about 150 microns and having dissolved therein said fragrance substance capable of evolving from said film into the environment proximate to the unobstructed outer surface of said film by means of molecular diffusion of from about $1\times10^{-7}$ up to about 0.1 mg-mm/$^2$-min in a sustained and controlled release manner, wherein Q/V is in the range of from about 0.01 up to about 3 and F/V is in the range of from about 0.01 up to about 3.

Another process of our invention is one for imparting a fragrance into the environment proximate to the unobstructed outer substantially planar surface of a polymeric-gel film which is coated on the substantially planar surface of a solid or semi-solid support (e.g., a woven or non-woven fabric, a solid surface such as a hardwood furniture surface or the human epidermis) comprising the steps of:

(i) dissolving a quantity of from about 0.01 up to about 20 parts by weight of a solvent-soluble polymer solute in from about 30 up to about 99.98 parts by weight of a solvent/base composition in order to form a polymer-base composition solution containing from about 0.01% up to about 67% polymer;

(ii) adding a gelling agent to the polymer-base composition solution in order to form a polymer-base solution-gelling agent composition;

(iii) dissolving from about 0.01 up to about 50 parts by weight of a soluble fragrance substance in said polymer-base solution-gelling agent composition in order to form an aromatized polymer-base solution-gelling agent composition; and (iv) uniformly applying said aromatized polymer-base solution-gelling agent composition to said substantially planar surface of said solid or semi-solid support (e.g., a woven or non-woven fabric, a solid surface or the human epidermis), whereby a single-phase, nonporous, continuous, permeable polymeric-gel film having a thickness of from about 1 micron up to about 150 microns, having dissolved therein molecules of said fragrance substance capable of evolving from said film into the environment proximate to the unobstructed outer surface of said film by means of molecular diffusion from about $1\times10^{-7}$ up to about 0.1 mg-mm/cm$^2$-min in a sustained and controlled release manner is formed.

Preferably, the aforementioned process involves the steps of:

(i) dissolving the solvent-soluble polymer in a solvent such as water, ethanol or mixtures of water and ethanol;

(ii) mixing the resulting polymer solution with a base containing a substantial amount of propylene glycol and/or polypropylene glycol to form the polymer solution-base mixture;

(iii) feeding the resulting polymer solution-base mixture;

(iv) adding a gelling agent to the resulting mixture; and (v) adding an aromatizing agent to the resulting mixture to form an aromatized polymer solution-base-gelling agent mixture.

Preferably, the solvent-polymer solute is in an amount of from about 30 up to about 99.98 parts by weight of the solvent/base composition, whereby a polymer-base composition solution is formed containing from about 0.01% up to about 67% polymer.

Preferred film forming polymers are as follows:

(i) LUVISKOL® VA 55E having the structure:

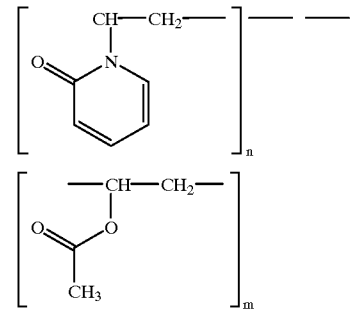

wherein n is an integer of from about 10 up to about 50 and m is an integer of from about 10 up to about 50;

(ii) ULTRAHOLD® 8 having the structure:

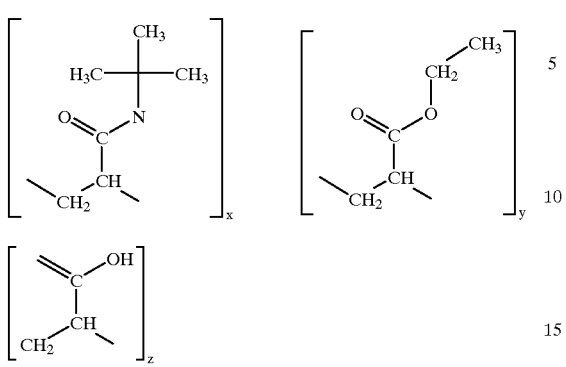

wherein each of x, y and z are integers in the range of from about 10 up to about 50;

(iii) LUVIQUAT® FC or LUVIQUAT® having the structure:

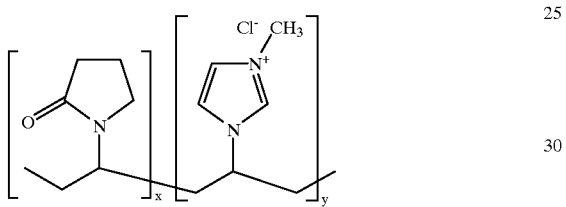

wherein teach of x and y are integers in the range of from about 10 up to about 50;

(iv) ADVANTAGE PLUS® having the structure:

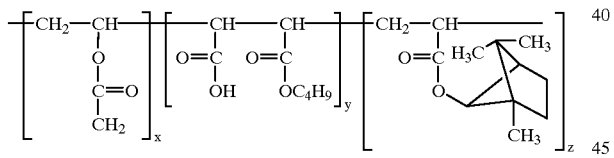

wherein each of x, y and z are integers in the range of from about 10 up to about 50;

(v) GAFQUAT® 734N or GAFQUAT® 755N (trademarks of International Chemical Specialties, Inc.) having the structure;

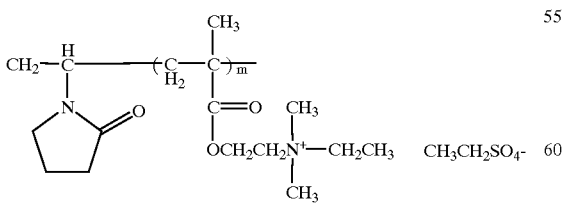

wherein m is an integer of from about 5 up to about 30;

(vi) DIAFORMERS® having the structure:

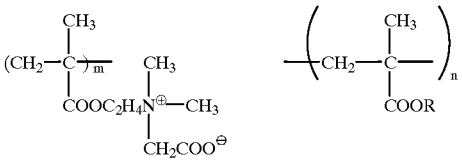

wherein each of m and n are integers of from about 10 up to about 40;

(vii) GAFQUAT® HS-100 having the structure:

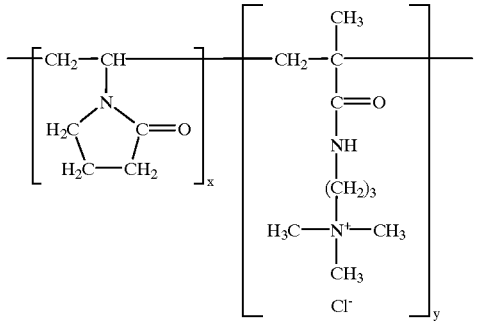

wherein each of x and y are integers of from about 10 up to about 20 (a trademark of International Chemical Specialties, Inc.); and (viii) OMNIREZ® 2000 and GANTREZ® A-425 having the structure:

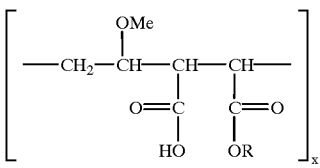

wherein x is an integer of from about 5 up to about 30 (trademarks of International Chemical Specialties, Inc.).

In addition, another polymer group useful in the practice of our invention is partially hydrolyzed polyvinyl acetates, also termed "polyvinyl alcohol" with polyvinyl acetate as hydrolyzed to an extent of from about 73% up to about 99%. Such material is prepared by means of any of Examples I–XIV of U.S. Pat. No. 5,051,222 issued on Sep. 24, 1991, the specification for which is incorporated by reference herein.

Thus, the polyvinyl alcohol or the partially hydrolyzed polyvinyl acetate is prepared first by polymerizing (via a "free radical" polymerization mechanism) polyvinyl acetate having the formula:

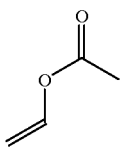

according to the reaction:

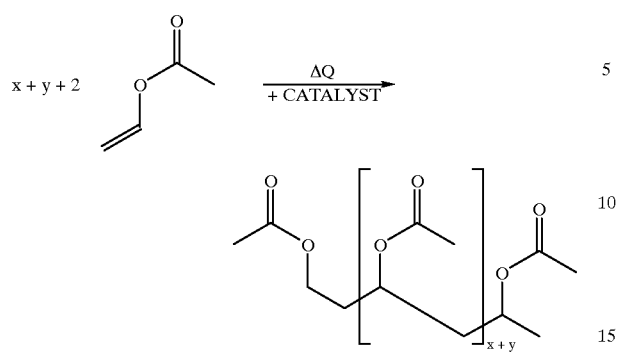

thereby forming a polyvinyl acetate wherein x+y are such that the number average molecular weight of the final product is between 5,000 and 67,000. The resulting polyvinyl acetate having the formula:

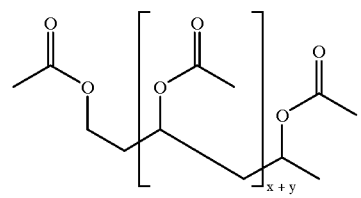

is then hydrolyzed first to form a partially hydrolyzed polyvinyl acetate according to the reaction;

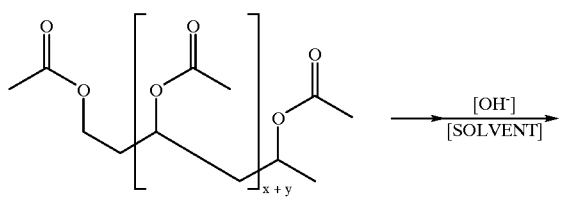

or a mixture of polyvinyl alcohol and partially hydrolyzed polyvinyl acetate according to the reaction:

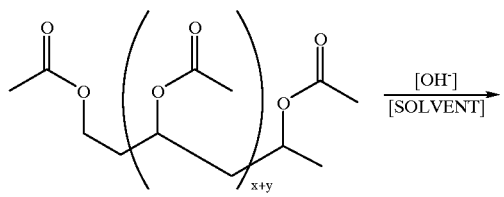

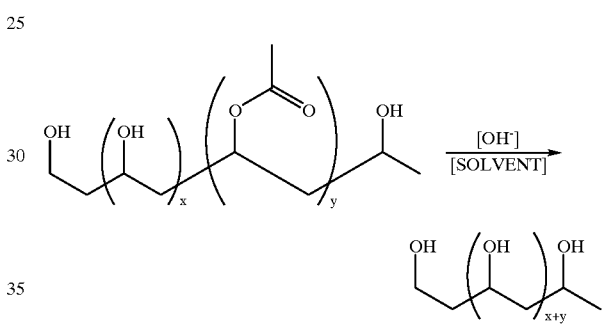

If desired, the partially hydrolyzed polyvinyl acetate may be further hydrolyzed to form polyvinyl alcohol with very few acetyl groups present (thereby forming, for example, 99% hydrolyzed polyvinyl acetate) according to the reaction:

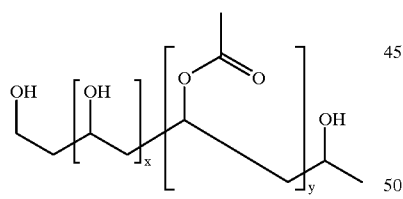

In any event, the ratio of acetyl moieties to hydroxyl moieties is less than about 1:3 in the structure:

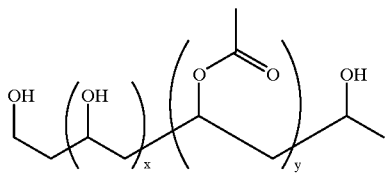

and x and y are defined whereby x+y gives rise to a polymer that has a number average molecular weight of between about 5,000 and 67,000.

Various grades of partially hydrolyzed and substantially fully hydrolyzed forms of hydrolyzed polyvinyl acetate can be used in the practice of our invention, to wit:

| Brand of Hydrolyzed Polyvinyl Acetate (Manufactured by Hoechst A.g., D6230 Frankfurt am Main, Germany) | Number Average Molecular Weight | % Hydrolyzed |
| --- | --- | --- |
| MOWIOL ® 10-74 (trademark of Hoechst A.g.) | 20,000 | 74 |
| MOWIOL ® 4-80 | 24,000 | 80 |
| MOWIOL ® 3-83 | 14,000 | 83 |
| MOWIOL ® 5-88 | 37,000 | 88 |
| MOWIOL ® 8-88 | 67,000 | 88 |
| MOWIOL ® 3-98 | 16,000 | 98 |
| MOWIOL ® 4-98 | 27,000 | 98 |
| MOWIOL ® 6-98 | 47,000 | 98 |
| MOWIOL ® 10-98 | 61,000 | 98 |
| MOWIOL ® GE 4-86 | 62,000 | 86 |

As stated, supra, the fragrance material or mixture of materials useful in the practice of our invention are those which permeate the polymer film at rates equal to or lower than 1.0 mg/cm$^2$/minute as determined by the "FRAGRANCE PERMEATION TEST", described in detail in Example I, infra.

The fragrance substance useful in the practice of our invention has a maximum vapor pressure of about 4.1 mm/Hg at 30° C. When the fragrance material has topnote components, middle note components and bottom note components, the vapor pressure ranges for each of these three groups of components should be as follows:

(a) with respect to the bottom note components, the vapor pressure range should be from about 0.0001 mm/Hg up to about 0.009 mm/Hg at 25° C.;

(b) with respect to the middle note components, the vapor pressure range of the middle note components should be from 0.01 mm/Hg up to 0.09 mm/Hg at 25° C.; and (c) with respect to the top note components, the vapor pressure range of the top note components should be from 0.1 mm/Hg up to 2.0 mm/Hg at 25° C.

An example of such a fragrance as described, supra, is as follows:

| Type of Note | Component | Vapor Pressure mg/Hg at 25° C. |
| --- | --- | --- |
| bottom note | TONALID ® (trademark of Givaudan SA of Geneva, Switzerland) | 0.0001 |
| bottom note | hexyl cinnamic aldehyde | 0.0003 |
| bottom note | cis-3-hexenyl salicylate | 0.0008 |
| bottom note | ISO E SUPER ® (trademark of International Flavors & Fragrances Inc. of New York, NY) | 0.002 |
| bottom note | peach aldehyde coeur | 0.002 |
| bottom note | LILIAL ® (trademark of Givaudan, Inc. of Clifton, NJ) | 0.003 |
| bottom note | cyclamal | 0.004 |
| bottom note | β-ionone | 0.006 |
| bottom note | γ-methyl ionone | 0.006 |
| bottom note | citronellol | 0.009 |
| bottom note | methyl nonyl acetaldehyde | 0.009 |
| middle note | allyl cyclohexyl propane | 0.01 |
| middle note | α-terpineol | 0.02 |
| middle note | 1-borneol | 0.02 |
| middle note | dipropylene glycol | 0.02 |
| middle note | hyacinth extract | 0.02 |
| middle note | β-phenyl ethyl alcohol | 0.02 |
| middle note | VERTENEX ® HC (trademark of International Flavors & Fragrances Inc. of New York, NY) | 0.03 |
| middle note | linalool | 0.05 |
| middle note | allyl amyl glycolate | 0.07 |
| middle note | linalyl acetate | 0.07 |
| middle note | dihydromyrcenol | 0.09 |
| middle note | isobornyl acetate | 0.09 |
| middle note | methyl chavicol | 0.09 |
| top note | benzyl acetate | |
| top note | camphor | 0.1 |
| top note | styralyl acetate | 0.1 |
| top note | ALDEHYDE AA Triplal ™ (trademark of International Flavors & Fragrances Inc. of New York, NY) | 0.3 |
| top note | eucalyptus oil | 1.7 |
| top note | cis-3-hexenyl acetate | 2.0 |

In general, the perfume materials useful in the practice of our invention have a calculated $\log_{10}P$ of between 1 and 8 (P being the n-octanol-water partition coefficient of the perfumery material).

The range of permeation rates of the perfumery materials through the polymer film or the gel film is from about $1\times10^{-7}$ up to about 0.1 mg-mm²-min (milligram-millimeter/square centimeter-minute). The following materials having the following calculated $\log_{10}P$ also have the following permeation rates through various polymer films useful in the practice of our invention:

| Aroma Chemical | Polymer Film Material | Permeation Rate mg - mm thickness cm² area - minute | Calculated $\log_{10}P$ |
|---|---|---|---|
| β-pinene | carboxymethyl cellulose | $2.8 \times 10^{-3}$ | 4.6 |
| n-octanal | carboxymethyl cellulose | $2.8 \times 10^{-3}$ | 2.9 |
| ethyl tiglate | carboxymethyl cellulose | $2.8 \times 10^{-3}$ | 2.0 |
| β-pinene | polyvinyl alcohol (74% hydrolyzed) | $2.5 \times 10^{-3}$ | 4.6 |
| ethyl tiglate | polyvinyl alcohol (74% hydrolyzed) | $5 \times 10^{-3}$ | 2.0 |
| β-pinene | polyvinyl alcohol (98% hydrolyzed) | $2 \times 10^{-3}$ | 4.6 |
| ethyl tiglate | polyvinyl alcohol (98% hydrolyzed) | $2 \times 10^{-3}$ | 2.0 |
| d-limonene | hydroxypropyl cellulose (molecular weight = 100,000) | $2 \times 10^{-3}$ | 4.4 |
| d-limonene | hydroxypropyl cellulose (molecular weight = 370,000) | $1.5 \times 10^{-3}$ | 4.4 |
| d-limonene | polyvinyl alcohol (98% hydrolyzed, molecular weight = 150,000) | $2 \times 10^{-3}$ | 4.4 |
| the formic acid ester of 1,1-dimethyl-3(1-hydroxy-ethyl) cyclohexane (CP FORMATE ®, Registered Trademark of International Flavors & Fragrances Inc.) | hydroxypropyl cellulose (molecular weight = 100,000) | $2.5 \times 10^{-3}$ | 3.9 |

The mathematical models for the fragrance release are as follows:

$$\frac{dM}{dt} = 2\sqrt{\frac{D_e}{\pi t_e}} A_{ge}[c_e^i(t) - c_e(t)];$$

$$\frac{dc_e(t)}{dt} = \frac{h_D A}{V_e}\left[\frac{c_g(t)}{K_{ge}} - c_e(t)\right];$$

$$\frac{dM}{dt} = -v_e \frac{dc_e(t)}{dt} = v_g \frac{dc_g(t)}{dt};$$

$$c_g(t) = \frac{v_e}{v_g}[c_e(0) - c_e(t)];$$

$$\frac{dc_e(t)}{dt} = \alpha[\beta - c_e(t)\gamma]; \quad \alpha = \frac{h_D A_{ge}}{v_e};$$

$$\beta = \varepsilon c_e(0); \quad \gamma = [1+\varepsilon]; \quad \varepsilon = \frac{v_e}{v_g K_{ge}};$$

$$c_e(t) = \frac{c_e(0)}{(1+\varepsilon)}\{\varepsilon + \exp[-\alpha\gamma t]\};$$

$$c_g(t) = \frac{K_{ge}c_e(0)}{(1+1/\varepsilon)}[1 - \exp(-\alpha\gamma t)];$$

$$c_g(t) = \frac{K_{ge}c_e(0)}{\left(\frac{K_{ge}v_g}{v_e}+1\right)}\left[\left(1 - \exp\left\{-\left(1+\frac{v_e}{K_{ge}v_g}\right)\frac{h_D A_{ge}}{v_e}t\right\}\right)\right]$$

$$c_g(\infty) = \frac{K_{ge}c_e(0)}{\left(\frac{K_{ge}v_g}{v_e}+1\right)}; \quad \text{and}$$

$$\frac{c_g(t)}{c_g(\infty)} = \left[1 - \exp\left\{-\left(1+\frac{v_e}{K_{ge}v_g}\right)\frac{h_D A_{ge}}{v_g}t\right\}\right],$$

wherein each of the terms set forth in the foregoing mathematical models are set forth in the paper entitled "Mathematical Models of Flavor Release from Liquid Emulsions" by Harrison, et al, *JOURNAL OF FOOD SCIENCE*, July/August 1997, Volume 62, No. 4, at pages 653–664, the disclosure of which is incorporated by reference herein. The controlling factors for "flavors" as set forth in the Harrison, et al paper apply equally as well to the fragrances discussed herein.

Examples of gels useful in the practice of our invention are as follows:

(i) sodium stearate;

(ii) bis(ureido) gels as disclosed in Freemantle in the article "Durable Organic Gels" appearing in *CHEMICAL & ENGINEERING NEWS*, Volume 76, No. 4, at pages 35–38, the disclosure of which is incorporated by reference herein.

(iii) soap, fatty acid-based gelling agents as particularly described in U.S. Pat. No. 5,585,092 issued on Dec. 17, 1996 (Trandai, et al), the specification for which is incorporated by reference herein, including salts of fatty acids containing 12 to about 40 carbon atoms, preferably salts of $C_{12}$–$C_{22}$ fatty acids, more preferably salts of $C_{14}$–$C_{20}$ fatty acids and most preferably salts of $C_{16}$–$C_{20}$ fatty acids with the salt forming cations for use in these gelling agents including metal salts such as alkalai metals, for example, sodium and potassium and alkaline earth metals, for example, magnesium and aluminum; and in addition, hydrogel-forming polymeric gelling agents as disclosed in U.S. Pat. No. 4,076,663 (Masuda, et al) issued on Feb. 28, 1978, the specification is incorporated by reference herein; and U.S. Pat. No. 4,731,067 (Le-Khac) issued on Mar. 15, 1988, incorporated by reference herein in its entirety. The suitable hydrogel-forming polymeric gelling agents are specifically discussed at columns 6–12 of U.S. Pat. No. 5,585,092 (Trandai, et al) issued on Dec. 17, 1996, incorporated by reference herein in its entirety; and (iv) silicone gels having the structures:

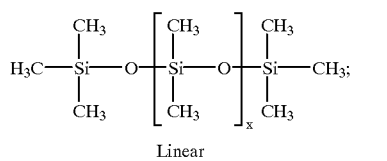

Linear (I)

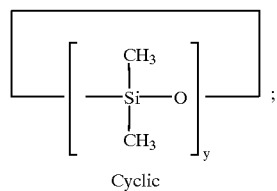

Cyclic (II)

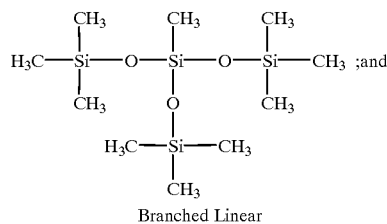

Branched Linear (III)

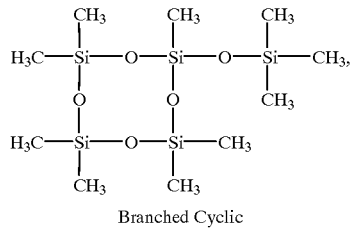

Branched Cyclic (IV)

as described in detail in U.S. Pat. No. 5,623,017 issued on Apr. 22, 1997, the disclosure of which is incorporated by reference herein.

When that embodiment of our invention is used wherein the fragrance is evolved from a gel coating, the gel coating formulation as stated, supra, preferably contains propylene glycol or polypropylene glycol with the number of propylene oxy units being from about 2 up to about 30. An example of the formulation useful with the gel is as follows:

water;
propylene glycol;
aluminum chlorohydrate;
dimethicone;
sorbitol;
cyclomethicone;
dimethicone copolyol;
ethyl alcohol; and
fragrance.

Preferably, the fragrance materials of our invention have a $\log_{10}P$ of between about 1 up to about 5.

The barrier properties of an effective film forming polymer are, to a good approximation, a function of the degree of crystallinity of the film and the solubility of the fragrance ingredient in the film. Polyvinyl alcohol, for example, has a high degree of crystallinity and has good barrier properties to a large number of fragrance ingredients. Hydroxypropyl cellulose, on the other hand, forms an amorphous film and, thus, its barrier properties are a function of the solubility of the fragrance ingredient in the hydroxypropyl cellulose. The solubility of fragrance ingredients in amorphous films can estimated by the calculated octanol-water partition coefficient for the fragrance ingredient. For amorphous hydrophilic films such as the film formed using hydroxypropyl cellulose, fragrance ingredients having a calculated octanol-water partition coefficient of 3 or less readily permeate this film (the calculated 1-octanol/water partition coefficient ("clogP") is calculated according to the technique of J. T. Chou and C. J. Jurs, *Chem. Inf. Comput. Sci.*, 19, 3, 172–178 (1979)).

For the practice of our invention in personal care products such as perfumes, colognes, aftershave splashes, lotions, underarm deodorant and antiperspirant products such as sticks, roll-ons, aerosols and creams; hair products such as styling gels, sprays and mousses and home care products such as liquid surface cleaners and waxes, the product contains preferably from about 1 up to about 3% of a nontoxic alcohol such as ethyl alcohol and/or water, a water soluble film forming polymer and from about 0.1 up to about 30% by weight of a fragrance that has been found not to permeate the film formed by this polymer to any great extent; that is, having a permeation value of from about $1 \times 10^{-7}$ up to about 0.1 mg-mm/cm$^2$-minute.

Upon application of the product to a solid or semi-solid surface, e.g., a woven fabric (woven cotton, woven nylon or woven polyester), a non-woven fabric (made from polyurethane) or the human epidermis, the volatile solvent in most cases ethyl alcohol and/or water evaporates, leaving a film of polymer on the surface of the skin or fabric or solid surface (e.g., plywood) which contains entrapped fragrance. The fragrance permeates out of the polymer at a rate that is proportional to its permeation through the polymer as determined by the "FRAGRANCE PERMEATION TEST," set forth and specifically described in Example I, infra. Fragrance elements that permeate slowly through the film forming polymer will permeate slowly out of the polymer layer applied to the surface (as exemplified, supra). On the other hand, fragrances that permeate rapidly through the polymer will not be retained by the polymer that has been deposited on the surface of the woven or non-woven fabric (e.g., cotton towel), plywood or skin, for example.

The advantages of using the fragrance controlled release systems of our invention, described herein are:

(1) an enhanced sensory impression of the fragrance due to the increased duration of its release from the surface of the woven or non-woven fabric (e.g., cotton towel), plywood or skin, for example;

(2) an enhanced sensory impression of freshness and vibrance due to the increased duration of fragrance ingredients that make up the topnotes of the fragrance; and (3) triggered release of the fragrance from water soluble polymer films upon the addition of moisture.

For the practice of our invention in personal care products such as perfumes, colognes, aftershave splashes, lotions, underarm deodorant and antiperspirant products such as sticks, roll-ons, aerosols and creams; hair care products such as stylizing gels, sprays and mousses and home care products such as liquid surface cleaners and waxes and fabric fresheners, the product of our invention contains from 1–3% of a low molecular weight alcohol- and/or water-soluble film forming polymer and from 0.1 up to about 30% of a fragrance that has been found not to permeate the film formed by this polymer (that is, a low permeation rate of from about $1 \times 10^{-7}$ up to about 0.1 mg-mm/cm$^2$-minute in a substantially controlled release manner in accordance with Fick's Second Law, to wit:

$$\frac{\partial C}{\partial \theta} = \sum_{i=1}^{n} -D_i \frac{\partial^2 C_i}{\partial x^2}$$

wherein $D_i$ is the diffusivity of the $i^{th}$ fragrance substance component; n is the number of fragrance substance components; x is the distance of travel of the $i^{th}$ fragrance component within the polymer film to the first laminar polymer surface thereof; $\theta$ is time; and $C_i$ is the concentration in gram moles per liter of the $i^{th}$ component of said fragrance substance.

Upon application of the product, the volatile solvent, in most cases ethyl alcohol and/or water and/or mixtures of ethyl alcohol and water, evaporates, leaving a film of polymer on the solid or semi-solid surface (which polymer film contains entrapped fragrance). The fragrance permeates out of the polymer through the first laminar polymer surface or laminar polymer-gel surface at a rate that is proportional to its permeation through the polymer as determined by the "FRAGRANCE PERMEATION TEST," described in detail in Example I, infra. Fragrance elements that permeate slowly through the film forming polymer will permeate slowly out of the polymer layer applied to the surface. On the other hand, fragrances that permeate rapidly through the polymer will not be retained by the polymer that has been deposited on the solid or semi-solid surface (e.g., woven or non-woven fabric)

In carrying out the aforementioned process, it is helpful in blending the fragrance, film forming polymer and solvent to use a homogenizer and/or a rotor/stator high shear mixer. Examples of a homogenizer useful in the practice of this aspect of our invention are laboratory homogenizer models 15MR and 31MR manufactured by APV Gaulin, Inc. of 44 Garden Street, Everett, Mass. 02149. Examples of rotor/stator high shear mixers are the high shear in-line mixers manufactured by Silverson Machines, Inc., P.O. Box 589, 355 Chestnut Street, East Long Meadow, Mass. 01028 and by the Scott Process Equipment Corporation, P.O. Box 619, Sparta, N.J. 07871. The aforementioned homogenizers and rotor/stator high shear mixers can be used in conjunction with one another, with the rotor/stator high shear mixers being used first, and then in order to complete the blending, the resultant emulsion is further homogenized using the homogenizers such as laboratory homogenizers, models 15MR and 31MR.

The details of the aforementioned homogenizers and rotor/stator high shear mixers are set forth in the "DETAILED DESCRIPTION OF THE DRAWINGS" section, infra, in the description of FIGS. 3C, 3D and 3E.

Our invention is also directed to apparatus for carrying out the aforementioned processes for imparting a fragrance into the environment above the unobstructed outer surface of a polymer film coated on the surface of a solid or semi-solid support or a polymeric-gel film coated on the substantially planar surface of a solid or semi-solid support such as a woven or non-woven fabric, solid surface or the human epidermis. Such apparatus comprises:

(i) mixing means for a composition comprising a solvent selected from the group consisting of water, ethanol and mixtures of water and ethanol (e.g. 50:50 mixtures) with a solvent-soluble polymer solute to form a polymer solution;

(ii) downstream from said mixing means, blending means for dissolving a soluble fragrance substance in said polymer solution in order to form an aromatized polymer solution (for example, the homogenizer and/or rotor/stator high shear mixer, briefly described, supra, and described in the description of FIGS. 3C, 3D and 3E, infra);

(iii) downstream from said blending means, coating means for uniformly applying said aromatized polymer solution to said substantially planar surface of said solid or said semi-solid support; and, optionally, (iv) downstream from said coating means, drying means for drying the coated polymer solution on said solid or said semi-solid support. The coating means of (iii) may be any applicator device well known to those having ordinary skill in the art, for example, a high pressure nozzle spraying means is preferred when the coating is effected onto the surface of a woven or non-woven fabric. The drying means, useful in the practice of our invention, can be any portable or stationary drying apparatus, such as that manufactured by the CONAIR® Corporation.

BRIEF DESCRIPTION OF THE DRAWINGS

FIG. 1 sets forth cutaway side elevation views of various stages of that aspect of the process of our invention which involves the uniform application of the aromatized polymer-containing solution or polymer solution-gelling agent composition to a substantially planar surface of a solid or semi-solid support (e.g., woven or non-woven fabric, plywood or the human epidermis). Thus, FIG. 1A sets forth a cutaway side elevation view in schematic form of the initially-coated aromatized polymer-containing solution or polymer-gelling-agent-containing solution coated on the solid or semi-solid support. FIG. 1B shows schematic cutaway side elevation views of the same coating midway through solvent evaporation. FIG. 1C shows a schematic cutaway side elevation views of the coated target surface after most of the solvent is evaporated and the coating contains polymer or polymer-gelling agent in admixture with fragrance.

FIG. 1D is a graphical representation of concentration (on the Y axis versus distance on the X axis) of fragrance in the polymer or polymer-gel coating, showing no evaporation through the impermeable solid or semi-solid support and showing evaporation through the permeation region of the polymer or polymer-gelling agent layer and also showing constant concentration of fragrance in the reservoir region of the polymer or polymer-gelling agent coating.

FIG. 2 sets forth a graph of time (on the X axis) versus rate of aroma release (on the Y axis) for the emulsifier-free, single phase, nonporous, continuous permeable polymeric film of our invention containing fragrance.

FIG. 3A sets forth a schematic block flow diagram of the process and apparatus of our invention.

FIG. 3B shows a schematic diagram of the apparatus and process steps of FIG. 3A with an additional schematic representation of the utilization of an electronic program controller (e.g., computer system) whereby market demand information and the like can be utilized to cause automatic alterations in the process variables of the process of our invention where ingredients are admixed, blended, coated and the coating is dried.

FIG. 3C is a schematic perspective view of the first stage of the operation of a rotor/stator high shear mixer, wherein the high speed rotation of the rotor blades within the precision machined mixing workhead exerts a powerful suction drawing liquid and solid materials into the rotor/stator assembly.

FIG. 3D is a schematic perspective diagram of stage two of the operation of a rotor/stator high shear mixer used in the processes and apparatus of our invention where centrifugal force drives materials towards the periphery of the workhead where they are subjected to a milling action in the precision machined clearance between the ends of the rotor blades and the inner wall of the stator.

FIG. 3E is a schematic perspective diagram of the operation of the third stage of a rotor/stator high shear mixer useful in the apparatus of our invention and in carrying out the processes of our invention, wherein the second stage is followed by intense hydraulic shear as the materials are forced, at high velocity, out through the perforations in the stator, then through the machine outlet and along the pipework; while at the same time, fresh materials are continually drawn into the workhead, maintaining the mixing and pumping cycle.

FIG. 4A is a cutaway side elevation view of apparatus used (as shown in Example I, infra) to carry out the "FRAGRANCE PERMEATION TEST" in order to determine the permeability of fragrances through a given polymer and in order to test the emulsifier-free, single phase, nonporous, continuous permeable polymeric films of our invention.

FIG. 4B is a perspective view of the FRAGRANCE PERMEATION TEST apparatus (diffusion cell) of FIG. 4A.

FIG. 4C is a schematic diagram showing the side view of a diffusivity testing apparatus for testing the diffusivity of entrapped fragrance materials including aroma chemicals and fragrance compositions in the emulsifier-free, single phase, nonporous, continuous permeable polymeric film of our invention.

FIG. 4D is the top view of the apparatus of FIG. 4C.

FIG. 5A is a graph indicating the permeability of carnauba wax to the aroma chemicals, ethyl tiglate having the structure:

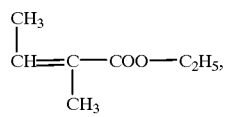

Figure 8:
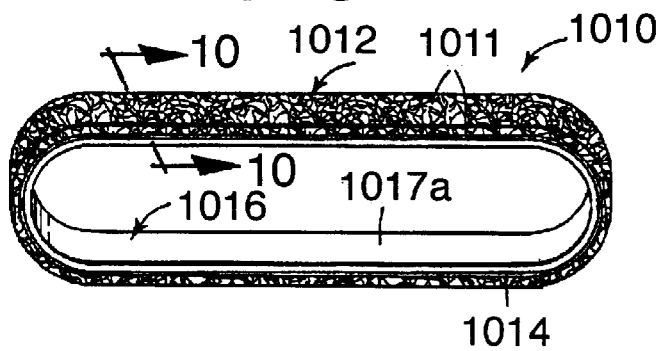

and β-pinene having the structure:

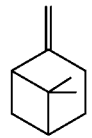

FIG. 5B is a graph showing the permeability of hydroxypropyl cellulose to the aroma chemicals, ethyl tiglate and β-pinene and shows the effect of $\log_{10}P$ for a particular aroma chemical or perfume ingredient where P represents the n-octanol/water partition coefficient for the particular ingredient being tested.

FIG. 5C is a graph showing the permeability of polyvinyl alcohol (98% hydrolyzed polyvinyl acetate) to the aroma chemicals, ethyl tiglate and β-pinene, and also shows the use of a control without the use of the polyvinyl alcohol.

FIG. 5D sets forth an enlargement of that part of the graph of FIG. 5C where the weight loss (mg/cm$^2$), shown on the Y axis is between zero and 4 and shows the actual effect of $\log_{10}P$ on permeation rate for polyvinyl alcohol (98% hydrolyzed polyvinyl acetate).

FIG. 5E sets forth a graph showing the permeability of polyvinyl alcohol (74% hydrolyzed polyvinyl acetate) to ethyl tiglate and β-pinene, with weight loss (mg/cm$^2$) versus time (minutes).

FIG. 5F is an enlargement of that part of the graph of FIG. 5E where the weight loss (mg/cm$^2$) on the Y axis is between zero and 15, with time (minutes) on the X axis being between zero and 2,000 minutes.

FIG. 5G is a graph indicating the permeability of carboxymethyl cellulose to the aroma chemicals, ethyl tiglate having the structure:

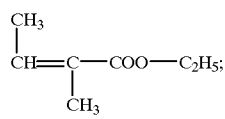

aldehyde C-8 having the structure:

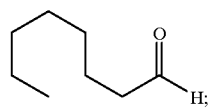

and β-pinene having the structure:

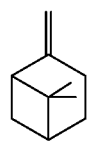

with weight loss (mg/cm$^2$) on the Y axis and time (minutes) on the X axis.

FIG. 5G(A) is an enlargement of that section of the graph of FIG. 5G where the weight loss is between zero and 4 mg/cm².

FIG. 5H is a graph showing the effect of $\log_{10}P$ on the permeation rate of the aroma chemicals, ethyl tiglate and β-pinene through alginate with weight loss (mg/cm²) being between zero and 10 minutes on the Y axis and time (minutes) being between zero and 2,000 minutes on the X axis.

FIG. 5I is a graph showing the permeability of the positively charged polymers, POLYMER LK® and POLYMER LR-400® to ethyl tiglate with weight loss (mg/cm²) on the Y axis being between zero and 8 and time (minutes) on the X axis being between zero 2,000 minutes. POLYMER LK® and POLYMER LR-400® are trademarks of the Amerchol Corporation of Edison, N.J. and are polyquaternary ammonium salts.

FIG. 5J is a graph showing the permeability of ethyl tiglate through different film-forming polymers, to wit:

gelatin;

carboxymethyl cellulose;

hydroxypropyl cellulose;

polyvinyl alcohol (98% hydrolyzed polyvinyl acetate); and polyvinyl alcohol (74% hydrolyzed polyvinyl acetate), and shows comparison with an evaporation rate control, which is simply ethyl tiglate. The weight loss (mg/cm²) is shown on the Y axis between zero and 350, and the time (minutes) is shown on the X axis between zero and 2,000 minutes.

FIG. 5J(A) is an enlargement of that section of the graph of FIG. 5J where the weight loss (mg/cm²) is between zero and 10.

FIG. 5K is a graph showing the permeation of β-pinene through the positively charge polymers, POLYMER LK® and POLYMER LR-400®, described, supra, with the weight loss (mg/cm²) being between zero and 2 on the Y axis, and the time (minutes) being between zero and 2,000 on the X axis.

FIG. 5L is a graph showing the permeation of β-pinene through the film-forming polymers:

gelatin;

carboxymethyl cellulose;

hydroxypropyl cellulose;

polyvinyl alcohol (98% hydrolyzed polyvinyl acetate); and polyvinyl alcohol (74% hydrolyzed polyvinyl acetate), and also shows the graph of the evaporation rate-control for β-pinene without any polymers, with the graph having a Y axis showing weight loss (mg/cm²) from zero to 350 and showing time (minutes) from zero to 2,000 minutes on the X axis.

FIG. 5L(A) is an enlargement of that section of the graph of FIG. 5L for the weight loss (mg/cm²) on the Y axis being from zero to 4 mg/cm².

FIG. 5M is a graph showing permeation versus evaporation rates of hydrophobic aroma chemicals through hydroxypropyl cellulose which has a molecular weight of 100,000 daltons at a temperature of 35° C. for the following materials:

(a) C.P. FORMATE® (registered trademark of International Flavors & Fragrances Inc. of New York, N.Y.) having the structure:

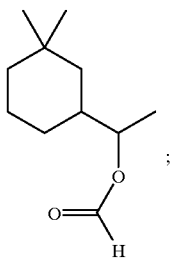

(b) d-limonene having the structure:

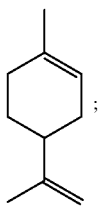

and (c) β-pinene having the structure:

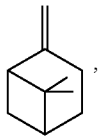

with the weight loss (mg/cm²) on the Y axis being from zero to 400 and time (minutes) on the X axis being from zero to 2,000 minutes.

FIG. 5N sets for the effect of $\log_{10}P$ on permeation rate for hydroxypropyl cellulose for the following materials:

(a) phenyl acetate having the structure:

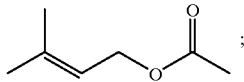

(b) ethyl tiglate;

(c) aldehyde C-8; and (d) β-pinene at a temperature of 35° C. with weight loss (mg/cm²) on the Y axis being from zero to 500 and time (minutes) on the X axis being from zero to 2,000 minutes.

FIG. 5-O is the effect of polymer structure on permeation for ethyl tiglate for the following polymers:

gelatin;

carboxymethyl cellulose;

hydroxypropyl cellulose;

polyvinyl alcohol (98% hydrolyzed polyvinyl acetate);

polyvinyl alcohol (74% hydrolyzed polyvinyl acetate); and control (ethyl tiglate only)

at a temperature of 35° C.

FIG. 5P is an enlargement of that section of FIG. 5-O covering on the Y axis weight loss (mg/cm²) from zero up to 15 mg/cm² for a time period (minutes) on the X axis from zero up to 2,000 minutes and includes the polymers:

gelatin;

carboxymethyl cellulose;

polyvinyl alcohol (98% hydrolyzed polyvinyl acetate); and polyvinyl alcohol (74% hydrolyzed polyvinyl acetate).

FIG. 5Q is a graph showing the effect of polymer structure on permeation for β-pinene for a weight loss (mg/cm$^2$) of from zero to 5 mg/cm$^2$ on the Y axis and for a period of time (minutes) on the X axis of from zero up to 2,000 minutes at a temperature of 35° C. for the following polymers:

carboxymethyl cellulose;

hydroxypropyl cellulose;

polyvinyl alcohol (98% hydrolyzed polyvinyl acetate); and polyvinyl alcohol (74% hydrolyzed polyvinyl acetate).

FIG. 6A shows the effect of film-forming polymer on fragrance intensity for the polymers:

polyvinyl alcohol (98% hydrolyzed polyvinyl acetate); and

ADVANTAGE PLUS® (polymethyl methacrylate resin) with time (hours) on the X axis being from zero to 8 hours and log$_{10}$P fragrance intensity on the Y axis being from 4 up to 8 at a level of 1% polymer in a 95% ethyl alcohol solution and fragrance, with the fragrance being in an amount of 30% (thus, the resulting solution contains 1% polymer, 30% fragrance, 3.45% water and 65.55% ethyl alcohol). The fragrance is composed of:

25% C. P. FORMATE® having the structure:

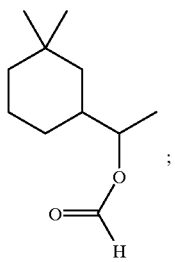

25% d-limonene having the structure:

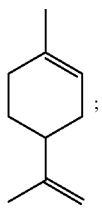

25% β-pinene having the structure:

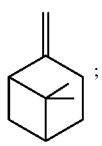

and

25% prenyl acetate having the structure:

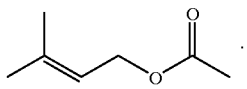

FIG. 6B is a graph showing the effect of the film-forming polymer on fragrance intensity having the same data as shown in the graph of FIG. 6A with the exception that the log$_{10}$P fragrance intensity is measured from a total GC chromatogram peak area count "normalized."

FIG. 6C is a graph showing the effect of film-forming polymer on fragrance intensity where the experimental polymer-fragrance formulation contains 1.5% PACIFIC LIGHT® and 0.5% LUVISKOL® VA 64 polymer defined according to the structure:

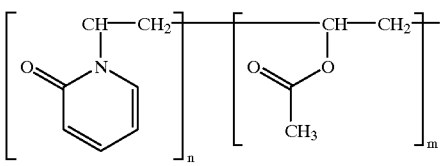

wherein n is 8 and m is 7 (registered trademark of International Specialty Products of Wayne, N.J.).

FIG. 6D is a graph showing the effect of film-forming polymer on fragrance intensity using a solution of 1% polyvinyl alcohol (98% hydrolyzed polyvinyl acetate) and 4% fragrance containing 25% of the compound having the structure:

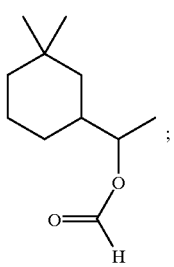

25% of the compound having the structure:

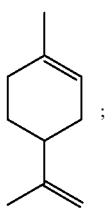

25% of the compound having the structure:

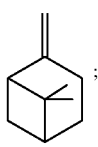

and
25% of the compound having the structure:

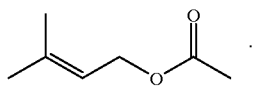

The Y axis shows $\log_{10}P$ fragrance intensity (measured as total GC peak area counts normalized) with the scale on the Y axis in the range of from −2 to +1.0 and the X axis of the graph being in time (hours) in the range of from zero up to 8 hours.

FIG. 6E is a graph showing the effect of film-forming polymer on fragrance intensity for a mixture containing 1% polyvinyl alcohol (98% hydrolyzed polyvinyl acetate), 14% PARFUM D'ETE® and 85% of 95% food grade ethanol (aqueous). The Y axis is $\log_{10}P$ fragrance intensity (total GC peak area counts) in the range of from 5 up to 9, and the X axis is time (hours) in the range of from zero up to 7 hours.

FIG. 6F is a graph showing the effect of film-forming polymer on fragrance intensity for the film produced from a solution containing 14% PARFUM D'ETE® and 1% polyvinyl alcohol (98% hydrolyzed polyvinyl acetate) using the same data as that used for FIG. 6E, except that on the Y axis the $\log_{10}P$ fragrance intensity is for total GC peak area counts normalized and the range of the $\log_{10}P$ fragrance intensity is from −2 to +1.

FIG. 7A is a graph showing the effect of $\log_{10}P$ (partition coefficient) on permeation using fragrances of differing partition coefficients dissolved at the rate of 5% in hydroxypropyl cellulose (molecular weight equals 100,000 daltons; permeability $10^{-7}$). The X axis measures $\log_{10}P$ in the range of 1–10. The range of the permeability on the Y axis is from zero to 7. The measurement temperature is 35° C.

FIG. 7B is a graph showing the effect of polymer molecular weight on d-limonene permeation rate with the polymers compared being:

(i) hydroxypropyl cellulose, molecular weight equals 100,000 daltons; and (ii) hydroxypropyl cellulose, molecular weight equals 370,000 daltons.

The Y axis shows weight loss (mg/cm²) in the range of from zero to 5, and the X axis shows time (minutes) in the range of from zero to 2,000.

FIG. 7C shows the effect of polymer molecular weight on d-limonene permeation rate where the polymers are as follows:

(i) polyvinyl alcohol (98% hydrolyzed polyvinyl acetate) (molecular weight range 13,000–23,000 daltons);

(ii) polyvinyl alcohol (98% hydrolyzed polyvinyl acetate) (molecular weight range 31,000–50,000 daltons); and (iii) polyvinyl alcohol (98% hydrolyzed polyvinyl acetate) (molecular weight range 124,000–186,000 daltons).

The weight loss (mg/cm²) is on the Y axis and is in the range of from zero to 5, and time is on the X axis and is in the range of from zero to 2,000.

FIG. 7D is a graph showing the effect of polymer structure on d-limonene permeation with the polymers used as follows:

(i) hydroxypropyl cellulose, molecular weight equals 100,000 daltons; and (ii) polyvinyl alcohol (98% hydrolyzed polyvinyl acetate) (molecular weight range 124,000–186,000 daltons).

The X axis shows time (minutes) in the range of from zero to 2,000. The Y axis shows weight loss (mg/cm²) in the range of from zero to 6.

FIG. 7E is a graph showing the effect of film on d-limonene diffusion for the following polymers:

(i) hydroxypropyl cellulose, molecular weight equals 100,000 daltons; and (ii) hydroxypropyl cellulose, molecular weight equals 370,000 daltons.

The weight loss (mg/cm²) is shown on the Y axis in the range of from zero to 250, and the time (minutes) is shown on the X axis in the range of from zero to 2,000.

FIG. 7F is another graph showing the effect of film on d-limonene diffusion with the polymer films being as follows:

(i) polyvinyl alcohol (98% hydrolyzed polyvinyl acetate) (molecular weight range 13,000–23,000 daltons);

(ii) polyvinyl alcohol (98% hydrolyzed polyvinyl acetate) (molecular weight range 31,000–50,000 daltons); and (iii) polyvinyl alcohol (98% hydrolyzed polyvinyl acetate) (molecular weight range 124,000–186,000 daltons).

The weight loss (mg/cm²) is shown on the Y axis in the range of from zero to 250, and time is shown on the X axis in the range of from zero to 2,000. The measurements are done at a temperature of 35° C.

FIG. 7G is a graph showing the effect of film on d-limonene diffusion using the polymers:

(i) hydroxypropyl cellulose, molecular weight equals 100,000 daltons; and (ii) polyvinyl alcohol (98% hydrolyzed polyvinyl acetate) (molecular weight range 124,000–186,000 daltons).

The weight loss (mg/cm²) is shown on the Y axis in the range of from zero to 250, and time (minutes) is shown on the X axis in the range of from zero to 2,000.

FIG. 7H is a graph showing permeation versus evaporation rates of hydrophobic aroma chemicals using the polymer, hydroxypropyl cellulose, molecular weight equals 100,000 daltons. The hydrophobic aroma chemicals are as follows:

(i) C.P. FORMATE® having the structure:

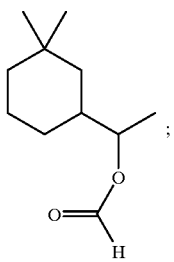

(ii) d-limonene having the structure:

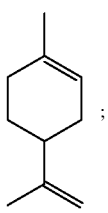

and (iii) β-pinene having the structure:

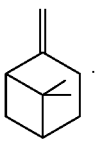

FIG. 7I is a graph showing the effect of $\log_{10}P$ on permeation using hydroxypropyl cellulose (molecular weight equals 100,000 daltons) as the polymer for the following aroma chemicals:

(i) ethyl tiglate ($\log_{10}P=2$; vapor pressure=1.8); and
(ii) β-pinene ($\log_{10}P=4.6$; vapor pressure 2.2).

The Y axis shows weight loss (mg/cm$^2$) in the range of from zero to 300, and the X axis shows time (minutes) in the range of from zero to 1,000.

FIG. 7J shows the effect of vapor pressure on evaporation rate for the following aroma chemicals:

(i) C.P. FORMATE® having the structure:

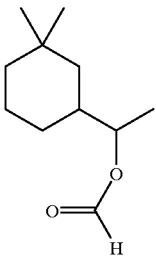

($\log_{10}P=3.9$; vapor pressure=0.1);
(ii) d-limonene having the structure:

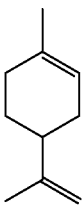

($\log_{10}P=4.4$; vapor pressure=1.4); and
(iii) β-pinene having the structure:

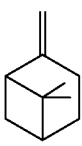

($\log_{10}P=4.6$; vapor pressure=2.2).

The weight loss (mg/cm$^2$) is shown on the Y axis in the range of from zero to 400, and time (minutes) is shown on the X axis in the range of from zero to 2,000.

FIG. 7K is a graph showing the effect of vapor pressure on permeation rate using hydroxypropyl cellulose (molecular weight=100,000 daltons) as the polymer at a temperature of 35° C. The following aroma chemicals dissolved at a level of 4% in the polymer are measured:

(i) C.P. FORMATE® having the structure:

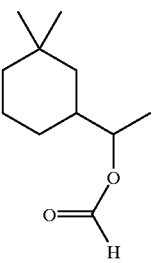

($\log_{10}P=3.9$; vapor pressure=0.1);
(ii) d-limonene having the structure:

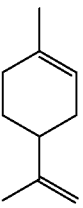

($\log_{10}P=4.4$; vapor pressure=1.4); and
(iii) β-pinene having the structure:

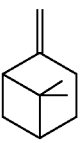

($\log_{10}P=4.6$; vapor pressure 2.2).

The weight loss (mg/cm$^2$) is shown on the Y axis in the range of from zero to 6, and time (minutes) is shown on the X axis in the range of from zero to 2,000.

FIG. 8 is a perspective of a finishing belt produced according to our invention, having coated thereon the film of our invention.

Figure 9:
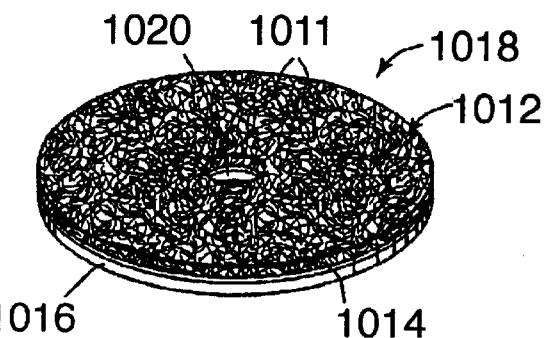

FIG. 9 is a perspective view of a surface finishing disk produced in accordance with our invention, containing the coating of our invention.

Figure 10:
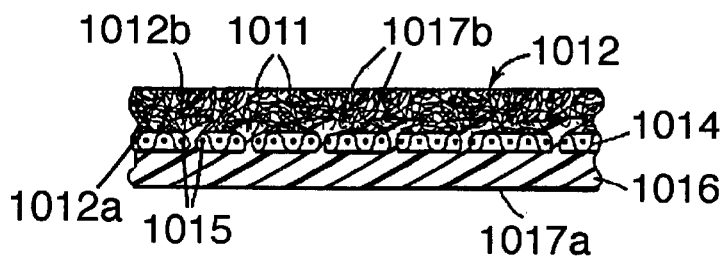

FIG. 10 is an enlarged sectional view of a segment of the surface finishing belt of FIG. 8 taken at line 10—10 of FIG. 8.

Figure 11:
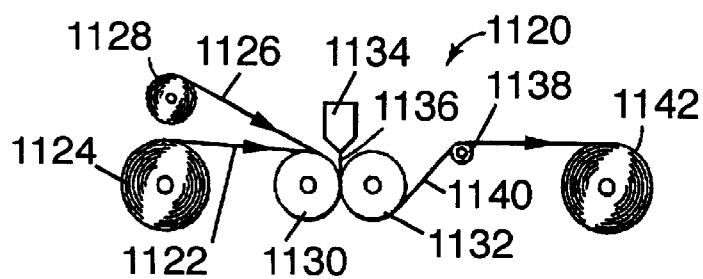

FIG. 11 is a schematic diagram depicting a method for manufacturing a surface finishing article according to our invention, but also using the technique of U.S. Pat. No. 5,573,844 issued on Nov. 12, 1996, the specification for which is incorporated by reference herein.

DETAILED DESCRIPTION OF THE DRAWINGS

Referring to FIGS. 1A, 1B and 1C the polymeric film or polymeric-gel film located on the substantially planar, solid or semi-solid support is shown by reference numeral 10. The planar solid or semi-solid support (e.g., woven or non-woven fabric, plywood or the human epidermis) is shown by reference numeral 13, and the surface of the planar solid or semi-solid support 13 juxtaposed with the polymeric/fragrance containing film is shown by reference numeral 14. Solvent evaporation from the film immediately after coating is shown by reference numeral 16a. The continuing solvent evaporation is shown by reference numerals 16b and then 16c. Perfume permeation from the film reservoir (shown by reference numerals 12a, 12b and 12c) through the permeation region of the polymer film (shown by reference numerals 11a, 11b and 11c) is shown by reference numerals 15a, 15b and 15c.

Referring to FIG. 1D, the reservoir region of the polymer 17 immediately adjacent the planar solid or semi-solid support 13 contains fragrance at concentration $C_0$. Adjacent the reservoir region 17 is permeation region 18 containing a low concentration of the fragrance, the concentration being variable from $C_m(0)$ to $C_m(1)$. That part of the graph of fragrance concentration in the reservoir region 17 is indicated by reference numeral 100a. That part of the fragrance concentration located in the permeation region of the polymer film is indicated by reference numeral 100b. As the fragrance leaves the permeation region into the environment surrounding the permeation region 19, the concentration is at $C_{(1)}$. The graph of FIG. 1D has concentration on the Y axis (indicated by reference numeral 190) and distance (including membrane thickness L) located on the X axis indicated by reference numeral 180.

Referring to FIG. 2, the X axis shows time indicated by the symbol θ, and the Y axis shows rate of aroma release indicated by reference numeral 21. The X axis is indicated by reference numeral 22. The lag effect zone is indicated by reference numeral 24; the steady state zone is indicated by reference numeral 25; and the exponential decline zone (first order release) is indicated by reference numeral 26. The overall graph is indicated by reference numeral 23. Initially, the rate of aroma release has a steep increase (lag effect zone) indicated by reference numeral 23a, followed by a steady state evolution indicated by reference numeral 23b, followed by an exponential decline indicated by reference numeral 23c.

Referring to FIG. 3A, polymer from holding vessel 31 optionally heated using heating element 374 is fed through line 33 past control valve 34 into vessel 37 optionally heated by heating element 370. Simultaneously, alcohol (ethyl alcohol) and/or water as polymer solvent held in vessel 32 is fed through line 35 past control valve 36 into vessel 37 where the polymer and alcohol and/or water are mixed and optionally heated using heating element 370. Fragrance component α held in vessel 301 is passed through line 363 past control valve 308 into fragrance mixing tank 309. Fragrance component β held in vessel 302 is passed through line 362 past control valve 307 into fragrance vessel 309. Fragrance component γ held in vessel 303 is passed through line 361 past control valve 306 into fragrance mixing vessel 309. Fragrance component δ held in tank 304 is passed through line 360 past control valve 305 into vessel 309. The fragrance components are mixed in tank 309 and optionally heated using heating element 372. The resulting fragrance mixture is conveyed through line 310 past valve 311 into vessel 312 where blending means 373 blends the fragrance with the polymer/alcohol and/or water mixture coming from vessel 37 through line 38 past control valve 39. The mixing or homogenizing vessel 312 optionally includes rotor/stator elements as indicated in detail in FIGS. 3C, 3D and 3E shown by reference numeral 312.

The resulting mixture is then passed through line 313 past control valve 314 into functional product formation vessel 315 whereat other functional ingredients (e.g., color materials and thickeners) from vessel 316 are passed through line 317 past valve 318. The resulting mixture is then passed through line 319 past valve 320 and spread on the solid or semi-solid support at location 321. Solvent 323 is evaporated at location 322 and the material functions in evolving fragrance at location 324, the fragrance being indicated by reference numeral 325. The apparatus and process of FIG. 3A can be used in conjunction with electronic program controller 381 as shown in FIG. 3B. Electronic program controller 381 uses marketing input information from source 380 via control line 380c feeding information into the program electronic controller 381 and controlling the apparatus and process as illustrated in FIG. 3A via control lines. Thus, the apparatus and process shown in schematic form in FIG. 3A is also shown in schematic form in FIG. 3B as associated with the electronic program controller (computer mechanism) via control lines.

More specifically, the control of fragrance material from containers 301, 302, 303 and 304 into vessel 309 past control valves 305, 306, 307 and 308 are controlled via control lines 305c, 306c, 307c and 308c. The rate of heating the fragrance in vessel 309 is controlled via control line 307 which controls heating element 372. The heat input to polymer material contained in vessel 31 using heating element 374 is controlled via control line 374c. The heat input to solvent vessel (containing ethanol and/or water) in vessel 32 using heating element 371 is controlled through control line 371c. The rate of flow of polymer into the polymer/solvent mixing vessel 37 through line 33 past valve 34 is controlled via valve control line 34c. By the same token, the rate of flow of solvent into the polymer/solvent vessel 37 is controlled through control valve 36 via control line 36c. The rate of heat input into the polymer/solvent vessel 37 using heating element 370 is controlled via control line 370c. The rate of flow of fragrance blend into homogenizing apparatus 312 through line 310 past valve 311 is controlled via control line 311c, and the energy of mixing and/or homogenization using mixer 373 is controlled via control line 373c. The rate of feed of polymer/solvent mixture into homogenizing apparatus 312 past valve 39 through line 38 is controlled via control line 39c. The rate of flow of resulting polymer/fragrance/solvent mixture to functional product formation location 315 through line 313 past control valve 314 is controlled via control line 314c. The rate of input of functional ingredients from vessel 316 to location 315 (functional product formation) through line 317 past valve 318 is controlled via control line 318c. All control lines are then fed through main control line 381c to electronic program control apparatus 381.

Referring to FIGS. 4A and 4B, fluid 46 is located in jar 44. Jar 44 has sidearm 45. The fluid 46 reaches fluid level 47. Directly in line with fluid level 47 is membrane 41. The diffusion membrane 41 is held in place with flanges 43 and jar lip 42, using bolts 401a and 401b which secures the flange in place. The sidearm 45 is closed using closure 49. The permeability apparatus is shown using reference numeral 40. The FRAGRANCE PERMEABILITY TEST is based on the use of the apparatus of FIGS. 4A and 4B. The weight of membrane 41 is taken, initially, before being placed within the flange 43 and the jar lip 42. Substance 46 for which the permeability is to be measured is placed into jar 44 to fluid level 47. The apparatus containing fluid 46 remains in place for a fixed period of time. At the end of that period of time, bolts 401a and 401b as well as 401c are loosened, the flange 43 removed and membrane 41 is removed and weighed, thereby gathering sufficient data to determine the permeability of the particular substance 46.

Referring to FIGS. 4C and 4D, FIGS. 4C and 4D set forth the fragrance diffusion evaluation system for determining the diffusivity and permeability of fragrance materials used in the practice of our invention. The test samples on blotters indicated by reference numeral 1001 are supported by support 1002 gin container 1003 having opening 1004 to the atmosphere. Air flow through line 1010 is supplied from air supply 1005 through tube 1006, having pressure gauge 1007 measuring the air flow. Container 1003 has side wall 1012 through which temperature probe 1009 is located. Temperature probe 1009 is attached to temperature monitor 1008. Container 1003 has base 1001. The overall apparatus is indicated by reference numeral 1000. FIG. 4D sets forth a top view of the apparatus of FIG. 4C showing the use of two tandem chambers 1003a and 1003b. Container 1003a is supplied with air flow through tube 1010a having pressure gauge 1007b in the air flow line. Container 1003b is supplied with air flow through tube 1010b with pressure gauge 1007a in its line. Air supply from location 1005 supplies air through line 1006a having pressure gauge 1007 in the line to measure air flow. The air flow is then split between line 1006b (for air flowing into container 1003a) and line 1006c (for air flowing to container 1003b). Temperature probe 1009a is used for container 1003a, and temperature probe 1009b is used for container 1003b. Temperature probe 1009b is attached to temperature monitor 1008b. Temperature probe 1009a is attached to temperature monitor 1008a. Container 1003a has opening 1004a at the top of same. Container 1003b has opening 1004b at the opening thereof. The overall apparatus having tandem containers for testing purposes is indicated by reference numeral 1000'.

The system shown in FIGS. 4C and 4D has as its primary purpose the simultaneous evaluation of an air freshener's (for example) performance for its hedonics, intensity, volatile content and weight loss as a function of time in a controlled environment of temperature and air mixing. The fragrance diffusion evaluation system is a midway station between a laboratory system that allows only analytical measurements and a full scale test of odor performance in a specially designed room that allows only sensory testing.

The fragrance diffusion evaluation system provides a controlled environment that allows for both sensory and analytical measurements of a fragrance's performance at low cost.

The fragrance diffusion evaluation system, shown in FIGS. 4C and 4D, comprises a cylinder having a height of between about 50 and about 75 cm, a radius of between about 15 and 30 cm and a volume of between about 0.1 and 0.2 m$^3$. The interior is coated with aluminum foil to ensure that no fragrance absorbs into the walls. The air flow is provided by a tube through the side between about 3 and about 10 cm from the bottom extending to the center of the chamber. The temperature is continuously monitored by a gauge located between about 10 and about 30 cm from the bottom. An opening with a diameter of between 15 and 30 cm is at the top of the cylinder to allow air flow and odor intensity testing. The air flow is, on average, between about 900 and 1,000 ml per minute. This air flow replaces the whole volume of the fragrance diffusion evaluation system with fresh air every 2 hours. The air flow through the chamber is constant at a pressure of between about 0.5 and 2 psig.

Referring to FIG. 5A, reference numeral 507 is for ethyl tiglate contained in the carnauba wax film. Reference numeral 508 is for the graph of ethyl tiglate for weight loss versus time, showing the permeability of carnauba wax to ethyl tiglate. Reference numeral 506 shows the data points for β-pinene in the carnauba wax film. Reference numeral 510 shows data points for ethyl tiglate without being entrapped in any control release system such as carnauba wax. Reference numeral 509 shows data points for the β-pinene control in the absence of carnauba wax. Reference numeral 511 sets forth the graph of unentrapped ethyl tiglate. Reference numeral 512 sets forth the graph of unentrapped β-pinene. The Y axis showing weight loss is indicated by reference numeral 505. The X axis showing time in minutes is indicated by reference numeral 504.

Referring to FIG. 5B, reference numeral 562 indicates data points for β-pinene contained in a film composed of hydroxypropyl cellulose. Reference numeral 564 indicates data points for β-pinene not contained in any polymer, but merely showing the evaporation rate of the β-pinene. Reference numeral 569 shows the standard deviation for the data points for β-pinene without being contained in hydroxypropyl cellulose. Reference numeral 563 shows the data points for ethyl tiglate contained in hydroxypropyl cellulose. Reference numeral 565 sets forth the data points for ethyl tiglate not being contained in any polymer and showing the evaporation rate of ethyl tiglate. Reference numeral 567 sets forth the graph showing the permeability of ethyl tiglate through hydroxypropyl cellulose. Reference numeral 568 sets forth the graph showing the evaporation of ethyl tiglate (without being contained in any polymer). Reference numeral 566 sets forth the graph showing the evaporation of β-pinene without being present in any polymer. The X axis is indicated by reference numeral 561 showing time in minutes, and the Y axis is indicated by reference numeral 560 showing weight loss in $$\frac{mg - mm}{cm^2}.$$

Referring to FIG. 5C, reference numeral 552 shows the data points for ethyl tiglate contained in polyvinyl alcohol (98% hydrolyzed polyvinyl acetate). Reference numeral 553 sets forth the data points for β-pinene contained in the polyvinyl alcohol film (98% hydrolyzed polyvinyl acetate) Reference numeral 554 sets forth the data points for ethyl tiglate not contained in polyvinyl alcohol and merely shows the evaporation rate of the ethyl tiglate. Reference numeral 555 sets forth the data points for β-pinene not being contained in any polyvinyl alcohol, but merely showing the evaporation rate of the β-pinene. Reference numeral 557 sets forth the graph showing the evaporation rate of β-pinene not being contained in any polyvinyl alcohol. Reference numeral 559 sets forth the standard deviation for the data points for ethyl tiglate and β-pinene not being contained in any polyvinyl alcohol. The X axis for time (minutes) is shown by reference numeral 551. The Y axis for weight loss $$\left(\frac{mg - mm}{cm^2}\right)$$

is shown by reference numeral 560.

Referring to FIG. 5D, which shows the effect of $\log_{10}P$ on permeation rate using polyvinyl alcohol (98% hydrolyzed polyvinyl acetate). The points indicated by reference numeral 515 are for ethyl tiglate, and the graph indicated by reference numeral 518 is for ethyl tiglate. The points indicated by reference numeral 516 are for β-pinene, and the graph indicated by reference numeral 517 is for β-pinene. The Y axis for weight loss is indicated by reference numeral 520, and the X axis for time is indicated by reference numeral 519.

Referring to FIG. 5E, showing the effect of $\log_{10}P$ on permeation rate using polyvinyl alcohol (74% hydrolyzed polyvinyl acetate), the points indicated by reference numeral 521 are for ethyl tiglate contained in the polyvinyl alcohol film. The points indicated by reference numeral 522 are for ethyl tiglate alone in the absence of a polymeric film. The points indicated by reference numeral 523 are for β-pinene contained in the polyvinyl alcohol film. The points indicated by reference numeral 524 are for β-pinene not contained in any polymer. The graph indicated by reference numeral 525 is for ethyl tiglate not contained in any polymeric film. The graph indicated by reference numeral 526 is for β-pinene not contained in any polymeric film. Weight loss $$\left(\frac{mg-mm}{cm^2}\right)$$

on the Y axis is indicated by reference numeral 528. Time (minutes) is indicated on the X axis by reference numeral 527.

Referring to FIG. 5F, FIG. 5F is an enlargement of graphs showing the points 521 and 523 in FIG. 5E.

Referring to FIG. 5F, the points indicated by reference numeral 529 are for ethyl tiglate, and the graph indicated by reference numeral 531 is for ethyl tiglate. The points indicated by reference numeral 530 are for β-pinene, and the graph indicated by reference numeral 532 is for β-pinene.

Referring to FIG. 5G, which shows the permeation of various aroma chemicals through carboxymethyl cellulose, the points indicated by reference numeral 535 are for ethyl tiglate dissolved in the carboxymethyl cellulose polymer. The points indicated by reference numeral 536 are for ethyl tiglate in the absence of carboxymethyl cellulose polymer. The points indicated by reference numeral are 537 are for aldehyde C-8 in the presence of the carboxymethyl cellulose polymer. The points indicated by reference numeral 538 are for β-pinene dissolved in the carboxymethyl cellulose polymer. The points indicated by reference numeral 539 are for β-pinene in the absence of any polymer. The graph indicated by reference numeral 542 is for ethyl tiglate in the absence of any polymer. The graph indicated by reference numeral 543 is for β-pinene in the absence of any polymer.

The points 535, 537 and 538 are presented graphically in the enlargement graph shown in FIGS. 5–G(A).

Referring again to FIG. 5G, the Y axis indicating weight loss $$\left(\frac{mg-mm}{cm^2}\right)$$

is indicated by reference numeral 541. The X axis indicating time in minutes is indicated by reference numeral 540.

Referring to FIG. 5-G(A), the points indicated by reference numeral 544 are for ethyl tiglate, and the graph for ethyl tiglate is indicated by reference numeral 548. The points indicated by reference numeral 545 are for aldehyde C-8, and the graph for aldehyde C-8 is indicated by reference numeral 549. The points indicated by reference numeral 546 are for β-pinene, and the graph for β-pinene contained in the carboxymethyl cellulose is indicated by reference numeral 547.

FIG. 5H sets forth the effect of $\log_{10}P$ on the permeation rate of the aroma chemicals, ethyl tiglate and β-pinene, through "alginate" (described in detail at monograph number 240 on page 45 of THE MERCK INDEX, Twelfth Edition, published by Merck Research Laboratories Division of Merck & Company, Inc., Whitehouse Station, N.J., 1996, and incorporated by reference herein). "Alginate" is described in detail in U.S. Pat. No. 2,036,934, incorporated by reference herein.

Reference numeral 570 indicates data points for ethyl tiglate. The graph for ethyl tiglate is indicated by reference numeral 573. Reference numeral 571 indicates data points for β-pinene. The graph indicated by reference numeral 572 is for β-pinene contained in the "alginate." The X axis of the graph for time (minutes) is indicated by reference numeral 575. The Y axis of the graph for weight loss $$\left(\frac{mg-mm}{cm^2}\right)$$

is indicated by reference numeral 570.

Referring to FIG. 5I, the graph showing the permeation of ethyl tiglate through positively charged polymers, the data points indicated by reference numeral 576 are for POLYMER LK® (registered trademark of Amerchol Corporation of Edison, N.J.). The graph indicated by reference numeral 579 is the graph for POLYMER LK® containing the ethyl tiglate. The data points indicated by reference numeral 577 are for POLYMER LR-400® (registered trademark of Amerchol Corporation of Edison, N.J.). The graph indicated by reference numeral 578 is for the graph of POLYMER LR-400® containing the ethyl tiglate. POLYMER LK and POLYMER LR-400® are polymers defined according to the structure:

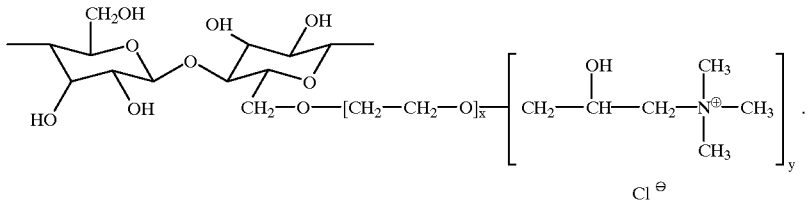

In the case of POLYMER LK®, x=8 and y=2. In the case of POLYMER LR-400®, x=6 and y=1. The overall permeation rate is $$5.8 \times 10^{-4} \left[\frac{mg-mm}{cm^2-min}\right].$$

FIG. 5J is a graph showing the permeation of ethyl tiglate through different film-forming polymers. The data points indicated by reference numeral 582 are for gelatin. The data points indicated by reference numeral 583 are for carboxymethyl cellulose. The data points indicated by reference numeral 584 are for hydroxypropyl cellulose. The data points indicated by reference numeral 585 are for polyvinyl alcohol (98% hydrolyzed polyvinyl acetate). The data points indicated by reference numeral 586 are for polyvinyl alcohol (74% hydrolyzed polyvinyl acetate). The data points indicated by reference numeral 587 are for ethyl tiglate in the absence of any polymer film. The graph indicated by reference numeral 589 is for ethyl tiglate alone and for ethyl tiglate in the presence of hydroxypropyl cellulose. Hydroxypropyl cellulose has no advantage in controllably releasing ethyl tiglate as do the other polymers. The X axis of the graph of FIG. 5J for time (minutes) is shown by reference numeral 701. The Y axis for weight loss $$\left(\frac{mg-mm}{cm^2}\right)$$

is shown by reference numeral 702. FIG. 5-J(A) is an enlargement of graphs for the data points 582, 583, 585 and 586. The graph indicated by reference numeral 591 is for carboxymethyl cellulose. The graph indicated by reference numeral 592 is for polyvinyl alcohol (98% hydrolyzed polyvinyl acetate). The graph indicated by reference numeral 590 is for polyvinyl alcohol (74% hydrolyzed polyvinyl acetate).

FIG. 5K is a graph showing permeation of β-pinene through positively charged polymers, POLYMER LK® and POLYMER LR-400®, described, supra. The data points indicated by reference numeral 533 are for polymer POLYMER LK®. The data points indicated by reference points 594 are for POLYMER LR-400®. The graph indicated by reference numeral 595 is the graph for POLYMER IR-400® containing the β-pinene. The graph indicated by reference numeral 596 is for the POLYMER LK® containing the β-pinene. The permeation rate for the graph indicated by reference numeral 595 is $$7.5 \times 10^{-5} \left[\frac{mg-mm}{cm^2-min}\right].$$

The permeation rate for the graph indicated by reference numeral 596 is $$3.9 \times 10^{-5} \left[\frac{mg-mm}{cm^2-min}\right].$$

FIG. 5L is a graph showing permeation of β-pinene through different film-forming polymers. The data points indicated by reference numeral 5001 are for gelatin. The data points indicated by reference numeral 5002 are for carboxymethyl cellulose. The data points indicated by reference numeral 5003 are for hydroxypropyl cellulose. The data points indicated by reference numeral 5004 are for polyvinyl alcohol (98% hydrolyzed polyvinyl acetate). The data points indicated by reference numeral 5005 are for polyvinyl alcohol (74% hydrolyzed polyvinyl acetate). The data points indicated by reference numeral 5006 are for β-pinene in the absence of any polymer. The graph indicated by reference numeral 5007 is for β-pinene in the absence of any polymer. The X axis indicating time (minutes) is indicated by reference numeral 703, and the Y axis for weight loss $$\left(\frac{mg-mm}{cm^2}\right)$$

is indicated by reference numeral 704.

FIG. 5-L(A) is an enlargement of the graphs containing data points 5002, 5003, 5004, 5005 and 5001. The graph for carboxymethyl cellulose (containing the β-pinene) is indicated by reference numeral 5010. The graph for polyvinyl alcohol (98% hydrolyzed polyvinyl acetate) is indicated by reference numeral 5008. The graph for gelatin is indicated by reference numeral 5009.

FIG. 5M is a graph of permeation versus evaporation rates of hydrophobic aroma chemicals using hydroxypropyl cellulose (molecular weight=100,000 daltons). The data points indicated by reference numeral 5011 are for C.P. FORMATE® (registered trademark of International Flavors & Fragrances Inc.) having the structure:

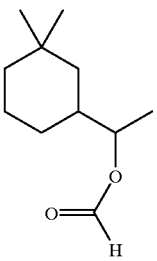

in the absence of any polymers. The data points indicated by reference numeral 5012 are for d-limonene having the structure:

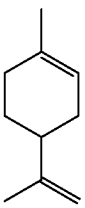

in the absence of any polymers. The data points indicated by reference numeral 5013 are for β-pinene in the absence of any polymers. The data points indicated by reference numeral 5014 are for C.P. FORMATE® in the presence of hydroxypropyl cellulose. The data points indicated by reference numeral 5015 are for d-limonene in the presence of hydroxypropyl cellulose. The data points indicated by reference numeral 5016 for β-pinene as dissolved in hydroxypropyl cellulose. The X axis, indicated by reference numeral 5020, is for time (minutes), and the Y axis indicated by reference numeral 5021 is for weight loss $$\left(\frac{mg-mm}{cm^2}\right).$$

The graph indicated by reference numeral 5017 is for β-pinene in the absence of any polymers (control). The graph indicated by reference numeral 5018 is for d-limonene (control) in the absence of any polymers. The graph indicated by reference numeral 5019 is for C.P. FORMATE® in the absence of any polymers.

FIG. 5N is a graph showing the effect of $\log_{10}P$ on permeation rate using hydroxypropyl cellulose. The data points indicated by reference numeral 5022 are for prenyl acetate having the structure:

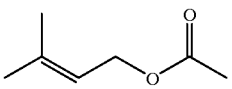

in the hydroxypropyl cellulose. The data points indicated by reference numeral 5023 are for ethyl tiglate. The data points indicated by reference numeral 5024 are for aldehyde C-8. The data points indicated by reference numeral 5025 are for β-pinene. The graph indicated by reference numeral 5026 is for prenyl acetate in hydroxypropyl cellulose. The graph indicated by reference numeral 5027 is for ethyl tiglate in hydroxypropyl cellulose. The graph indicated by reference numeral 5028 is for aldehyde C-8 in hydroxypropyl cellulose. The graph indicated by reference numeral 5029 is for β-pinene in hydroxypropyl cellulose. The X axis is for time (minutes) and is indicated by reference numeral 5030. The Y axis for weight loss in units of $$\left(\frac{mg-mm}{cm^2}\right)$$

is indicated by reference numeral 5031.

FIG. 5-O is a graph showing the effect of polymer structure on permeation using ethyl tiglate as the reference fragrance. The data points indicated by reference numeral 5032 are for gelatin. The data points indicated by reference numeral 5033 are for hydroxypropyl cellulose. The data points indicated by reference numeral 5034 are for carboxymethyl cellulose. The data points indicated by reference numeral 5035 are for polyvinyl alcohol (98% hydrolyzed polyvinyl acetate). The data points indicated by reference numeral 5036 are for polyvinyl alcohol (74% hydrolyzed polyvinyl acetate). The data points indicated by reference numeral 5037 are for ethyl tiglate alone in the absence of polymer. The graph indicated by reference numeral 5038 is the graph for both the control, ethyl tiglate in the absence of polymer, and for hydroxypropyl cellulose containing the ethyl tiglate. The X axis is for time (minutes) and is indicated by reference numeral 5039. The Y axis is for weight loss $$\left(\frac{mg-mm}{cm^2}\right)$$

and is indicated by reference numeral 5040.

FIG. 5-P is a graph, which is an enlargement of that section of FIG. 5-O containing the data points for gelatin, carboxymethyl cellulose, polyvinyl alcohol (98% hydrolyzed polyvinyl acetate) and polyvinyl alcohol (74% hydrolyzed polyvinyl acetate). The graph indicated by reference numeral 5045 is for polyvinyl alcohol (74% hydrolyzed polyvinyl acetate). The graph indicated by reference numeral 5046 is for gelatin. The graph indicated by reference numeral 5047 is for polyvinyl alcohol (98% hydrolyzed polyvinyl acetate) and for carboxymethyl cellulose. The X axis for time (minutes) is indicated by reference numeral 5048, and the Y axis for weight loss $$\left(\frac{mg-mm}{cm^2}\right)$$

is indicated by reference numeral 5049.

FIG. 5-Q is a graph showing the effect of polymer structure on permeation for β-pinene. The data points indicated by reference numeral 5050 are for hydroxypropyl cellulose. The data points indicated by reference numeral 5051 are for carboxymethyl cellulose. The data points indicated by reference numeral 5052 are for polyvinyl alcohol (98% hydrolyzed polyvinyl acetate). The data points indicated by reference numeral 5053 are for polyvinyl alcohol (74% hydrolyzed polyvinyl acetate). The graph indicated by reference numeral 5055 is for polyvinyl alcohol (98% hydrolyzed polyvinyl acetate) and for polyvinyl alcohol (74% hydrolyzed polyvinyl acetate). The graph indicated by reference numeral 5054 is for hydroxypropyl cellulose and for carboxymethyl cellulose. The X axis for time (minutes) is indicated by reference numeral 5056, and the Y axis for weight loss $$\left(\frac{mg-mm}{cm^2}\right)$$

is indicated by reference numeral 5057.

FIG. 6-A is a graph showing the effect of film forming polymer on fragrance intensity for the polymers polyvinyl alcohol (98% hydrolyzed polyvinyl acetate) and ADVANTAGE PLUS® (trademark of International Specialty Products) having the structure:

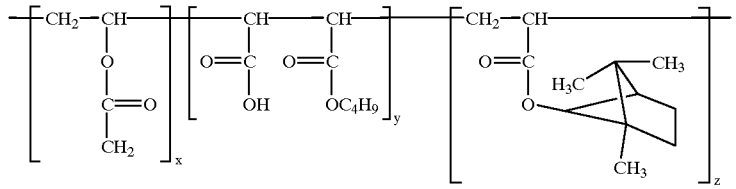

The data points indicated by reference numeral 603 are for the polyvinyl alcohol. The data points indicated by reference numeral 604 are for the ADVANTAGE PLUS®, and the data points indicated by reference numeral 605 are for the fragrance control in the absence of polymer, which fragrance control consists of equal parts of C.P. FORMATE®, d-limonene, β-pinene and prenyl acetate. The graph indicated by reference numeral 606 is the graph for the polymer/solvent/fragrance containing polyvinyl alcohol. The graph indicated by reference numeral 607 is for the system containing ADVANTAGE PLUS®/fragrance/solvent. The graph indicated by reference numeral 608 is for the control, that is, solvent plus fragrance, but in the absence of polymer. The X axis indicated by reference numeral 601 is for the time (hours). The Y axis of the graph indicated by reference numeral 602 shows $\log_{10}P$ of fragrance intensity (total GC peak area counts)

FIG. 6-B shows the effect of the film forming polymer on fragrance intensity and sets forth the same data as that set forth in FIG. 6A, except that the X axis represents $\log_{10}P$ fragrance intensity (total GC peak area counts normalized). The data points indicated by reference numeral 612 are for polyvinyl alcohol (98% hydrolyzed polyvinyl acetate). The data points indicated by reference numeral 613 are for systems containing ADVANTAGE PLUS® (together with solvent and fragrance). The data points indicated by reference numeral 614 are for systems containing solely fragrance and solvent but no polymer. The graph indicated by reference numeral 615 is the graph for the system: polyvinyl alcohol/solvent/fragrance. The graph indicated by reference numeral 616 is for the system: ADVANTAGE PLUS®/solvent/fragrance. The graph indicated by reference numeral 617 is for the system: fragrance/solvent (but no polymer). The X axis is shown by reference numeral 610 and represents time (hours). The Y axis is indicated by reference numeral 611 and represents $\log_{10}P$ fragrance intensity (total GC peak area counts normalized)

FIG. 6-C sets forth a graph showing the effect of film forming polymer on fragrance intensity. The data points indicated by reference numeral 622 are for the system: 1.5% PACIFIC LIGHT® Fragrance/0.5% LUVISKOL® VA 64 (having the structure:

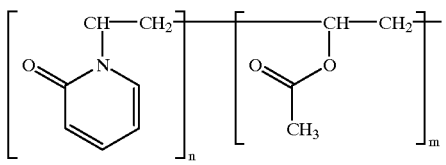

wherein n=8 and m=7)/98% food grade ethanol. The data points indicated by reference numeral 623 are for the system: 1.5% PACIFIC LIGHT® Fragrance/solvent (food grade ethanol) (in the absence of polymer). The graph indicated by reference numeral 624 is the graph for the system: 1.5% PACIFIC LIGHT® Fragrance/ 0.5% LUVISKOL® VA 64/98% food grade alcohol solvent. The graph indicated by reference numeral 625 is the graph for the system: 1.5% PACIFIC LIGHT® Fragrance/98.5% food grade alcohol. The Y axis sets forth $\log_{10}P$ fragrance intensity (total GC peak area counts) and is indicated by reference numeral 621. The X axis sets forth time (hours) and is indicated by reference numeral 620.

FIG. 6-D is a graph setting forth the effect of the film forming polymer on fragrance intensity with the fragrance being equal parts of C.P. FORMATE®, d-limonene, β-pinene and prenyl acetate. The data points indicated by reference numeral 632 are for the "control" system, to wit:4% fragrance:96% food grade alcohol solvent. The data points indicated by reference numeral 633 are for the system: 1% polyvinyl alcohol (98% hydrolyzed polyvinyl acetate)/4% fragrance/95% food grade alcohol. The graph indicated by reference numeral 634 is for the system: polyvinyl alcohol/fragrance/solvent. The graph indicated by reference numeral 635 is for the system: fragrance/solvent. The Y axis indicated by reference numeral 631 represents $\log_{10}P$ fragrance intensity (total GC peak area counts normalized). The X axis indicated by reference numeral 630 is for the time (hours).

FIG. 6-E sets forth the effect of the film forming polymer on fragrance intensity. The data points indicated by reference numeral 642 are for the system: 14% PARFUM D'ETE®/86% solvent (control) The data points indicated by reference numeral 643 are for the system: 14% PARFUM D'ETE® /1% polyvinyl alcohol (98% hydrolyzed polyvinyl acetate)/85% food grade alcohol solvent. The graph indicated by reference numeral 644 is for the system: 14% PARFUM D'ETE® /1% polyvinyl alcohol/85% food grade alcohol solvent. The graph indicated by reference numeral 645 is for the system: 14% PARFUM D'ETE® /86% food grade alcohol solvent (control). The Y axis indicated by reference numeral 641 represents $\log_{10}P$ fragrance intensity (total GC peak area counts). The X axis indicated by reference numeral 640 is for the time (hours).

FIG. 6-F sets forth the effect of the film forming polymer on fragrance intensity and shows essentially the same data as that set forth in FIG. 6-E. The data points indicated by reference numeral 654 are for the system: 14% PARFUM D'ETE® /86% food grade alcohol (control). The data points indicated by reference numeral 653 are for the system: 14% PARFUM D'ETE® /1% polyvinyl alcohol (98% hydrolyzed polyvinyl acetate)/85% food grade alcohol solvent. The graph indicated by reference numeral 655 is for the system: 14% PARFUM D'ETE® /1% polyvinyl alcohol/85% solvent. The graph indicated by reference numeral 654 is for the system: 14% PARFUM D'ETE® /86% food grade alcohol solvent (control). The Y axis indicated by reference numeral 651 represents $\log_{10}P$ fragrance intensity (total GC peak area counts normalized). The X axis indicated by reference numeral 650 is for the time (hours).

FIG. 7-A sets forth a graph showing the effect of $\log_{10}P$ on permeation for the polymer hydroxypropyl cellulose (molecular weight=100,000 daltons). The data points indicated by reference numeral 701 are for particular fragrance ingredients having particular values for $\log_{10}P$. For example, ethyl tiglate has a $\log_{10}P$ of 2.0, and β-pinene has a $\log_{10}P$ of 4.6. The graph indicated by reference numeral 702 is the graph showing permeability as a function of $\log_{10}P$ according to the equation: B=2·13 ($\log_{10}P$)+8·26, wherein B represents permeability measured in $[(mm\ thickness/cm^2\ area)\ seconds]10^{-7}$. The Y axis sets forth permeability in terms of $[(mm\ thickness/cm^2\ area)\ seconds]10^{-7}$ and is indicated by reference numeral 705. The X axis indicates $\log_{10}P$ wherein P is the partition coefficient of the fragrance ingredient between n-octanol and water. The data for the graph of FIG. 7-A is run at 35° C.

FIG. 7-B is a graph showing the effect of polymer molecular weight on d-limonene permeation rate. The data points indicated by reference numeral 710 are for hydroxypropyl cellulose having a molecular weight of 100,000 daltons. The data points indicated by reference numeral 711 are for hydroxypropyl cellulose having a molecular weight of 370,000 daltons. The graph indicated by reference numeral 712 is for the system: hydroxypropyl cellulose (molecular weight=370,000 daltons)—4% d-limonene. The graph indicated by reference numeral 713 is for the system: hydroxypropyl cellulose (molecular weight=100,000 daltons)—4% d-limonene.

FIG. 7C is a graph showing the effect of polymer molecular weight on d-limonene permeation rate. The data points indicated by reference numeral 721 are for polyvinyl alcohol (98% hydrolyzed polyvinyl acetate) (molecular weight range=13,000–23,000 daltons). The data points indicated by reference numeral 722 are for polyvinyl alcohol (98% hydrolyzed polyvinyl acetate) (molecular weight range=31,000–50,000 daltons). The data points indicated by reference numeral 723 are for polyvinyl alcohol (98% hydrolyzed polyvinyl acetate) (molecular weight range=124,000–186,000 daltons) The graph indicated by reference numeral 726 is the graph for the system: polyvinyl alcohol (molecular weight range=13,000–23,000 daltons)/4% d-limonene. The graph indicated by reference numeral 725 is for the system: polyvinyl alcohol (molecular weight range=31,000–50,000 daltons)/4% d-limonene. The graph indicated by reference numeral 724 is for the system: polyvinyl alcohol (molecular weight range=124,000–186,000 daltons)/4% d-limonene. The Y axis is indicated by reference numeral 727 and is for weight loss $$\left(\frac{mg-mm}{cm^2}\right).$$

The X axis indicated by reference numeral 726' is for time (minutes).

FIG. 7D is a graph showing the effect of polymer structure on d-limonene permeation. The data points indicated by reference numeral 730 are for hydroxypropyl cellulose (molecular weight=100,000 daltons). The data points indicated by reference numeral 731 are for polyvinyl alcohol (98% hydrolyzed polyvinyl acetate) (molecular weight range=124,000–186,000 daltons). The graph indicated by reference numeral 732 is the graph for the system: hydroxypropyl cellulose/4% d-limonene. The graph indicated by reference numeral 733 is for the system: polyvinyl alcohol/4% d-limonene. The X axis is indicated by reference numeral 735 and is for time (minutes). The Y axis is indicated by reference numeral 734 and is for weight loss in terms of $$\left(\frac{mg-mm}{cm^2}\right).$$

FIG. 7E is a graph showing the effect of film on d-limonene diffusion. The data points indicated by reference numeral 742 are for hydroxypropyl cellulose (molecular weight=100,000 daltons). The data points indicated by reference numeral 741 are for hydroxypropyl cellulose (molecular weight=370,000 daltons) The data points indicated by reference numeral 740 are for the control, that is, for d-limonene in the absence of any polymer. The graph indicated by reference numeral 743 is the graph for d-limonene (in the absence of any polymer). The X axis is indicated by reference numeral 744 and is for the time in minutes. The Y axis is indicated by reference numeral 745 and is for weight loss in terms of $$\left(\frac{mg-mm}{cm^2}\right).$$

FIG. 7-F is a graph showing the effect of film on d-limonene diffusion. The data points indicated by reference numeral 751 are for polyvinyl alcohol (98% hydrolyzed polyvinyl acetate) (molecular weight range=13,000–23,000 daltons). The data points indicated by reference numeral 752 are for polyvinyl alcohol (98% hydrolyzed polyvinyl acetate) (molecular weight range=31,000–50,000 daltons). The data points indicated by reference numeral 753 are for polyvinyl alcohol (98% hydrolyzed polyvinyl acetate) (molecular weight range=124,000–186,000 daltons). The data points indicated by reference numeral 750 are for d-limonene in the absence of any polymers. The graph indicated by reference numeral 754 is for the system d-limonene in the absence of any polymers. The X axis is indicated by reference numeral 755 and is for time (minutes). The Y axis is indicated by reference numeral 756 and is for weight loss in terms of $$\left(\frac{mg-mm}{cm^2}\right).$$

FIG. 7-G is a graph of the effect of film on d-limonene diffusion at a temperature of 35° C. The data points indicated by reference numeral 760 are for hydroxypropyl cellulose having a molecular weight of 100,000 daltons. The data points indicated by reference numeral 761 are for polyvinyl alcohol (98% hydrolyzed polyvinyl acetate) (molecular weight range=124,000–186,000 daltons). The data points indicated by reference numeral 762 are for d-limonene in the absence of any polymers. The graph indicated by reference numeral 765 is for d-limonene in the absence of any polymers. The X axis is indicated by reference numeral 763 and is for time (minutes). The Y axis is indicated by reference numeral 764 and is for weight loss in terms of $$\left(\frac{mg-mm}{cm^2}\right).$$

FIG. 7-H is a graph showing permeation versus evaporation rates of different hydrophobic aroma chemicals using the polymer, hydroxypropyl cellulose having a molecular weight of 100,000 daltons, the data being taken at a temperature of 35° C. The data points indicated by reference numeral 770 are for the system: C.P. FORMATE® alone in the absence of any polymer (control). The data points indicated by reference numeral 771 are for d-limonene taken alone in the absence of any polymer (control). The data points indicated by reference numeral 772 are for β-pinene taken alone in the absence of any polymer (control) The data points indicated by reference numeral 773 are for the system: hydroxypropyl cellulose/4% C.P. FORMATE®. The data points indicated by reference numeral 774 are for the system: hydroxypropyl cellulose/4% d-limonene. The data points indicated by reference numeral 775 are for the system: hydroxypropyl cellulose/4% β-pinene. The graph indicated by reference numeral 776 is for β-pinene taken alone in the absence of any polymer. The graph indicated by reference numeral 777 is for d-limonene taken alone in the absence of any polymer. The graph indicated by reference numeral 778 is for C.P. FORMATE® taken alone in the absence of any polymer. The X axis, indicated by reference numeral 779, is for time (minutes). The Y axis, indicated by reference numeral 780, is for weight loss in terms of $$\left(\frac{mg-mm}{cm^2}\right).$$

FIG. 7-I sets forth a graph showing the effect of $\log_{10}P$ on permeation using hydroxypropyl cellulose (molecular weight=100,000 daltons) with measurements at 35° C. The data points indicated by reference numeral 781 are for the system: hydroxypropyl cellulose/4% ethyl tiglate. The data points indicated by reference numeral 782 are for ethyl tiglate alone in the absence of any polymer. The data points indicated by reference numeral 783 are for the system: hydroxypropyl cellulose/4% β-pinene. The data points indicated by reference numeral 784 are for β-pinene taken alone in the absence of any polymer (control). The graph indicated by reference numeral 786 is for the systems: hydroxypropyl cellulose/4% ethyl tiglate and ethyl tiglate taken alone in the absence of polymer. The graph indicated by reference numeral 785 is for β-pinene taken alone in the absence of polymer. The X axis is indicated by reference numeral 787 and is for time (minutes). The Y axis is indicated by reference numeral 788 and is for weight loss $$\left(\frac{mg-mm}{cm^2}\right).$$

FIG. 7-J is a graph setting forth the effect of vapor pressure on evaporation rate for various aroma chemicals. The data points indicated by reference numeral 790 are for C.P. FORMATE®. The data points indicated by reference numeral 791 are for d-limonene. The data points indicated by reference numeral 792 are for β-pinene. The graph indicated by reference numeral 793 is for β-pinene. The graph indicated by reference numeral 794 is for d-limonene. The graph indicated by reference numeral 795 is for C.P. FORMATE®. The X axis is indicated by reference numeral 796 and is for time (minutes). The Y axis is indicated by reference numeral 797 and is for weight loss $$\left(\frac{mg-mm}{cm^2}\right).$$

FIG. 7-K is a graph showing the effect of vapor pressure on permeation rate using the polymer hydroxypropyl cellulose (molecular weight 100,000 daltons) with measurements being made at a temperature of 35° C. The data points indicated by reference numeral 801 are for the system: hydroxypropyl cellulose/4% C.P. FORMATE® . The data points indicated by reference numeral 802 are for the system: hydroxypropyl cellulose/4% d-limonene. The data points indicated by reference numeral 803 are for the system: hydroxypropyl cellulose/4% β-pinene. The graph indicated by reference numeral 804 is for the system: hydroxypropyl cellulose/4% d-limonene. The graph indicated by reference numeral 805 is for the system: hydroxypropyl cellulose/4% β-pinene. The graph indicated by reference numeral 806 is for the system: hydroxypropyl cellulose/4% C.P. FORMATE®. The X axis is indicated by reference numeral 807 and is for time (minutes). The Y axis is indicated by reference numeral 808 and is for weight loss $$\left(\frac{mg-mm}{cm^2}\right).$$

Referring to FIGS. 8, 9, 10 and 11, the surface finishing article according to our invention in the form of an endless belt 1010 (FIG. 8) is shown. A three-dimensional non-woven web 1012 and a woven stretch resistant reinforcing fabric 1014 are components of the belt 1010. The non-woven web 1012 includes an inner first major surface 1012(*a*) and an outer or second major surface 1012(*b*) with the second surface 1012(*b*) being the working surface of the belt 1010 (see FIG. 10). The reinforcing fabric 1014 preferably comprises a woven material having a plurality of openings therethrough (generally indicated at 1015). Fabric 1014 is applied against the first surface 10129*a*) of the non-woven layer 1012. The flexible polymer layer 1016 (produced according to the process of Example II, infra) extends and is coextensive with the major surface of the fabric 1014 forming exposed surface 1017(*a*) and providing a drive surface of belt 1010 which in use would be carried on drive rollers and supported there between on a platen of a surface finishing machine (not shown). Exposed surface 1017(*a*) is preferably a low friction surface to avoid heat buildup between it and the surface of the platen. Portions 1017(*b*) (FIG. 10) of the polymer layer 1016 extend through openings in the fabric 1014 to form discrete bonding areas with fibers 1011 along the first major surface 1012(*a*) of non-woven layer 1012.

The articles, which are embodiments of the present invention, can also be provided in the form of disks such as disk 1018 shown in FIG. 9. Disk 1018 may include a central opening 1020 to facilitate mounting. Except for its converted external shape, the internal structure of the disk 1018 is identical to that of belt 1010 of FIG. 8 including a non-woven layer 1012, a woven material 1014 and a polymeric material (produced according to Example II, infra) 1016 as described above. Surface finishing articles of our invention also comprise surface finishing pads (not shown) having the above-described feature which may be cut or converted into any of a variety of shapes, e.g., rectangular, square, circular, oval, etc. All such surface finishing articles having the described features will be understood as within the scope of the present invention. Further details of the components of the surface finishing articles of our invention are provided below.

The non-woven web comprises a lofty, open, low-density, fibrous, non-woven web made of suitable synthetic fiber such as nylon, polyester and the like. The web preferably is capable of withstanding the temperatures at which impregnating resins and adhesive binders are cured without deterioration. The fibers of the web are preferably tensilized and crimped, but may also be contnuous filaments formed by a spunbond process such as that described in U.S. Pat. No. 4,227,350 to Fitzer (the specification for which is incorporated by reference herein), for example. Fibers which are satisfactory for use in the non-woven web are between about 20 and about 100 mm and preferably between about 40 and about 65 mm in length and have a denier ranging from about 1.5 to about 500 and, preferably, from about 15 to about 100. It is contemplated that fibers of mixed denier can be used in the manufacture of a non-woven portion 1012 in order to obtain a desired surface finish. The use of larger fibers is also contemplated to permit the inclusion of larger abrasive particles within the articles of this aspect of our invention. Those skilled in the art will understand that the invention is not limited by the nature of the fibers employed or by their respective lengths, denier and the like.

The non-woven web is readily formed on a "Rando webber" machine (commercially available from Rando Machine Company, New York, N.Y., U.S.A.) or may be formed by other conventional carding processes. Where a spunbond-type non-woven material is employed, the filaments may be of substantially larger diameter, for example, up to 2 mm or more in diameter. The use of larger diameter fibers permits the employment of larger abrasive particles in the finished aricle. Useful non-woven webs preferably have a weight per unit area at least about 100 g/m$^2$, and more preferably, about 250 g/m$^2$. Lesser amounts of fiber within the non-woven web will provide articles having somewhat shorter commercial work lives. The foregoing fiber weights typically will provide a web, before needling or impregnation, having a thickness from about 6 to about 75 mm, and preferably, about 25 mm. Commercially available non-woven suitable for use in the invention include those identified in the Examples of U.S. Pat. No. 5,573,844 issued on Nov. 12, 1996 (Donovan, et al), the specification for which is incorporated by reference herein.

The non-woven web 1012 may optionally be further reinforced and consolidated by needle tacking, treatment which mechanically strengthens the non-woven web by passing barbed needles therethrough. During this treatment, the needles pull the fibers of the web with them while they pass through the non-woven web so that, after the needle has retrated, individual collections of fibers of the web are oriented in the thickness direction of the non-woven fabric. The amount or degree of needle tacking may include the use of about 8 to about 20 needle penetrations per square cm of web surface when 15×18×25×3.5 RB, F20 6-32-5.5B/3B/2E/L90 needles (commercially available from Foster Needle Company, Manitowoc, Wis., U.S.A.) are used. Needle tacking is readily accomplished by the use of a conventional needle loom which is commercially available from, for example, Dilo, Inc. of Charlotte, N.C., U.S.A.

Following the optional needle tacking step, the non-woven web is impregnated either with a resin-abrasive slurry or a resin binder (e.g., without abrasive particles) depending upon the required aggressiveness of the finished article. The non-woven web is thoroughly saturated with the resin-abrasive slurry or the resin binder using any of a number of conventional application techniques, such as spray coating, dip-coating or roll coating, using a two-roll coater, for example. The preferred resins for use in coating the non-woven web also include the fragrance materials as set forth herein. The preferred resins for use in coating the non-woven web are also those which, upon curing, will be relatively hard and which will provide firm bonding of the constituent fibers to one another. Exemplary of resins that are useful in this aspect of the present invention include but are not limited to phenolic resins, aminoplast resins having pendant α, β-unsaturated carbonyl groups, urethane resins, epoxy resins, ethylenically unsaturated resins, acrylated isocyanurate resins, urea-formaldehyde resins, isocyanurate resins, acrylated urethane resins, acrylated epoxy resins, bismaleimide resins, fluorine-modified epoxy resins and combinations thereof. Catalyst and/or curing agents may be added to the binder precursor to initiate and/or eliminate polymerization. Preferably, the binders used in this aspect of our invention are phenolic resins, such as resole and novolac resins, described in Kirk-Othmer, *Encyclopedia of Chemical Technology*, Third Edition, John Wiley and Sons, 1981, New York, Volume 17, pages 384–399, incorporated by reference herein. Resole phenolic resins are made from an alkaline catalyst and a molar excess of formaldehyde, typically having a molar ratio of formaldehyde to phenol between about 1.0:1.0 and 3.0:1.0. Novolac resins are prepared under acid catalysis and with a molar ratio of formldehyde to phenol less than 1.0:1.0. Commercially available phenolic resins suitable for use in this aspect of our invention include those known under the trade designations "DUREZ®" and VARCUM®," available from Occidental Chemicals Corporation (North Tonawanda, N.Y., U.S.A.); "RESINOX®," available from Monsanto Corporation; and "AROFENE®" and "AROTAP®," both available from Ashland Chemical Company.

The first and/or the second surfaces 1012(*a*) and 1012(*b*), respectively, of the non-woven web 1012 are coated with the aforementioned resin binder which also includes fragrance material and which also may include optional abrasive particles. Abrasive particles can also be applied in a separate step after the application of the resin binder to the web 1012. Abrasive particles suitable for use herein are preferably of 24 grade or finer, such as those normally used for finishing operations. Suitable abrasive particles include aluminum oxide including ceramic aluminum oxide, heat-treated aluminum oxide and white-fused aluminum oxide; siliconic carbide, alumina zirconia, diamond, ceria, cubic boron nitride, garnet, flint, emery and combinations of the foregoing. Additionally, abrasive agglomerates can be used, such as those described in U.S. Pat. Nos. 4,652,275 and 4,799,939, the disclosures of which are incorporated by reference herein.

Abrasive mineral-coated belts satisfactory for use in article finishing typically should have a non-woven surface having a shore $A(H_A)$ durometer, according to ASTM test method D2240-86, of about less than 10 to about 85 as measured with a 5 mm diameter "A" instrument foot. Although an $H_A$ value lower than 10 is considered to be out of the range of ASTM D2240, readings of about 5 have been measured on the softer articles of this aspect of our invention. A lower durometer measurement typically results in a belt which is easily snagged and torn by sharp corners of the workpieces, for example. Articles of higher durometer measurements are excessively dense and will frequently load up with pieces of abradant. Where the article is to be used in polishing applications, the non-woven web 1012 usually will not include abrasive particles, but may include less abrasive minerals, such as talc, for example.

The Reinforcing Fabric

The reinforcing fabric 1014 is preferably a woven stretch-resistant fabric with a low-stretch value when pulled in opposing directions. A stretch value of less than about 20% is preferred and a value of less than about 15% is more preferred. Suitable materials for use as the reinforcing fabric in the articles of this aspect of our invention include, without limitation, thermobonded fabrics, knitted fabrics, stitch-bonded fabrics and the like. Those skilled in the art will appreciate that this aspect of our invention is not to be limited to the selection of one reinforcing fabric over another, and it is contempleated that this aspect of our invention will include any type of material which otherwise has the requisite properties as set forth herein.

One aspect of the embodiment of our invention under discussion herein is the use of a reinforcing fabric comprising a woven material with sufficiently large openings therein to allow portions of the polymer layer to extend therethrough, forming discrete bonding portions 1017(*b*) with fibers of the non-woven web 1012 along the first major surface 1012(*a*). The actual dimensions of the openings can be varied depending upon the type of polymer used and the temperature at which it is applied to the fabric. Where NYLON 6® is used, the reinforcing fabric will preferably comprise plain weave fabrics having openings between the warp and fill yarns of about 0.10 mm$^2$. A plain weave fabric having 16 warp yarns and 15 fill yarns per inch (e.g., 16×16) of 84 denier nylon 66 yarns having a fabric weight of 149 g/m$^2$ (4.4 oz./yd$^2$) is most preferred for use with NYLON 6® polymer. Such a material is commercially available form Highland Industries of Greensboro, N.C., U.S.A.

Other materials may be used such as those made of polyester, cotton, animal hair, other polyamides and the like. Preferably, at least one layer of woven stetch-resistant reinforcing fabric 1014 is included with the articles 1010 and 1012 of this aspect of our invention. Additional layers of fabric (not shown) may be used in addition to the first woven fabric layer 1014 to provide additional dimensional strength as long as the openings in the woven fabrics are at least partially aligned so as not to substantially impede the extrusion of the polymer through the two fabric layers and into the non-woven layer 1012. Where two or more fabric layers are included, they are preferably positioned adjacent one another in the finished article.

The Polymer Layer

The polymer layer 1016 encapsulates the woven, stretch-resistant reinforcing fabric 1014. The polymer layer 1016 will also include fragrance material which is controllably releasable therefrom. Preferably, the polymer is applied as a hardenable, coatable composition in the form of a viscous fluid and, typically, in the molten state. With the application of pressure, the coatable composition will extrude through the openings in the reinforcing fabric 1014 and into the non-woven web 1012. In this manner, the molten polymer flows around and encapsulates fibers along the first major side 1012(*a*) of the web 1012. The polymer is then hardened in a known manner to form a reinforcing, thick, continuous polymer layer 1016, forming an outer surface of the article, which in a controllably releasable manner releases fragrance molecules into the air on use of the device which it is part of. Preferably, the polyer is applied and hardened without significant penetration through the balance of the non-woven web 1012.

The hardened polymer layer 1016 comprises a flexible low friction surface 1017(*a*) coextensive with the reinforcing fabric and portions 1017(*b*) which extend through the fabric 1014 and are bonded to fibers of the web 1012. The low friction back surface 1017(*a*) of the finished article may be planar without protrusions or depressions therein. Alternatively, the surface 1017(*a*) may be dimpled or otherwise textured to adapt the article to a particular end use. If desired, indicia may be applied to the surface 1017(*a*).

The polymer layer 1016 is formed from a coatable composition applied to the web 1012 and the fabric 1014 The coatable composition includes fragrance contained therein. the coatable composition may comprise liquid reactive components or a thermoplastic polymer material which has been sufficiently fluidized by heat, for example, and hardened to form the polymer layer 1016, as described herein. Preferred are those polymers which will harden in situ, such as by curing, and will remain solid at room temperature. Curing of the composition can be accomplished in a known manner such as by heating in an oven, exposure to ultraviolet light, the use of peroxides and the like. Alternatively, thermoplastic polymers which solidify at room temperature can also be used.

The polymer layer may be within a fairly broad range of hardness values. Preferably, the hardness will range from about Shore 50A to about Shore 80D and more preferably from about Shore 90A to about Shore 70D. It will be appreciated, however, that articles having polymer layers with hardness values outside of these ranges may be suitable for use in specific applications, and this aspect of the invention is not to be construed as limited to the foregoing hardness ranges. Materials softer than about Shore 90A may generate excessive friction and thermally degrade in certain applications, such as in those applications requiring the use of a stationary platen, for example. These softer materials, however, may be employed in belts, applications which do not require the use of a stationary platen, such as on a backstand where there is limited relative motion between the back of the surface finishing article and the driving means employed. Materials harder than about Shore 70D may be excessively stiff and, therefore, will generally be unsuitable for use in the formation of endless belts. However, such articles may be useful in some surface finishing disk applications, for example.

The thickness of the polymer layer is preferably between about 0.175 mm and about 1.75 mm and more preferably between about 0.250 mm and about 1.0 mm. Polymer layers having a thickness of less than about 0.250 mm generally lack structural integrity and durability. Layers thicker than about 1.00 mm may be undesirably stiff for use in endless belts, but may be suitable for at least some applications involving disks or pads. In general, a thickness greater than about 1.75 mm will make the article too stiff for most applications.

In selecting the polymer for the manufacture of the layer 1016, consideration is given to the end use of the finished article, allowing for the required flexibility of the article and its conformability to the surface of the workpiece. An additional consideration in the formation of endless belts is the ability of the polymer to provide a low friction surface capable of withstanding significant heat buildup caused by the application of a stationary platen, for example. An article made without the ability to withstand the heat generated during use will experience a shortened useful life and may present a safety hazard.

Preferably, the polymer employed in the articles of this aspect of our invention is a melt extruded polymer which may include in addition to fragrance, compatible fillers, pigments, reinforcing fibers, antioxidants, lubricants and the like. Suitable melt extrudable polymers for use in the invention include thermoplastics such as nylons, polyesters, polypropylene, polyethylene/vinyl acetate copolymers, acrylic/butadiene/styrene copolymers and the like. Thermoplastic elastomers such as ionomers, polyesters, polyurethanes, polyamide ethers and the like are also suitable melt extrudable polymers. The polymer layer can be formed from the polymerization of liquid reactants in the coatable composition described above, and useful reactive polymer systems include thermal or radiation cured urethane, polyester and epoxy resins. An example of a useful liquid reactive system for use in this aspect of our invention is the two part laminate adhesive composition described in Example 1 of U.S. Pat. No. 4,331,453, incorporated herein by reference. The most preferred polymer is NYLCN 6® such as that which is commercially available under the trade designation "ULTRAMID®" from BASF Corporation of Parsippany, N.J., U.S.A.

In endless belts, the polymer will preferably have a melting temperature greater than abot 115° C. as measured by differential scanning calorimetry (DSC) according to the method described in ASTM 537-86. More preferred are those polymers having a melting temperature greater than about 150° C., especially when used in endless belts which will be subjected to high workpiece pressures. Materials having melting temperatures of less than 115° C. may fail prematurely, especially in belt applications where a platen will be urged against the polymer at high pressures.

Method of Manufacture

Referring to FIG. 11, a preferred method for the manufacture of articles according to this aspect of our invention is illustrated in schematic form and will now be described in detail. A lay-up 1120, including a nor-woven web 1122, is fed from a feed roll 1124. The non-woven web 1122 may be previously needle tacked, coated and hardened as described herein. A reinforcing fabric 1126 is fed from the feed roller 1128 to a pair of counter rotating nip rolls 1130 (laminating roll) and 1132 (casting roll) where the non-woven web 1122 and the fabric 1126 are joined to form a laminate. An extruding apparatus fitted with a film die 1134 is positioned to apply a sheet of a coatable composition 1136 into the nip so that the composition is applied to the outermost surface of the scrim 1126.

The successive layers of the fabric 1126, the coatable composition 1136 and the non-woven web 1122, are passed between the rolls 1130 and 1132, which shape the composition 1136 by applying pressure to opposed sides of the aforementioned layers. The coatable composition 1136 is thereby forced through the pores or openings within the scrim 1126 and simultaneously smoothed over the outermost surface of scrim 1126. Rotating roll 1130 may be fitted with a removable surface sleeve (not shown) or it may be chrome plated or textured. Both rolls 1130 and 1132 are water cooled to a temperature sufficient to harden the composition 1136 as it passes between the rolls 1130 and 1132. Where the composition 1136 is NYLON 6®, the temperature of the roller is typically about 16° C. Where a textured or matte finish is desired for the polymer layer, the roll 1132 is coated with a textured material or is fitted with an appropriate sleeve to impart the desired finish.

In this manner, a continuous sheet 1140 of surface finishing material is formed comprising the non-woven web 1122 and the scrim 1126 bonded to one another by a hardened polymer layer. The polymer layer thus-formed comprises a smooth low friction surface coextensive with the reinforcing fabric and portions extending through the fabric forming discrete bonding areas which encapsulate fibers in the non-woven web 1122. A roll 1138 guides the continuous sheet 1140 of surface finishing material to take-up roll 1142 from. which the material 1140 may be subsequently be cut to form disks, pads, endless belts and the like.

It will be understood that the foregoing process can be modified and this aspect of the invention is not to be considered as limited to the specific steps described above. The continuous material 1140 may be fed directly from the nip rolls 1130 and 1132 to a cutting station (not shown) where the sheet 1140 may be cut into finished articles. It is also contemplated that the film die 1134 can be positioned to apply the coatable composition 1136 between the non-woven web 1122 and the scrim 1126. In such an embodiment, the pressure from the nip rolls 1130 and 1132 will be sufficient to force the molten polymer through the side of the fabric 1126 adjacent the non-woven web 1122, first coating the non-woven fibers with the composition 1136 and forcing the composition through the openings in the fabric to form the smooth continuous low friction exposed surface of the article, s discussed, supra. Other modifications to the described process may be made while remaining within the contemplated scope of this aspect of the invention.

The following Examples are illustrative, and the invention is only intended to be restricted by the claims following the Examples.

EXAMPLE I

Fragrance Permeation Test

The design and development of fragrance controlled release systems is built upon an understanding of the transport mechanisms of aroma chemicals and fragrances through polymers. The ability of the film forming polymers to sustain fragrance release was determined by permeation studies. A special diffusion cell has been developed to measure the steady state permeation of aroma chemicals and fragrances through polymeric films using weight loss. The diffusion cell designed for the fragrance permeation studies (shown in FIGS. 4A and 4B, described in detail, supra) is composed of a reservoir system having a maximum volume of about 12 cm$^3$ and a surface area of about 4.5 cm$^2$. The polymeric film is mounted on the diffusion cell and is tightly secured by a glass ring fitted with three screws. The film thickness averages from about 50 m to about 1 mm. The diffusant (fragrances, single or mixture of aroma chemicals) is kept in contact with the polymer film throughout the experiment period by filling the diffusion cell arm with the diffusant. The permeation rate of the diffusant is determined by monitoring the changes in the diffusion cell weight.

The permeability coefficient, or permeability P, is useful in describing the rate of mass transport through a polymer at steady state. Permeability is related to two basic properties: diffusion and solubility. The permeability coefficient can be expressed by the diffusion coefficient (D) and the solubility coefficient (S) Their relationship is described by the following equation:

$$P = D \cdot S.$$

The solubility coefficient is a thermodynamic term, describing the affinity of a penetrant for the polymer, i.e, the amouunt of permeant dissolved in the polymer matrix at equilibrium conditions. Solubility affects the concentration gradient (driving force), whereas the diffusion coefficient is a kinetic term and describes the rate at which permeant moves through the polymer.

The mathematical theory of diffusion in isotropic materials is based on the hypothesis that the rate of transfer of diffusing substance through unit area of a section is proportional to the concentration gradient measure normal to the section (Fick's first and second laws of diffusion):

$$F = -D\frac{\partial C}{\partial X} \text{ and } \frac{\partial C}{\partial t} = \frac{\partial}{\partial X}\left(D\frac{\partial C}{\partial X}\right) = D\frac{\partial^2 C}{\partial X^2},$$

wherein:

F=flux;

D=diffusion coefficient;

C=concentration of the diffusing molecule;

X=distance across which material diffuses; and t=time.

At steady state, the diffusion flux (F) of a permeant in a polymer is defined as the amount of penetrant which passed through a unit surface area per unit time:

$$F = \frac{Q}{At},$$

wherein:

Q=amount of diffusing molecules transferring through the film;

A=cross-sectional area; and t=time.

The diffusion flux (F) of the percent can be integrated through the total thickness of the polymer between the two concentrations, assuming that the diffusion coefficient (D) is constant and independent of concentration:

$$F = \frac{D(C_1 - C_2)}{L},$$

wherein $C_1$ and $C_2$ are the concentrations of the penetrant on the boundary with the polymer film (@ X=0) and the film surface with air (@ X=L), respectively, ($C_1 > C_2$); and L=film thickness.

From these equations, one can calculate the amount of penetrant (Q=dM/dt):

$$Q = \frac{D(C_1 - C_2)At}{L}.$$

This value is the actual weight loss that is being measured during our experiments. By substituting D with P and S using the definition of permeability (equation 1): P=DS and the use of neat material (not dilution in a solvent), one can then solve the equation to determine the permeability coefficient using the cell dimension (surface area, A), the thickness of the film (L) and the weight loss data (Q=dM/dt):

$$P = \frac{QL}{A}.$$

EXAMPLE II

Permeation Through Hydroxypropyl Cellulose

The effect of fragrance physical and chemical properties on its permeation rate through the film forming polymers was studied using the experimental setup described, supra. FIG. 5B, described in detail, supra, presents the effect of $\log_{10}P$ on the permeation rate of the two model aroma chemicals through hydroxypropyl cellulose. The permeation studies were carried out at 35° C., and the temperature was kept constant within ±0.5° C. throughout the experiment period. The thickness of the films studied was about 150 microns. The aroma chemicals studied, ethyl tiglate and β-pinene, have approximately the same values of vapor pressure, but differ in their solubility in water. Ethyl tiglate has a lower value of $\log_{10}P$ and thus is more water soluble than β-pinene.

From an inspection of FIG. 5B, it can be clearly observed that hydroxypropyl cellulose is an excellent barrier to β-pinene. The permeation rate of β-pinene through hydroxypropyl cellulose is $$2.7 \times 10^{-4} \left( \frac{mg - mm}{cm^2 - min} \right),$$

whereas the evaporation rate of this aroma chemical at the same temperature without the polymer is about $$0.15 \left( \frac{mg - mm}{cm^2 - min} \right).$$

The permeation rate of ethyl tiglate through hydroxypropyl cellulose is exactly the same as its evaporation rate without the polymer. This suggests that the polymer has been dissolved by this aroma chemical and it is no longer a barrier to its diffusion. This example clearly demonstrates that the fragrance or fragrance ingredient to be applied with a particular polymeric film should be carefully chosen in creating the design of a fragrance controlled release system using the technology of our invention.

EXAMPLE III

Permaeation Through Polyvinyl Alcohol

The permeation rates on two model aroma chemicals having a high and low $\log_{10}P$ through a polyvinyl alcohol, having crystalline and better packed structure, were also studied and are illustrated in FIG. 5C, described in detail, supra. The permeation studies were carried out at 35° C., and the temperature was kept constant within ±0.5° C. throughout the experiment period. The thickness of the films studied was about 150 microns. The aroma chemicals studied, ethyl tiglate and β-pinene, have about the same values of vapor pressure, but differ in their solubility in water. Ethyl tiglate has a lower value of $\log_{10}P$ and thus is more water soluble than β-pinene.

Polyvinyl alcohol is an excellent barrier for aroma chemicals with high (β-pinene) and low (ethyl tiglate) $\log_{10}P$ values. The permeation rates of both aroma chemicals through polyvinyl alcohol are about $$1.8 \times 10^{-4} \left( \frac{mg - mm}{cm^2 - min} \right).$$

The evaporation rate of these aroma chemicals at the same temperature without the polymer is about $$0.15 \left( \frac{mg}{cm^2 - min} \right).$$

This example clearly demonstrates that the fragrance or fragrance ingredient to be applied with a particular polymeric film should be carefully chosen in creating the design of a fragrance control release system using this technology.

EXAMPLE IV

Film Forming Technology for Fragrance Controlled Release

The potential application of the film forming technology to sustain the release of fine fragrances (longer lasting fragrances) was studied using Solid Phase Micro Extraction. A volatile accord containing four aroma chemicals as follows:

| Ingredient | Percentage |
|---|---|
| C.P. FORMATE ® having the structure: 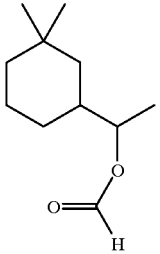 | 25% |
| d-Limonene having the structure: 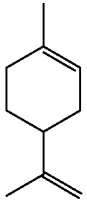 | 25% |
| β-Pinene having the structure: 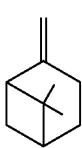 | 25% |
| Prenyl acetate having the structure: | 25% |

| Ingredient | Percentage |
|---|---|
| 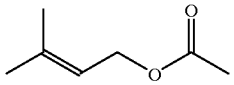 | | was used as a model fine fragrance in these studies. A system containing 20% of this volatile accord (mixture of four chemicals) and 1% of a film forming polymer (ADVPNTAGE PLUS having the structure:

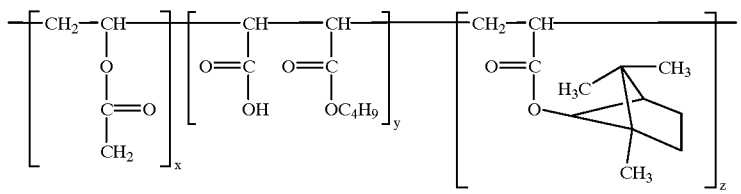

wherein each of x, y and z are each integers equal to 8) and polyvinyl alcohol (98% hydrolyzed polyvinyl acetate) in ethanol was studied on blotter and on skin. The results were compared to a control containing 20% fragrance in ethanol. Fragrance intensity in the headspace above the sample was determined by measuring the total gas chromatography (GC) peak area at different time intervals. The intensity of the fragrance in the headspace above the blotter as shown in FIGS. 6A and 6B (described in detail, supra) was much higher for the fragrance and polymer than for the control for both polymers studied.

Similar behavior was found for the study of this four component fragrance on the skin, and the data therefor is shown in FIG. 6D, described in detail, supra.

EXAMPLE V

Preparation of Deodorant Stick

In each of the following cases, a given polymer is admixed with propylene glycol and water. To the polymer-propylene glycol-water mixture, sodium stearate is slowly added with mixing, and the resulting mixture is heated to 80° C. until dissolved. At that point in time, fragrance is added, and the resulting material is then admixed and poured into molds. The resulting deodorant stick creates a long lasting (24 hours) fragrance effect on the wearer after one application:

EXAMPLE V(A)

| Ingredient | Parts by Weight |
|---|---|
| Propylene glycol | 38.4 grams |
| Water | 16.2 grams |
| Sodium stearate | 4.2 grams |
| Carboxymethyl cellulose | 0.6 grams |
| Fragrance consisting of equal parts by weight of: C.P. FORMATE ® having the structure: | 0.6 grams |

| Ingredient | Parts by Weight |
|---|---|
| 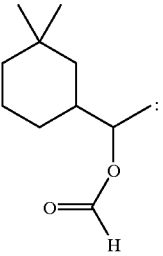 | | d-limonene having the structure:

β-pinene having the structure:

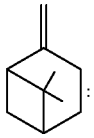

and prenyl acetate having the structure:

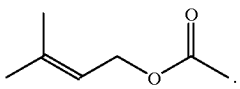.

EXAMPLE V(B)

| Ingredient | Parts by Weight |
|---|---|
| Propylene glycol | 37.8 grams |
| Water | 16.2 grams |
| Sodium stearate | 4.2 grams |
| Carboxymethyl cellulose | 1.2 grams |
| Fragrance as described in Example V (A) | 0.6 grams |

EXAMPLE V(C)

| Ingredient | Parts by Weight |
|---|---|
| Propylene glycol | 38.4 grams |
| Water | 16.2 grams |
| Sodium stearate | 4.2 grams |
| Polyvinyl alcohol (98% hydrolyzed polyvinyl acetate) (molecular weight range = 31,000–50,000 daltons) | 0.6 grams |
| Fragrance as described in Example V (A) | 0.6 grams |

EXAMPLE V(D)

| Ingredient | Parts by Weight |
|---|---|
| Propylene glycol | 31.0 grams |
| Water | 13.5 grams |
| Sodium stearate | 3.5 grams |
| Fragrance as described in Example V (A) | 1.0 grams |
| Polyvinyl alcohol (98% hydrolyzed polyvinyl acetate) (molecular weight range = 13,000–23,000 daltons) | 1.0 grams |

EXAMPLE V(E)

| Ingredient | Parts by Weight |
|---|---|
| Propylene glycol | 31.0 grams |
| Water | 13.5 grams |
| Sodium stearate | 3.5 grams |
| Fragrance as described in Example V (A) | 1.0 grams |
| Hydroxypropyl cellulose (molecular weight = 100,000 daltons) | 1.0 grams |

EXAMPLE V(F)

| Ingredient | Parts by Weight |
|---|---|
| Propylene glycol | 32.0 grams |
| Water | 13.5 grams |
| Sodium stearate | 3.5 grams |
| Gelatin | 0.5 grams |
| PACIFIC LIGHT ® Fragrance | 0.5 grams |

EXAMPLE V(G)

| Ingredient | Parts by Weight |
|---|---|
| Propylene glycol | 62.0 grams |
| Water | 27.0 grams |
| Sodium stearate | 7.0 grams |
| CASHMERAN ® (registered trademark of International Flavors & Fragrances Inc.) having the structure: | 0.045 grams |

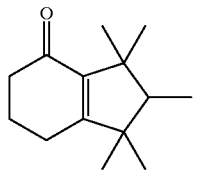

| | |
|---|---|
| Hydroxypropyl cellulose (molecular weight = 100,000 daltons) | 2.0 grams |

EXAMPLE V(H)

| Ingredient | Parts by Weight |
|---|---|
| Propylene glycol | 62.0 grams |
| Water | 27.0 grams |
| Sodium stearate | 7.0 grams |
| CASHMERAN ® | 0.045 grams |
| Polyvinyl alcohol (98% hydrolyzed polyvinyl acetate) (molecular weight range = 31,000–50,000 daltons) | 2.0 grams |

The following deodorant stick controls were prepared:

| Ingredient | Parts by Weight |
|---|---|
| CONTROL V (I) | |
| Propylene glycol | 64.0 grams |
| Water | 27.0 grams |
| Sodium stearate | 7.0 grams |
| CASHMERAN ® | 0.045 grams |
| CONTROL V (J) | |
| Propylene glycol | 64.0 grams |
| Water | 27.0 grams |
| Sodium stearate | 7.0 grams |
| CASHMERAN ® | 0.01 grams |
| CONTROL V (K) | |
| Propylene glycol | 32.0 grams |
| Water | 13.5 grams |
| Sodium stearate | 3.5 grams |
| Fragrance as described in Example V (A) | 1.0 grams |

Controls V(I), V(J) and V(K) gave rise to "zero" fragrance perception after 3 hours and were far inferior to the deodorant sticks prepared using the ingredients of Examples V(A)–V(H), inclusive.

EXAMPLE VI(A)

20 Grams of the fragrance of Example IV is admixed with a mixture of 365 ml of water and 195 ml of methanol. 100 Grams of VINOL® 107 polyvinyl alcohol manufactured by Air Products and Chemical Company of Allentown, Pa. was dissolved in the resulting mixture by heating with good agitation under 4 atmospheres pressure.

When the fragrance-polymer accord was completely dissolved, an additional 195 ml of methanol was added slowly over 1 hour with vigorous mixing to avoid local concentrations of methanol which precipitates the polymer, followed by 10 grams of 2-ethylhexanal and 3 ml of concentrated hydrochloric acid. The resulting product had 7% of the hydroxyl groups converted to acetal groups. When more than 10 grams of 2-ethylhexanal was added, the polymer precipitated from this alcohol-water-perfume mixture. After 7 hours of ref-Luxing, an infrared test was run on the cast film showing no carbonyl band and the solution was cooled to room temperature. The solution viscosity was adjusted to 2,000 centipoises (cps) by adding 150 ml of a 60% mixture of methanol-water to give an 11% solids content, and finally 1 gram of CYMEL® 303, hexamethoxymethylmelamine (manufactured by the American Cyanamide Company of Boundbrook, N.J., U.S.A.) was added. The final product, a stable solution, slightly cloudy when chilled, was applied directly to a textile substrate, namely RIPSTOP® Nylon. Dried films cast from the polymer solution were clear, strong, flexible and water-insoluble.

The above-solution was coated onto a substrate of RIPSTOP® Nylon by drawdown with a wirewound rod and oven-dried at 90° C. The moisture permeability of the coating was compared to the uncoated nylon and to a sample cut from a popular laminated garment. A measured ounce of water was placed into a mason jar and then a fabric disk was sealed onto a rubber gasket on the top of the jar with a screw cap from which the metal center has been removed. The jars were placed together on a thermostated electric warming tray. Under these conditions, the time to complete evaporation of

| uncoated RIPSTOP ® Nylon | 11 hours; |
| coated RIPSTOP ® Nylon | 26 hours; and |
| commercial waterproof laminate | 72 hours. |

The water resistance was tested by sealing the fabric sample to a water-filled mason jar with the coated side against the water. The jar was inverted and watched for drips through the fabric. After 8 hours, no water had penetrated the fabric.

In addition, fragrance intensity was measured in the headspace above the mason jar, in the same manner as the measurements used for formulation of the graphs of FIGS. 6A and 6B. The resulting fragrance intensity-time profiles were closely similar to those as set forth in FIGS. 6A and 6B, described supra.

EXAMPLE VI(B)

A reaction similar to that carried out Example VI with 140 grams of polyvinyl alcohol and 14 grams of acetaldehyde yielded a solution of partial acetal with 20% of the hydroxyl groups converted. To this solution was added 1.5 grams of CYMEL® 303 and the solution was applied to fabric as above. Again, a water-insoluble coating was formed which was highly permeable to water vapor and which gave rise to a good fragrance intensity-time profile, similar to that shown in FIGS. 6A and 6B, described supra.

EXAMPLE VI(C)

140 Grams of polyvinyl alcohol was dissolved in a mixture of 715 ml of water, 275 ml of methanol and 30 grams of the fragrance of Example IV, supra. To this was added 11.5 grams of hexadecyl aldehyde and 4 ml of concentrated hydrochloric acid to convert 3% of the hydroxyl groups to acetals. After several hours of refluxing, the product polymer was filtered from the solution, redissolved in dioxane to form a 10% solution and applied to fabric. The moisture vapor transmission was at least as high as Example VI(A) and, in some cases, substantially higher. The dried polymer film was insoluble in water. The dried polymer film gave rise to a fragrance headspace above the film closely similar to that as set forth in FIGS. 6A and 6B, described supra.

EXAMPLE VI(D)

688 Grams of polyvinyl acetate (viscosity of 45 cps at 60° C. dissolved in benzene) was dissolved in 3,200 ml of methanol, 800 ml of 4.6 n-methanolic hydrochloric acid and 210 grams of the fragrance of Example IV, supra. The reaction produced a water-soluble product in 2.5 hours. 78.4 Grams of cyclohexanone was added to the solution, and the solution was then allowed to stand for 18 hours until an infrared scan showed minimal carbonyl groups. 10% Of the hydroxyl groups were converted to acetal groups. This solution was applied to cotton fabric and tested in the same manner as described in Example VI(A), supra. The resulting cotton fabric provided a water vapor permeable, but water impenetrable coated fabric. The resulting fabric also gave rise to a fragrance headspace-time profile closely similar to that set forth in FIGS. 6A and 6B, described supra.

Those skilled in the art having the benefit of the teachings of present invention as hereinabove set forth can effect numerous modifications thereto. These modifications are to be construed as being encompassed within the scope of the present invention as set forth in the appended claims.

What is claimed is:

1. A woven or non-woven fabric having coated thereon an emulsifier-free, single phase, nonporous, continuous, permeable polymeric film having a substantially uniform uniform thickness of from about 5 microns up to about 150 microns, having entrapped and dissolved therein molecules of at least one fragrance substance capable of evolving from said film into the environment proximate said film by means of molecular diffusion at a permeation rate of from about $1\times10^{-7}$ up to about $$0.1\left(\frac{mg-mm}{cm^2-min}\right)$$

in a sustained and controlled release manner.

2. A woven or non-woven fabric of claim 1 wherein the film coated thereon is an an emulsifier-free, single phase, nonporous, continuous, permeable, polymeric film comprising a polymer and a fragrance substance located on the surface of the woven or non-woven fabric support, said polymeric film having two substantially parallel laminar surfaces, a first laminar polymer surface and a second laminar polymer surface, said second laminar polymer surface being juxtaposed with at least a portion of said surface of a planar woven or non-woven fabric support, said polymeric film having a substantially uniform thickness of from 1 up to about 150 microns, said polymeric film having entrapped and dissolved therein molecules of at least one fragrance substance having an initial weight ratio $R_i$ of fragrance:polymer of from about 0.01:20 up to about 50:0.01, said fragrance substance being:
   (i) capable of evolving from within the polymeric film through said first laminar polymer surface into the environment proximate to and above said first laminar polymer surface by means of substantially steady state molecular diffusion at a substantially constant permeation rate of from about $1\times10^{-7}$ up to about $$0.1\left(\frac{mg-mm}{cm^2-min}\right)$$

in a sustained and controlled release manner; and (ii) substantially incapable of permeating that portion of said second laminar polymer surface which is juxtaposed with the surface of said woven or non-woven fabric support, said polymeric film having two regions located across the cross-section of said polymeric film, taken along the directional vector from said first laminar polymer surface to said second laminar polymer surface:

(a) a first permeation region proximate and immediately adjacent to said first laminar polymer surface; and (b) a second reservoir region proximate and immediately adjacent to said second laminar polymer surface, said first permeation region being juxtaposed with said second reservoir region, said second reservoir region containing a high proportion of said fragrance substance relative to the proportion of said fragrance substance contained in said first permeation region.

3. A woven or non-woven fabric of claim 1 having coated thereon a film which is an an emulsifier-free single phase, nonporous, continuous, permeable polymeric-gel film comprising:

(i) a water-soluble or water-swellable polymer;
(ii) a fragrance material;
(iii) water; and
(iv) a gelling agent composition comprising at least one gelling agent, said film being located on the surface of said woven or non-woven fabric support, said polymeric-gel film having two substantially parallel laminar surfaces:

(i) a first laminar polymeric-gel surface; and (ii) a second laminar polymeric-gel surface, said second polymeric-gel surface being juxtaposed with at least a portion of said surface of said woven or non-woven fabric support, said polymeric-gel film having a substantially uniform thickness of from about 1.0 microns up to about 150 microns, said polymeric-gel film having entrapped and dissolved therein:

(i) molecules of at least one fragrance substance in an initial weight ratio of fragrance:polymeric gel of from about 0.01:20 up to about 50:0.01; and (ii) water molecules in an initial weight ratio of water:polymeric gel of from about 1:500 up to about 500:1, said molecules of fragrance substance and said molecules of water being uniformly dispersed in a single phase throughout said polymeric-gel film, said fragrance substance being:

(a) capable of evolving from within the polymeric gel film through said first laminar polymeric-gel surface into the environment proximate said first laminar polymeric-gel surface by means of molecular diffusion at a permeation rate of from about $1\times10^{-7}$ up to about $$0.1\left(\frac{mg-mm}{cm^2-min}\right)$$

in a substantially controlled release manner in accordance with Fick's second law; and (b) substantially incapable of permeating that portion of said second laminar polymeric-gel surface which is juxtaposed with said surface of said woven or non-woven fabric support.

4. A woven or non-woven fabric of claim 3 wherein in the polymeric-gel film coated thereon, the gelling agent composition comprises a metal stearate and polypropylene glycol.

* * * * *